US008846742B2

(12) United States Patent
Ambron et al.

(10) Patent No.: US 8,846,742 B2
(45) Date of Patent: Sep. 30, 2014

(54) NEURONAL PAIN PATHWAY MODULATORS

(75) Inventors: Richard Ambron, Lake Success, NY (US); Ying-Ju Sung, Northvale, NJ (US); Jeremy Greenwood, Brooklyn, NY (US); Leah Frye, Portland, OR (US); Shi-Xian Deng, White Plains, NY (US); Yuli Xie, New York, NY (US); Donald W. Landry, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1018 days.

(21) Appl. No.: 11/674,965

(22) Filed: Feb. 14, 2007

(65) Prior Publication Data

US 2008/0176920 A1 Jul. 24, 2008

Related U.S. Application Data

(60) Provisional application No. 60/773,691, filed on Feb. 14, 2006, provisional application No. 60/815,980, filed on Jun. 23, 2006.

(51) Int. Cl.
*A61K 31/415* (2006.01)
*A61K 31/335* (2006.01)

(52) U.S. Cl.
CPC .................................. *A61K 31/335* (2013.01)
USPC ........... 514/403; 514/426; 514/424; 514/532; 514/455

(58) Field of Classification Search
CPC .. C07D 231/56; C07D 231/06; C07D 231/54; C07D 401/04; C07D 401/12
USPC .................. 514/403, 426, 424, 532, 455, 416
See application file for complete search history.

(56) References Cited

U.S. PATENT DOCUMENTS

| 4,708,716 | A | 11/1987 | Sibalis |
| 5,405,614 | A | 4/1995 | D'Angelo et al. |
| 5,432,198 | A | 7/1995 | Jagdmann, Jr. |
| 5,583,221 | A | 12/1996 | Hu et al. |
| 6,376,467 | B1 | 4/2002 | Messing et al. |
| 6,476,007 | B2 | 11/2002 | Tao et al. |
| 6,686,334 | B2 | 2/2004 | Messing et al. |
| 8,252,754 | B2 | 8/2012 | Ambron et al. |
| 2003/0083262 | A1 | 5/2003 | Hannig et al. |
| 2003/0181716 | A1 | 9/2003 | Friebe et al. |
| 2006/0216339 | A1* | 9/2006 | Ambron et al. ............... 424/449 |
| 2012/0295853 | A1 | 11/2012 | Ambron et al. |

FOREIGN PATENT DOCUMENTS

| JP | 2000-504697 | 4/2000 |
| WO | WO/93/03730 | 3/1993 |
| WO | WO/2004/017941 | 3/2004 |
| WO | WO/2006/102267 | 9/2006 |

OTHER PUBLICATIONS

The Merck Manual, Fifteenth Edition, 1987, pp. 1340-1356.*
Neuropathic Pain: Diagnosis, Treatment, and the Pharmacist's Role in Patient Care, Pharmacy Times, 2005.*
Abdulla FA, Smith PA; (2001); Axotomy- and autotomy-induced changes in the excitability of rat dorsal root ganglion neurons; J Neurophysiol; 85:630-643.
Ambron RT, Dulin MF, Zhang XP, Schmied R, Walters ET; (1995); Axoplasm enriched in a protein mobilized by nerve injury induces memorylike alterations in *Aplysia neurons*; J Neurosci; 15:3440-3446.
Bedi SS, Salim A, Chen S, Glanzman DL, (1998), Long-term effects of axotomy on excitability and growth of isolated *Aplysia* sensory neurons in cell culture: potential role of cAMP. J Neurophysiol, 79:1371-1383.
Breitenlechner CB, Wegge, T, Berillon, L, Graul, K, Marzenell, K, Friebe, W, Thomas, U, Schumacher, R, Huber, R, Engh, RA, Masjost, B; (2004); Structure-based optimization of novel azepane derivatives as PKB inhibitors; J. Med. Chem; 47:1375-1390.
Bryan J; (2004); Transdermal drug delivery may be a common technique in the future. Pharmaceutical J; 273:292-293.
Chen Y, Devor M; (1998); Ectopic mechanosensitivity in injured sensory axons arises from the site of spontaneous electrogenesis; Eur J Pain; 2:165-178.
Friesner, R. A.; Banks, J. L.; Murphy, R. B.; Halgren, T. A.; Klicic, J. J.; Mainz, D. T.; Repasky, M. P.; Knoll, E. H.; Shelley, M.; Perry, J. K.; Shaw, D. E.; Francis, P.; Shenkin, P. S; (2004); Glide: A New Approach for Rapid, Accurate Docking and Scoring. 1. Method and Assessment of Docking Accuracy; J. Med. Chem; 47: 1739-1749.
Gracely, RH; Lynch, SA; Bennett, GJ; (1992); Painful neuropathy: altered central processing maintained dynamically by peripheral input; Pain.51:175-194.
Gunstream, JD; Castro, GA; Walters, ET; (1995); Retrograde transport of plasticity signals in Aplysia sensory neurons following axonal injury; J Neurosci; 15:439-448.
Halgren, T. A.; Murphy, R. B.; Friesner, R. A.; Beard, H. S.; Frye, L. L.; Pollard, W. T.; Banks, J. L; (2004); Glide: A New Approach for Rapid, Accurate Docking and Scoring. 2. Enrichment Factors in Database Screening; J. Med. Chem; 47:1750-1759.
Jacobson, M. P.; Pincus, D. L.; Rapp, C. S.; Day, T. J. F.; Honig, B.; Shaw, D. E.; Friesner, R. A; (2004); A Hierarchical Approach to All-Atom Protein Loop Prediction; Proteins; 55: 351-357.
Kim, YI; Na, HS; Kim, SH; Han, HC; Yoon, YW; Sung, B; Nam, HJ; Shin, SL; Hong, SK; (1998); Cell type-specific changes of the membrane properties of peripherally-axotomized dorsal root ganglion neurons in a rat model of neuropathic pain; Neuroscience; 86:301-309.
Koide, K; Bunnage, M; Paloma, L; Kanter, J; Taylor, S; Brunton, L; and Nicolaou, K; (1995); Molecular design and biological activity of potent and selective protein kinase inhibitors related to balanol; Chem and Bio; 2(9):601-608.

(Continued)

*Primary Examiner* — Jason Sims
*Assistant Examiner* — Ibrahim D Bori
(74) *Attorney, Agent, or Firm* — Baker Botts, L.L.P.

(57) ABSTRACT

The present invention relates to compounds that may be used to inhibit activation of protein kinase G ("PKG"). It is based, at least in part, on the discovery of the tertiary structure of PKG and the identification of molecules that either bind to the active site of PKG and/or are analogs of balanol.

1 Claim, 52 Drawing Sheets

(56) References Cited

OTHER PUBLICATIONS

Lai,YS; Mendoza, JS; Jagdmann, GE; Menaldino, DS; Biggers, CK; Heerding, JM; Wilson, JW; Hall, SE; Jiang, JB; Janzen, WP; Ballas, LM; (1997); Synthesis and protein kinase C inhibitory activities of balanol analogs with replacement of the perhydroazepine moiety; J. Med. Chem;.40:226-235.

LaMotte, RH; Shain, CN; Simone, DA; Tsai, EFP; (1991); Neurogenic hyperalgesia: psychophysical studies of underlying mechanisms; J Neurophysiol; 66:190-211.

Lee, JH; Orice, RH; Williams, FG; Mayer, B; Beitz, AJ; (1993); Nitric oxide synthase is found in some spinothalamic neurons and in neuronal processes that appose spinal neurons that express Fos induced by noxious stimulation; Brain Res; 608:324-333.

Lewin, MR; Walters, ET; (1999); Cyclic GMP pathway is critical for inducing long-term sensitization of nociceptive sensory neurons; Nat Neurosci; 2:18-23.

Lin, H; Bao, J; Sung, YJ; Walters, ET; Ambron, RT; (2003); Rapid electrical and delayed molecular signals regulate the serum response element after nerve injury: convergence of injury and learning signals; J Neurobiol; 57:204-220.

Mai et al; (2002); Efficiency of protein transduction is cell type-dependent and is enhanced by dextran sulfate; J Biol Chem; 277:30208-30218.

Millan, MJ; (1999); The induction of pain: an integrative review; Prog Neurobiol; 57:1-164.

Palecek, J; Paleckova, V; Willis, WD; (2003); Fos expression in spinothalamic and postsynaptic dorsal column neurons following noxious visceral and cutaneous stimuli; Pain; 104:249-257.

Park, SY; Choi, JY; Kim, RU; Lee, YS; Cho, HJ; Kim, DS; (2003); Downregulation of voltage-gated potassium channel a gene expression by axotomy and neurotrophins in rat dorsal root ganglia; Mol Cells; 16:256-259.

Study, RE; Kral, MG; (1996); Spontaneous action potential activity in isolated dorsal root ganglion neurons from rats with a painful neuropathy; Pain; 65:235-242.

Sung, YJ; Povelones, M; Ambron, RT; (2000); RISK-1: a novel MAPK homologue in axoplasm that is activated and retrogradely transported after nerve injury; J Neurobiol; 47:67-79.

Sung, YJ; Walters, ET; and Ambron, RT; (2004); A neuronal isoform of protein kinase G couples mitogen-activated protein kinase nuclear import to axotomy-induced long-term hyperexcitability in *Aplysia* sensory neurons; J. Neurosci; 24(34):7583-7595.

Ungless, MA; Gasull, X; Walters, ET; (2002); Long-term alteration of S-type potassium current and passive membrane properties in *Aplysia* sensory neurons following axotomy; J Neurophysiol; 87:2408-2420.

Urban, MO; Gebhart, GF; (1999); Supraspinal contributions to hyperalgesia; Proc Natl Acad Sci USA; 96:7687-7692.

Urban, MO; Gebhart, GF; (1998); The glutamate synapse: a target in the pharmacological management of hyperalgesic pain states; Prog Brain Res; 116:407-420.

Wall, PD; Devor, M; (1983); Sensory afferent impulses originate from dorsal root ganglia as well as from the periphery in normal and nerve injured rats; Pain; 17:321-339.

Walters, ET; Byrne, JH; Carew, TJ; Kandel, ER; (1983a); Mechanoafferent neurons innervating tail of *Aplysia*. I. Response properties and synaptic connections; J Neurophysiol; 50:1522-1542.

Walters, ET; Byrne, JH; Carew, TJ; Kandel, ER; (1983b); Mechanoafferent neurons innervating tail of *Aplysia*. II. Modulation by sensitizing stimulation; J Neurophysiol; 50:1543-1559.

Walters, ET; Alizadeh, H; Castro, GA; (1991); Similar neuronal alterations induced by axonal injury and learning in *Aplysia*; Science; 253:797-799.

Walters, ET; Bodnarova, M; Billy, AJ; Dulin, MF; Diaz-Rios, M; Miller, MW; Moroz, LL; (2004); Somatotopic organization and functional properties of mechanosensory neurons expressing sensorin-A mRNA in *Aplysia californica*; J Comp Neurol; 471:219-240.

Wang, H; Sun, H; Della, Penna, K; Benz, RJ; Xu, J; Gerhold, DL; Holder, DJ; Koblan, KS; (2002); Chronic neuropathic pain is accompanied by global changes in gene expression and shares pathobiology with neurodegenerative diseases; Neuroscience; 114:529-546.

Waxman, SG; Kocsis, JD; Black, JA; (1994); Type III sodium channel mRNA is expressed in embryonic but not adult spinal sensory neurons, and is reexpressed following axotomy; J Neurophysiol; 72:466-470.

Wenderer et al; (2000); The design, synthesis, and evaluation of molecules that enable or enhance cellular uptake: peptoid molecular transporters; Proc Natl Acad Sci U S A; 97: 13003-13008.

Woolf, CJ; (1983); Evidence for a central component of post-injury pain hypersensitivity; Nature; 306:686-688.

Zhang, H; Xie, W; Xie, Y; (2005); Spinal cord injury triggers sensitization of wide dynamic range dorsal horn neurons in segments rostral to injury. Aug. 2, 2005 Brain Res, epub ahead of print; PMID 16083864.

Zhang, JM; Donnelly, DF; Song, XJ; Lamotte, RH; (1997); Axotomy increases the excitability of dorsal root ganglion cells with unmyelinated axons; J Neurophysiol; 78:2790-2794.

Zhu, GD; Gong, J; Ghandi, V; Woods, K; Luo, Y; Liu, X; Guan, R; Klinghofer, V; Johnson, E; Stoll, V; Mamo, M; Li, Q; Rosenberg, S; Giranda, V; (2007); Design and Synthesis of Pyridine-Pyrazolopyridine-Based Inhibitors of Protein Kinase B/Akt; J. Med. Chem; 15: 2441-2452.

U.S. Appl. No. 11/385,455, filed Aug. 28, 2012, Ambron et al.
U.S. Appl. No. 13/569,510, filed Nov. 22, 2012, Ambron et al.
U.S. Appl. No. 11/385,455, Jul. 24, 2012 Issue Fee payment.
U.S. Appl. No. 11/385,455, Apr. 25, 2012 Notice of Allowance.
U.S. Appl. No. 11/385,455, Feb. 3, 2011 Amendment and Request for Continued Examination (RCE).
U.S. Appl. No. 11/385,455, Aug. 5, 2010 Final Office Action.
U.S. Appl. No. 11/385,455, Apr. 29, 2010 Response to Non-Final Office Action.
U.S. Appl. No. 11/385,455, Oct. 29, 2009 Non-Final Office Action.
U.S. Appl. No. 11/385,455, Aug. 12, 2009 Amendment and Request for Continued Examination (RCE).
U.S. Appl. No. 11/385,455, filed May 12, 2009 Final Office Action.
U.S. Appl. No. 11/385,455, Feb. 10, 2009 Response to Non-Final Office Action.
U.S. Appl. No. 11/385,455, Oct. 10, 2008 Non-Final Office Action.
U.S. Appl. No. 11/385,455, Oct. 1, 2008 Response to Restriction Requirement.
U.S. Appl. No. 11/385,455, Jul. 2, 2008 Restriction Requirement.
U.S. Appl. No. 11/385,455, May 7, 2008 Amendment and Request for Continued Examination (RCE).
U.S. Appl. No. 11/385,455, Mar. 21, 2008 Supplemental Response.
U.S. Appl. No. 11/385,455, Mar. 11, 2008 Response to Final Office Action.
U.S. Appl. No. 11/385,455, Dec. 7, 2007 Final Office Action.
U.S. Appl. No. 11/385,455, Nov. 26, 2007 Supplemental Response.
U.S. Appl. No. 11/385,455, Sep. 24, 2007 Response to Non-Final Office Action.
U.S. Appl. No. 11/385,455, Jun. 22, 2007 Non-Final Office Action.
U.S. Appl. No. 13/569,510, Jan. 17, 2014 Non-Final Office Action.
U.S. Appl. No. 13/569,510, Oct. 2, 2013 Response to Restriction Requirement.
U.S. Appl. No. 13/569,510, Apr. 3, 2013 Restriction Requirement.

Agrawal, et al., (2000) "Antisense therapeutics: is it as simple as complementary base recognition?", *Molecular Medicine Today*, 6:72-81.

Alberini, et al., (1994) C/EBP is an immediate-early gene required for the consolidation of long-term facilitation in Aplysia:, *Cell*, 76:1099-1114.

Aley, et al., "Role of protein kinase A in the maintenance of inflammatory pain", *The Journal of Neuroscience*, 19(6):2181-2186 (1999).

Ambron, et al., (1992) "A signal sequence mediates the retrograde transport of proteins from the axon periphery to the cell body and then into the nucleus", *J Neurosci.*, 12:2813-2818.

Ambron, et al., (1996) "Priming events and retrograde injury signals. A new perspective on the cellular and molecular biology of nerve regeneration", *Mol. Neurobiol*, 13:61-79.

(56) References Cited

OTHER PUBLICATIONS

Ambron, et al., (1996) "Intrinsic injury signals enhance growth, survival, and excitability of Aplysia neurons", *J Neurosci.*, 16;7469-7477.
Antonov, et al., (2003) "Activity-dependent presynaptic facilitation and hebbian LTP are both required and interact during classical conditioning in Aplysia", *Neuron*, 37:135-147.
Ausubel, et al., eds. (1989) Current Protocols in Molecular Biology, vol. I, Green Publishing Associates, Inc., and John Wiley & sons, Inc., New York, at p. 2.10.3.
Bartsch, et al. (1995) "Aplysia CREB2 represses long-term facilitation: relief of repression converts transient facilitation into long-term functional and structural change", *Cell*, 83:979-992.
Bennett, et al., (2005) "The S-LANSS score for identifying pain of predominantly neuropathic origin: validation for use in clinical and postal research", *J Pain.*, 6(3):149-58.
Billy, et al. (1989) "Long-term expansion and sensitization of mechanosensory receptive fields in Aplysia support an activity-dependent model of whole-cell sensory plasticity", *J Neurosci.*, 9:1254-1262.
Biology Workbench, a point and click interface for searching protein and nucleic acid sequence databases and for analyzing sequence data. Hosted at workbench.sdsc.edu/ (2005).
"Block-iT™ RNAi Designer", by Invitrogen, carlsbad, CA [retrieve on Jun. 26, 2009] Retrieved from the internet: URL:https://rnaidesigner.beta.invitrogen.com/rnaiexpress/.
Bredt, et al., (1990) "Isolation of nitric oxide synthetase, a calmodulin-requiring enzyme", *Proc Natl Acad Sci USA*, 87:682-685.
Brunet, et al. (1991) "Identification of a peptide specific for Aplysia sensory neurons by PCR-based differential screening", *Science*, 252:856-859.
Brunet, et al. (1991) GenBank Accession No. X56770 for A.californica psc 1 mRNA for sensorin A.
Byrne, et al., (1996) "Presynaptic facilitation revisited: state and time dependence", *J Neurosci.*, 16:425-435.
Cha, et al., (2001) "Tyrosine-phosphorylated extracellular signalregulated kinase associates with the Golgi complex during G2/M phase of the cell cycle: evidence for regulation of Golgi structure", *J Cell Biol.*, 153:1355-1367.
Chain, et al. (1999) "Mechanisms for generating the autonomous cAMP-dependent protein kinase required for long-term facilitation in Aplysia", *Neuron*, 22:147-156.
Christensen, et al., (2006) "Cyclic GMP-dependent protein kinase Ialpha inhibits thrombin receptor-mediated calcium mobilization in vascular smooth muscle cells", *J. Biol. Chem.*, 281(13):8409-8416.
Clatworthy, et al., (1999) "Immune-mediated alterations in nociceptive sensory function in Aplysia californica", *J Exp Biol.*, 202:623-630.
Clatworthy, et al., (1995) "Role of peri-axonal inflammation in the development of thermal hyperalgesia and guarding behavior in a rat model of neuropathic pain", *Neurosci Lett.*, 184:5-8.
Collins, et al., (1999) GenBank Accession No. AF084547 (AAC16044) for cGMP-dependent protein kinase type Ib [Mus musculus].
Crown, et al., (2005) "Upregulation of the phosphorylated form of CREB in spinothalamic tract cells following spinal cord injury: relation to central neuropathic pain", *Neurosci Lett.*, 384:139-144.
Dagan, et al., (1981) "Isolated identified Aplysia neurons in cell culture", *J Neurosci.*, 1:736-740.
Dale, et al., (1988) "Long-term facilitation in Aplaysia involves increase in transmitter release", *Science*, 239:282-285.
Dash, et al., (1998) "Sequestration of cAMP response element-binding proteins by transcription factor decoys causes collateral elaboration of regenerating Aplysia motor neuron axons", *Proc Natl Acad Sci USA*, 95:8339-8344.
DesGroseillers, et al., (1994) "A novel actin cDNA is expressed in the neurons of Aplysia californica", *Biochim Biophys Acta.*, 1217:322-324.
DesGroseillers, et al. (1994) GenBank Accession No. U01352 for Aplysia californica actin mRNA, complete cds.
Dostmann, et al., (2000) "Highly specific, membrane-permeant peptide blockers of cGMP-dependent protein kinase I alpha inhibit NO-induced cerebral dilation", *Proc Natl Acad Sci USA*, 97(26):14772-7.
Donward, Julian (2004) Science, medicine, and the future. RNA Interference. *BJM*, 328:1245-1248.
Elbashir, et al., (2001) "Duplexes of 21-nucleotide RNAs mediated RNA interference in cultured mammalian cells", *Nature*, 411: 494-498.
Elbashir, et al., (2002) "Analysis of gene function in somatic mammalian cells using small interfering RNAS", *Methods*, 26: 199-213.
Farr, et al., (1999) "Inflammation causes a long-term hyperexcitability in the nociceptive sensory neurons of Aplysia", *Learn Mem.*, 6:331-340.
Farr et al., (2001) "Direct interactions between immunocytes and neurons after axotomy in Aplysia", *J Neurobiol.*, 46:89-96.
Fiallos-Estrada, et al. (1993) "Long-lasting increase of nitric oxide synthetase immunoreactivity, NADPH-diaphorase reaction and c-JUN co-expression in rat dorsal root ganglion neurons following sciatic nerve transection", *Neurosci Lett.*, 150:169-173.
Fire, et al., (1998) "Potent and specific genetic interference by double-stranded RNA in *Caenorhabditis elegans*", *Nature*, 391: 806-811.
Foster, et al., (1996) GenBank Accession No. AAB03405 for cGMP-dependent protein kinase [*Drosophila melanogaster*].
Francis, et al., (1994) "Structure and function of cyclic nucleotidedependent protein kinases", *Annu Rev Physiol.*, 56:237-272.
Gewirtz, et al., (1996) "Facilitating oligonucleotide delivery: Helping antisense deliver on its promise", *Proc. Natl. Acad. Sci. USA*, 93: 3161-3163.
Ghirardi, et al., (1992) Roles of PKA and PKC in facilitation of evoked and spontaneous transmitter release at depressed and nondepressed synapses in Aplysia sensory neurons. *Neuron*, 9:479-489.
Glanzman, et al., (1989) "Identified target motor neuron regulates neurite outgrowth and synapse formation of Aplysia sensory neurons in vitro", *Neuron*, 3:441-450.
Glass, et al., (1982) "Phosphorylation by guanosine 3':5'-monophosphate-dependent protein kinase of synthetic peptide analogs of a site phosphorylated in histone H2B", *J Biol Chem.*, 257:1196-1200.
Goldsmith, et al., (1992) "cAMP modulates multiple K+ currents, increasing spike duration and excitability in Aplysia sensory neurons", *Proc Natl Acad Sci USA*, 89:11481-11485.
Griffiths, et al.,(2003) "A new and simple method for delivering clamped nitric oxide concentrations in the physiological range: application to activation of guanylyl cyclase-coupled nitric oxide receptors", *Mol Pharmacol.* 64(6):1349-56.
Gudi, et al., (1997) "Regulation of gene expression by cyclic GMP-dependent protein kinase requires nuclear translocation of the kinase: identification of a nuclear localization signal", *Mol Cell Biol.*, 17:5244-5254.
Hall, et al., (1999) "Phosphorylation-dependent inhibition of protein phosphatase-I by G-substrate. A Purkinje cell substrate of the cyclic GMP-dependent protein kinase", *J Biol Chem.*, 274:3485-3495.
Hammond, et al., (2001) "Post-Transcriptional Gene Silencing by Double Stranded RNA", *Nature Genetics*, 2: 110-119.
Hanz, et al., (2003) "Axoplasmic importins enable retrograde injury signaling in lesioned nerve", *Neuron*, 40:1095-1104.
Jarchau, et al.,(2005) GenBank Accession No. CAA85284 for cGMP dependent protein kinase II [*Rattus norvegicus*].
Ji, et al., (2001) "Neuronal plasticity and signal transduction in nociceptive neurons: implications for the initiation and maintenance of pathological pain", *Neurobiol Dis.*, 8:1-10.
Johanson, et al., (1995) "Retrograde axonal transport of signal transduction proteins in rat sciatic nerve", *Brain Res*, 690:55-63.
Kalderon, et al. (1993) GenBank Accession No. AAA28459 for cGMP-dependent protein kinase.

(56) References Cited

OTHER PUBLICATIONS

Karin, M. (1994) "Signal transduction from the cell surface to the nucleus through the phosphorylation of transcription factors", *Curr Opin Cell Biol*, 6:415-424.
Krieg, et al., (2004) "Peptide blockers of PKG inhibit ROS generation by acetylcholine and bradykinin in cardiornyocytes but fail to block protection in the whole heart", *Am. J. Physiol. Heart. Circ, Physiol*, 288:H1976-H1981.
Koesling, et al., (2004) "Nitric oxide-sensitive guanylyl cyclase: structure and regulation", *Neurochem Intl.*, 45:813-819.
Kotera, et al., (2003) "cGMP-dependent protein kinase protects cGMP from hyfrolysis by phosphodiesterase-5", *Biochem, J.*, 372(pt. 2): 419-26.
Lampe, et al., "Total Synthesis of (−)-and (+)-balanol", *Journal of Organic Chemistry*, 61(14):4572-4581 (1996).
Lewin, et al., (1999) "Cyclic GMP pathway is critical for inducing long-term sensitization of nociceptive sensory neurons", *Nature Neuroscience, Nature America, Inc.*, 2(1): 18-23.
Liao, et al., (1999) "Activation of protein kinase A contributes to the expression but not the induction of long-term hyperexcitability caused by axotomy of Aplysia sensory neurons", *J Neurosci.*, 19:1247-1256.
Lu, et al., "Delivering siRNA in vivo for functional genomics and novel therapeutics", RNA Interference Technology (Cambridge, appasani, ed., pp. 303-317).
Manjeet, et al., (1999) "Quercetin inhibits LPS-induced nitric oxide and tumor necrosis factor-alpha production in murine macrophages", *Int. J. Immunopharmacol*, 21(7): 435-43.
Marais, et al. (1993) "The SRF accessory protein Elk-1 contains a growth factor-regulated transcriptional activation domain", *Cell*, 73:381-393.
Martin, et al, (1997) "MAP kinase translocates into the nucleus of the presynaptic cell and is required for long-term facilitation in Aplysia", *Neuron.*, 18(6):899-912.
The Merck Manual of Diagnosis and Therapy, Section 14, Chapter 165, Figure 165-2, which references Keegan JJ and Garrett FD, Anatomical Record 102:409-437, 1948, used with permission of the Wistar Institute, Philadelphia, PA.
Michael, et al., (1998) "Repeated pulses of serotonin required for long-term facilitation activate mitogen-activated protein kinase in sensory neurons of Aplysia", *Proc Natl Acad Sci USA*, 95:1864-1869.
Mo, et al., (2004) "Kinetics of a cellular nitric oxide/cGMP/phosphodiesterase-5 pathway", *J Biol Chem.* 279(25):26149-58.
Monfort, et al., (2002) "Long-term potentiation in hippocampus involves sequential activation of soluble guanylate cyclase, cGMP-dependent protein kinase, and cGMP-degrading phosphodiesterase", *J Neurosci*, 22:10116-10122.
Moroz, et al (1996) "Nitric oxide synthase activity in the molluscan CNS", *J Neurochem*, 66:873-876.
Muller, et al., (1998) "Serotonin induces temporally and mechanistically distinct phases of persistent PKA activity in Aplysia sensory neurons" *Neuron*, 21:1423-1434.
Nielsen (2005) "The last hurdle?", *Gene Therapy*, 12:956-957.
Okada, et al., (2002) "Allosteric activation of cGMP-specific, cGMP-binding phosphosdiesterase (PDES) by cGMP", Biochem., J., 41(30): 9672-9.
Ostravik, et al., (2005) GenBank Accession No. CAA64318 for Type II cGMP-dependent protein kinase [Homo sapiens].
Pohler, et al. (1995) "Expression, purification, and characterization of the cGMP-dependent protein kinases I_and II using the baculovirus system", *FEBS Lett*, 374:419-425.

Sadreyev, et al., (2001) GenBank Accession No. AAK83069 for nitric oxide synthase [*Aplysia californica*].
Sung, et al., (2004) "Pathways that elicit long-term changes in gene expression in nociceptive neurons following nerve injury: contributions to neuropathic pain", *Neurol Res*, 26:195-203.
Sung, et al., (2004) "A neuronal isoform of protein kinase G couples mitogen-activated protein kinase nuclear import to axotomy-induced long-term hyperexcitability in Aplysia sensory neurons", *J. Neurosci.*, 24(34):7583-7595.
Sung, et al., (2003) "The fragile X mental retardation protein FMRP binds elongation factor 1A mRNA and negatively regulates its translation in vivo", *J Biol Chem.*, 278:15669-15678.
Sung, et al., (1996) "The dominant negative effects of H-Ras harboring a Gly to Ala mutation at position 60", *J Biol Chem*, 271:30537-30543.
Sung, et al., (2000) "RNAs that interact with the fragile X syndrome RNA binding protein FMRP", *Biochem Biophys Res Commun.*, 275:973-980.
Sutton, et al., (2000) "Parallel molecular pathways mediate expression of distinct forms of intermediate-term facilitation at tail sensory motor synapses in Aplysia", *Neuron*, 26:219-231.
Tamura, et al., (1999) GenBank Accession No. BAA08297 for cGMP-dependent protein kinase type I alpha [Homo sapiens].
Tischkau, et al., (2003) "Circadian Clock-Controlled Regulation of cGMP-Protein Kinase G in the Nocturnal Domain", *The Journal of Neuroscience*, 23: 7543-7550.
Uhler, et al. (1993) GenBank Accession No. AAA02572 for cyclic GMP-dependent protein kinase II.
Verge, et al., (1992) "Marked increase in nitric oxide synthase mRNA in rat dorsal root ganglia after peripheral axotomy: in situ hybridization and functional studies", *Proc Natl Acad Sci USA*, 89:11617-11621.
Walters, E.T. (1994) "Injury-related behavior and neuronal plasticity: an evolutionary perspective on sensitization, hyperalgesia, and analgesia", *Int Rev Neurobiol*, 36:325-427.
Whitmarsh, et al., (1995) "Integration of MAP kinase signal transduction pathways at the serum response element", *Science*, 269:403-407.
Xu, et al., (1995) "MEKK1 phosphorylates MEK1 and MEK2 but does not cause activation of mitogenactivated protein kinase", *Proc Natl Acad Sci USA*, 92:6808-6812.
Yang, et al., (2002) "Felodipine inhibits nuclear translocation of p42/44 mitogen-activated protein kinase and human smooth muscle growth", *Cardiovasc Res*, 53:227-231.
Yao, et al., (2000) "Detection of partially phosphorylated forms of ERK by monoclonal antibodies reveals spatial regulation of ERK activity by phosphatases", *FEBS Lett*, 468:37-42.
Zaragoza, et al., (2002) "Activation of the mitogen activated protein kinase extracellular signal-regulated kinase 1 and 2 by the nitric oxide-cGMP-cGMPdependent protein kinase axis regulates the expression of matrix metalloproteinase 13 in vascular endothelial cells", *Mol Pharmacol*, 62:927-935.
Zhang, et al., (1993) "Nitric oxide synthase-like immunoreactivity in lumbar dorsal root ganglia and spinal cord of rat and monkey and effect of peripheral axotomy", *J Comp Neural*, 335:563-575.
Zhou, et al., (2002) "The activity of the extracellular signal-regulated kinase 2 is regulated by the differential phosphorylation in the activation loop", *J. Biol Chem*, 277:13889-13899.
Zimmermann, M. (2001) "Pathobiology of neuropathic pain", *Eur J Pharmacol*, 429:23-37.
Partial European Search Report for EP06748487, dated Dec. 12, 2011.

* cited by examiner

```
apPKG  228 ASYKAVTHTT-LWVLDRRVFQAIMMKTGLQRREENMAFLKSVPLLKNLPSDKLAKMSDVLEYDFFHENEYIIREGAAGDTFFILNKGEVKVTQKI
DG1    261 ASIRVLSEAARVWVLDRRVFQQIMMCTGLQRIENSVNFLRSVPLLMNLSEELLAKIADVLELEFYAAGTYIIRQGTAGDSFFLISQGNVRVTQKL
hPKG1a 179 ATVKTLVNVK-LWAIDRQCFQTIMMRTGLIKHTEYMEFLKSVPTFQSLPEEILSKLADVLEETHYENGEYIIRQRARGDTFFIISKGTVNVTRED
mPKG1b 194 ATVKTLVNVK-LWAIDRQCFQTIMMRTGLIKHTEYMEFLKSVPTFQSLPDEILSKLADVLEETHYENGEYIIRQRARGDTFFIISKGQVNVTRED
DG2T3A 250 ATITAITECN-LWAIERQCFQTIMMRTGLIRQAEYSDFLKSVPIFKDLAEDTLIKISDVLEETHYQRGDHIVRQGARGDTFFIISKGKVRVTIKQ
hPKGII 244 ASYKAITNVK-TWALDREVFQNIMRRTAQARDEQYRNFLRSVSLLKNLPEDKLTKIIDCLEVEYYDKGDYIIREGEEGSTFFILAKGKVKVTQST
mPKGII 244 ASYKAITNVK-TWALDREVFQNIMRRTAQARDEEYRNFLRSVSLLKNLPEDKLTKIIDCLEVEYYDKGDYIIREGEEGSTFFILAKGKVKVTQST apPKG  322 AGHA-EPKEVRRLKRGDYFGEKALLSEDRRTANVIALPP-GVECLTVDRESFTQFVGDLNELR--------NKDYGDEARGAERRSG------SD    SEQ ID NO: 11
DG1    356 TPTSPEETELRTILSRGDYFGEQALINEDKRTANIIALSP-GVECLTLDRDSFKRLIGDLCELK--------EKDYGDESRKLAMKQA------RE    SEQ ID NO: 12
hPKG1a 273 SPSE-DPVFLRTLGKGDWFGEKALQGEDVRTANVIAAEA--VTCLVIDRDSFKHLIGGLDDVS---------NKAYEDAEAKAKYEA--------    SEQ ID NO: 13
mPKG1b 288 SPSE-DPVFLRTLGKGDWFGEKALQGEDVRTANVIAAEA--VTCLVIDRDSFKHLIGGLDDVS---------NKAYEDAEAKAKYEA--------    SEQ ID NO: 14
DG2T3A 344 QDRQ-EEKFIRMLGKGDFFGEYFGEKALQGDDLRTANIICESADGVSCLVIDRETFNQLISNLDEIK------HR-YDDEG-AMERRK-------    SEQ ID NO: 15
hPKGII 338 EGHD-QPQLIKTLQKGEYFGEKALISDDVRSANIIAEEN-DVACLVIDRETFNQTVGTFEELQKYLEGYVANLNRDDEKRHAKRSMSNWKLSKAL    SEQ ID NO: 16
mPKGII 338 EGHD-QPQLIKTLQKGEYFGEKALISDDVRSANIIAEEN-DVACLVIDRETFNQTVGTFDELQKYLEGYVATLNRDDEKRHAKRSMSSWKLSKAL    SEQ ID NO: 17 apPKG  401 STVSPVSERPVAKEFENCSLDDLQLVTTLGMGGFGRVELVQLS-KEKGKTFALKCLKKHIVETRQQEHIYSEKKIMMEADSPFITKLHKTFRDR
DG1    346 SCQDEPREQ-LQQEFPDLKLTDLEVSTLGIGGFGRVELVKAHHQDRVDIFALKCLKKRHIFSERHIMLSSRSPFICRLYRTFRDE
hPKG1a 348 ----------EAAFFANLKLSDFNIIDTLGVGGFGRVELVQLK-SEESKTFAMKILKKRHIVDTRQQEHIRSEKQIMQGAHSDFIVRLYRTFKDS
mPKG1b 363 ----------EAAFFANLKLSDFNIIDTLGVGGFGRVELVQLK-SEESKTFAMKILKKRHIVDTRQQEHIRSEKQIMQGAHSDFIVRLYRTFKDS
DG2T3A 419 ----------INEEFRDINLTDLRVIATLGVGGFGRVELVQTN-GDSSRSFALKQMKKSQIVETRQQHIMSEKEIMGEANCQFIVKLFKTFKDK
hPKGII 431 SLEMIQLKEKVARFSSSSPFQNLEIIATLGVGGFGRVELVKVK--NENVAFAMKCIRKKHIVDTKQQEHVYSEKRILEELCSPFIVKLYRTFKDN
mPKGII 431 SLEMIQLKEKVARFSSTSPFQNLEIIATLGVGGFGRVELVKVK--NENIAFAMKCIRKKHIVDTKQQEHVYSEKRILEELCSPFIVKLYRTFKDN
```

FIG. 1B

```
apPKG  495  KYVYYMLMEVCLGGELWTILRDRGNFDDLTARFCVACVLEAFSYLHAKGIIYRDLKPENILLLDARGYVKLVDFGFAKKIGVGKKTWTFCGTPEYVA
DG1    530  KYVYYMLLEACMGGEIWTMLRDRGSFEDNAAQFIIGCVLQAFEYLHARGIIYRDLKPENLMLDERGYVKIVDFGFAKQIGTSSKTWTFCGTPEYVA
hPKG1a 432  KYLYMLMEACLGGELWTILRDRGSFEDSTTRFYTACVVEAFAYLHSKGIIYRDLKPENLILDHRGYAKLVDFGFAKKIGFGKKTWTFCGTPEYVA
mPKG1b 447  KYLYMLMEACLGGELWTILRDRGSFEDSTTRFYTACVVEAFAYLHSKGIIYRDLKPENLILDHRGYAKLVDFGFAKKIGFGKKTWTFCGTPEYVA
DG2T3A 503  KYLYMLMESCLGGELWTILRDKGNFDDSTTRFYTACVVEAFDYLHSRNIIYRDLKPENLLNERGYGKLVDFGFAKKLQTGRKTWTFCGTPEYVA
hPKGII 524  KYVYMLLEACLGGELWSILRDRGSFDEPTSKFCVACVTEAFDYLHRLGIIYRDLKPENLILDAEGYLKLVDFGFAKKIGSGQKTWTFCGTPEYVA
mPKGII 524  KYVYYMLLEACLGGELWSILRDRGSFDEPTSKFCVACVTEAFDYLHRLGIIYRDLKPENLILDADGYLKLVDFGFAKKIGSGQKTWTFCGTPEYVA apPKG  590  PEIILNKGHDHSADYWSLGILMYELLNGTPPFSGSDPMRTYNIILKGIDHIEFPKKISRSAHVLIKKLCRDNPMERLGYGKNGISDIRKNKWFQG
DG1    625  PEIILNKGHDRAVDYWALGILIHELLNGTPPFSAPDPMQTYNLILKGIDMIAFPKHISRWAVQLIKRLCRDVPSERLGYQTGGIQDIKKHKWFLG
hPKG1a 527  PEIILNKGHDISADYWSLGLGILMYELLTGSPPFSGPDPMKTYNIILRGIDMIEFPKKIAKNAANLIKKLCRDNPSERLGNLKNGVKDIQKHKWFEG
mPKG1b 542  PEIILNKGHDISADYWSLGLGILMYELLTGSPPFSGPDPMKTYNIILRGIDMIEFPKKIAKNAANLIKKLCRDNPSERLGNLKNGVKDIQKHKWFEG
DG2T3A 598  PEVILNRGHDISADYWSLGVLMFELLTGTPPFTGSDPMRTYNIILKGIDAIEFPRNITRNASNLIKKLCRDNPAERLGYQRGGISEIQKHKWFDG
hPKGII 619  PEVILNKGHDFSVDFWSLGILVYELLTGNPPFSGVDQMMTYNLILKGIEKMDFPRKITRRPEDLIRRLCRQNPTERLGNLKNGINDIKKHRWLNG
mPKGII 619  PEVILNKGHDFSVDFWSLGILVYELLTGNPPFSGIDQMMTYNLILKGIEKMDFPRKITRRPEDLIRRLCRQNPTERLGNLKNGINDIKKHRWLNG apPKG  685  FDWDGLMDLTLTPPIVPKVKNPTDTSNFDSYPRDMD-IAADELSGWDIDF      SEQ ID NO: 11
DG1    720  FDWDGLASQLLIPPFVRPIAHPTDVRYFDRFPCDLN-EPPDELSGWDADF      SEQ ID NO: 12
hPKG1a 622  FNWEGLRKGTLTPPIIPSVASPTDTSNFDSFPEDNDEPPPDDNSGWDIDF      SEQ ID NO: 13
mPKG1b 637  FNWEGLRKGTLTPPIIPSVASPTDTSNFDSFPEDSDEPPPDDNSGWDIDF      SEQ ID NO: 14
DG2T3A 693  FYWGLQNCTLEPPIKPAVKSVVDTTNFDDYPPDPEGPPPDDVTGWDKDF       SEQ ID NO: 15
hPKGII 714  FNWEGLKARSLPSPLQRELKGPIDHSYFDKYPPEKG-MPPDELSGWDKDF      SEQ ID NO: 16
mPKGII 714  FNWEGLKARSLPSPLRRELSGPIDHSYFDKYPPEKG-VPPDEMSGWDKDF      SEQ ID NO: 17
```

FIG. 1C

Balanol docked into PKG homology model

X-ray structure of balanol in PKA

| Structure | Compound No. | Formula | Mol Weight | Source | XP GlideScore (method) |
|---|---|---|---|---|---|
| 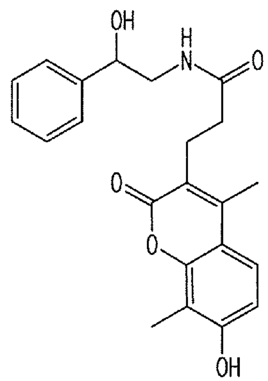 | 180611 | C22H23NO5 | 381.422 | InterBio: STOCK1N-61532 | -13.12 (Method A using homology model generated from 1bx6) |

| Structure | Compound No. | Formula | Mol Weight | Source | XP GlideScore (method) |
|---|---|---|---|---|---|
| 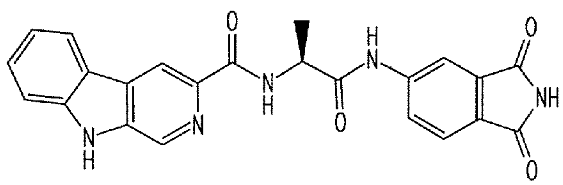 | 181613 | C23H17N5O4 | 427.412 | InterBio: STOCK1N-62536 | -12.91 (Method A using homology model generated from 1bx6) |

| Structure | Compound No. | Formula | Mol Weight | Source | XP GlideScore (method) |
|---|---|---|---|---|---|
| (structure image) | 224571 | C24H18N2O3S | 414.476 | ChemStar: CHS 1682453 TimTec: ST034073 | −12.83 (Method A using homology model generated from 1bx6) |

FIG. 8E

| Structure | Compound No. | Formula | Mol Weight | Source | XP GlideScore (method) |
|---|---|---|---|---|---|
| (structure image) | 311286 | C21H17N3O3S | 391.443 | Asinex Platinum: ASN 01890485 | −12.21 (Method A using homology model generated from 1bx6) |

FIG. 8F

| Structure | Compound No. | Formula | Mol Weight | Source | XP GlideScore (method) |
|---|---|---|---|---|---|
| 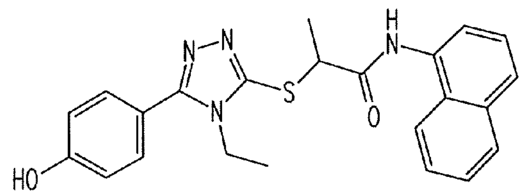 | 312672 | C23H22N4O2S | 418.511 | Asinex Platinum: ASN 02070237 | −12.69 (Method A using homology model generated from 1bx6) |

| Structure | Compound No. | Formula | Mol Weight | Source | XP GlideScore (method) |
|---|---|---|---|---|---|
| 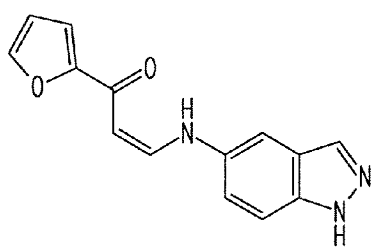 | NOP479435 | C14H11N3O2 | 253.256 | Asinex Gold: BAS 00656320 | −12.25 (Method A using homology model generated from 1sve) |

Bound to Balanol

Bound to Compound 8C

Bound to Compound 8D

Bound to Compound 8E

Bound to Compound 8F

Bound to Compound 8G

Bound to Compound 8H

Bound to Compound 8I

Bound to Compound 8J

Bound to Compound 8K

Bound to Compound 8L

| Linker Code | PKG Phenol Rank | PKA Phenol Rank | PKG vs. PKA Phenol Rank | PKG Indazole Rank | PKA Indazole Rank | PKG vs. PKA Indazole Rank | Indazole vs. Phenol Rank |
|---|---|---|---|---|---|---|---|
| Compound 6 | 10 | 3 | 134 | 4 | 17 | 67 | 46 |
| A1 | 46 | 54 | 65 | 23 | 66 | 32 | 49 |
| A2 | 24 | 37 | 76 | 53 | 74 | 54 | 103 |
| A3 | 34 | 22 | 121 | 103 | 46 | 138 | 141 |
| A4 | 73 | 49 | 106 | 27 | 14 | 114 | 26 |
| A5 | 57 | 108 | 25 | 80 | 113 | 44 | 91 |
| A6 | 94 | 61 | 108 | 133 | 107 | 127 | 137 |
| A7 | 7 | 23 | 84 | 45 | 7 | 136 | 113 |
| A8 | 81 | 35 | 132 | 62 | 57 | 85 | 54 |
| A9 | 12 | 28 | 70 | 8 | 26 | 37 | 51 |
| A10 | 82 | 15 | 150 | 130 | 1 | 156 | 138 |
| A11 | 86 | 64 | 94 | 131 | 72 | 145 | 139 |
| A12 | 6 | 92 | 10 | 116 | 35 | 149 | 152 |
| A13 | 61 | 87 | 44 | 81 | 93 | 71 | 88 |
| A14 | 95 | 42 | 138 | 113 | 88 | 115 | 105 |
| A15 | 22 | 52 | 40 | 108 | 15 | 152 | 147 |
| A16 | 27 | 53 | 51 | 92 | 58 | 120 | 134 |
| A17 | 52 | 19 | 136 | 70 | 67 | 86 | 89 |
| A18 | 32 | 55 | 55 | 14 | 75 | 22 | 60 |
| A19 | 99 | 91 | 79 | 127 | 124 | 82 | 118 |
| A20 | 14 | 112 | 6 | 97 | 76 | 109 | 146 |
| A21 | 8 | 20 | 97 | 74 | 99 | 52 | 130 |
| A22 | 20 | 46 | 52 | 89 | 64 | 108 | 133 |
| A23 | 76 | 17 | 147 | 95 | 78 | 103 | 101 |
| A24 | 42 | 150 | 1 | 117 | 62 | 140 | 143 |
| A25 | 112 | 133 | 31 | 142 | 135 | 94 | 142 |
| A26 | 15 | 115 | 5 | 82 | 111 | 48 | 131 |
| A27 | 150 | 65 | 152 | 76 | 12 | 144 | 6 |
| A28 | 63 | 132 | 11 | 106 | 98 | 96 | 123 |
| A29 | 92 | 10 | 155 | 105 | 54 | 130 | 97 |
| A30 | 55 | 113 | 18 | 48 | 73 | 50 | 63 |
| A31 | 131 | 56 | 143 | 126 | 116 | 110 | 78 |

FIG.14A

| (Figure 14 Continued) | | | | | | | |
|---|---|---|---|---|---|---|---|
| A32 | 138 | 77 | 133 | 112 | 101 | 98 | 53 |
| | | | | | | | |
| C1 | 26 | 13 | 123 | 20 | 16 | 105 | 70 |
| C2 | 5 | 18 | 91 | 22 | 27 | 73 | 87 |
| C3 | 9 | 11 | 109 | 56 | 33 | 104 | 120 |
| C4 | 11 | 16 | 102 | 13 | 31 | 49 | 72 |
| C4 | 137 | 140 | 54 | 91 | 114 | 65 | 29 |
| C5 | 88 | 110 | 43 | 150 | 131 | 125 | 153 |
| C7 | 47 | 62 | 58 | 129 | 90 | 137 | 149 |
| C8 | 90 | 82 | 80 | 124 | 103 | 117 | 119 |
| | | | | | | | |
| D1 | 64 | 97 | 37 | 138 | 85 | 148 | 150 |
| D2 | 65 | 5 | 153 | 65 | 41 | 100 | 73 |
| D3 | 28 | 27 | 103 | 72 | 32 | 119 | 115 |
| D4 | 121 | 76 | 119 | 16 | 80 | 19 | 4 |
| D5 | 30 | 124 | 9 | 73 | 42 | 107 | 112 |
| D6 | 18 | 7 | 127 | 25 | 94 | 14 | 77 |
| D7 | 48 | 12 | 141 | 15 | 63 | 30 | 45 |
| D8 | 107 | 129 | 34 | 87 | 142 | 7 | 56 |
| D9 | 31 | 69 | 29 | 33 | 104 | 13 | 74 |
| D10 | 41 | 48 | 68 | 94 | 81 | 99 | 124 |
| D11 | 53 | 105 | 21 | 135 | 140 | 59 | 151 |
| D12 | 68 | 33 | 126 | 6 | 70 | 11 | 10 |
| D13 | 113 | 100 | 90 | 120 | 126 | 58 | 90 |
| D14 | 40 | 44 | 81 | 55 | 69 | 69 | 85 |
| D15 | 80 | 51 | 111 | 44 | 59 | 63 | 36 |
| D16 | 44 | 71 | 32 | 71 | 20 | 132 | 100 |
| D17 | 51 | 118 | 13 | 110 | 110 | 88 | 132 |
| D18 | 70 | 34 | 125 | 21 | 44 | 51 | 25 |
| D19 | 67 | 88 | 49 | 28 | 128 | 6 | 32 |
| D20 | 23 | 103 | 12 | 51 | 25 | 106 | 99 |
| D21 | 89 | 66 | 99 | 93 | 106 | 79 | 86 |
| D22 | 2 | 2 | 129 | 26 | 3 | 135 | 107 |
| D23 | 105 | 24 | 151 | 32 | 38 | 75 | 14 |
| D24 | 114 | 6 | 157 | 5 | 5 | 91 | 1 |
| D25 | 149 | 94 | 142 | 63 | 65 | 78 | 3 |
| D26 | 127 | 95 | 114 | 50 | 121 | 10 | 9 |

FIG.14B

| (Figure 14 Continued) | | | | | | | |
|---|---|---|---|---|---|---|---|
| D27 | 17 | 86 | 15 | 134 | 115 | 128 | 155 |
| D28 | 111 | 142 | 20 | 67 | 84 | 60 | 28 |
| D29 | 36 | 25 | 115 | 69 | 22 | 124 | 102 |
| D30 | 72 | 21 | 144 | 96 | 23 | 146 | 106 |
| D31 | 59 | 60 | 78 | 101 | 51 | 131 | 122 |
| D32 | 152 | 130 | 124 | 102 | 134 | 21 | 11 |
| D33 | 133 | 73 | 135 | 111 | 130 | 34 | 55 |
| D34 | 25 | 80 | 19 | 1 | 2 | 47 | 8 |
| D35 | 33 | 41 | 89 | 18 | 28 | 72 | 59 |
| D36 | 98 | 120 | 38 | 30 | 30 | 83 | 18 |
| D37 | 58 | 90 | 35 | 37 | 47 | 70 | 50 |
| D38 | 38 | 14 | 131 | 24 | 19 | 102 | 58 |
| D39 | 35 | 1 | 156 | 11 | 13 | 93 | 38 |
| D40 | 69 | 146 | 7 | 59 | 117 | 15 | 65 |
| D41 | 115 | 38 | 148 | 19 | 56 | 39 | 7 |
| D42 | 155 | 155 | 36 | 154 | 139 | 143 | 127 |
| D43 | 151 | 156 | 16 | 155 | 146 | 134 | 148 |
| D44 | 144 | 147 | 53 | 141 | 145 | 53 | 111 |
| D45 | 130 | 121 | 86 | 122 | 125 | 62 | 76 |
| D46 | 16 | 39 | 61 | 132 | 120 | 111 | 154 |
| D47 | 60 | 144 | 4 | 153 | 71 | 155 | 156 |
| D48 | 143 | 134 | 74 | 54 | 122 | 12 | 5 |
| D49 | 117 | 127 | 57 | 88 | 45 | 121 | 42 |
| D50 | 132 | 151 | 30 | 114 | 92 | 112 | 57 |
| D51 | 156 | 157 | 17 | 149 | 132 | 122 | 75 |
| D52 | 153 | 136 | 120 | 148 | 143 | 87 | 84 |
| D53 | 142 | 126 | 93 | 137 | 157 | 9 | 98 |
| D54 | 145 | 152 | 39 | 79 | 151 | 3 | 13 |
| D55 | 154 | 107 | 149 | 136 | 34 | 154 | 39 |
| D56 | 119 | 45 | 145 | 157 | 89 | 157 | 157 |
| D57 | 139 | 141 | 47 | 85 | 154 | 2 | 21 |
| D58 | 100 | 143 | 14 | 34 | 141 | 1 | 19 |
| D59 | 1 | 84 | 2 | 3 | 18 | 45 | 81 |
| D60 | 126 | 137 | 56 | 86 | 102 | 66 | 27 |
| D61 | 120 | 135 | 42 | 119 | 36 | 150 | 80 |
| D62 | 157 | 153 | 110 | 156 | 137 | 151 | 140 |

FIG.14C

| (Figure 14 Continued) | | | | | | | |
|---|---|---|---|---|---|---|---|
| P1 | 79 | 59 | 104 | 43 | 95 | 27 | 37 |
| P2 | 39 | 89 | 24 | 104 | 53 | 129 | 136 |
| P4 | 83 | 81 | 69 | 39 | 82 | 31 | 31 |
| P5 | 84 | 78 | 73 | 98 | 40 | 139 | 96 |
| P5 | 124 | 111 | 95 | 145 | 152 | 33 | 129 |
| P6 | 140 | 138 | 62 | 147 | 144 | 77 | 125 |
| P7 | 141 | 148 | 45 | 146 | 156 | 18 | 121 |
| P8 | 134 | 123 | 88 | 140 | 153 | 25 | 117 |
| P9 | 62 | 67 | 63 | 52 | 21 | 118 | 64 |
| P10 | 74 | 96 | 46 | 47 | 109 | 17 | 43 |
| P11 | 66 | 116 | 22 | 123 | 127 | 64 | 135 |
| P12 | 56 | 63 | 67 | 46 | 6 | 141 | 62 |
| P13 | 118 | 122 | 64 | 78 | 147 | 5 | 34 |
| P14 | 93 | 57 | 112 | 31 | 52 | 55 | 20 |
| P16 | 37 | 36 | 96 | 9 | 10 | 84 | 24 |
| P17 | 75 | 83 | 60 | 49 | 60 | 68 | 44 |
| P17 | 122 | 106 | 100 | 57 | 91 | 43 | 16 |
| P18 | 110 | 125 | 50 | 118 | 108 | 101 | 93 |
| P19 | 125 | 149 | 28 | 152 | 149 | 80 | 144 |
| P20 | 129 | 139 | 48 | 143 | 150 | 41 | 126 |
| P21 | 104 | 101 | 75 | 58 | 112 | 24 | 30 |
| P22 | 135 | 79 | 130 | 83 | 118 | 35 | 22 |
| P23 | 78 | 68 | 77 | 90 | 97 | 74 | 82 |
| P24 | 85 | 9 | 154 | 75 | 68 | 89 | 66 |
| | | | | | | | |
| X1 | 136 | 117 | 98 | 139 | 148 | 29 | 109 |
| X2 | 116 | 114 | 71 | 115 | 129 | 38 | 79 |
| X3 | 123 | 145 | 27 | 151 | 96 | 153 | 145 |
| X4 | 96 | 154 | 8 | 121 | 83 | 123 | 114 |
| | | | | | | | |
| Z1 | 49 | 99 | 23 | 36 | 86 | 28 | 67 |
| Z2 | 50 | 43 | 92 | 42 | 43 | 76 | 71 |
| Z3 | 97 | 85 | 85 | 125 | 138 | 36 | 116 |
| Z4 | 101 | 58 | 118 | 61 | 48 | 92 | 35 |
| Z5 | 29 | 70 | 26 | 10 | 37 | 40 | 41 |
| Z6 | 13 | 32 | 66 | 38 | 24 | 95 | 104 |
| Z7 | 103 | 29 | 146 | 84 | 87 | 81 | 61 |

FIG.14D

| (Figure 14 Continued) | | | | | | | |
|---|---|---|---|---|---|---|---|
| Z8 | 45 | 30 | 107 | 68 | 119 | 16 | 94 |
| Z9 | 91 | 75 | 87 | 100 | 77 | 113 | 95 |
| Z10 | 21 | 4 | 140 | 41 | 61 | 61 | 92 |
| Z11 | 106 | 47 | 139 | 109 | 29 | 147 | 83 |
| Z12 | 102 | 74 | 101 | 77 | 105 | 46 | 47 |
| Z13 | 128 | 98 | 113 | 17 | 50 | 42 | 2 |
| Z14 | 4 | 31 | 59 | 2 | 9 | 23 | 15 |
| Z15 | 19 | 8 | 128 | 7 | 39 | 26 | 40 |
| Z16 | 147 | 128 | 105 | 99 | 155 | 4 | 23 |
| Z17 | 54 | 50 | 82 | 29 | 49 | 57 | 48 |
| Z18 | 108 | 102 | 83 | 40 | 100 | 20 | 17 |
| Z19 | 146 | 93 | 137 | 107 | 55 | 133 | 33 |
| Z20 | 87 | 109 | 41 | 66 | 133 | 8 | 52 |
| Z21 | 77 | 72 | 72 | 12 | 4 | 116 | 12 |
| Z22 | 148 | 119 | 116 | 144 | 136 | 97 | 108 |
| Z23 | 71 | 40 | 122 | 64 | 11 | 142 | 68 |
| Z24 | 3 | 104 | 3 | 60 | 79 | 56 | 128 |
| Z25 | 43 | 26 | 117 | 35 | 8 | 126 | 69 |
| Z26 | 109 | 131 | 33 | 128 | 123 | 90 | 110 |

FIG.14E

Series B Compounds Continued
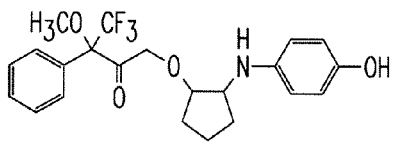
Balanol-9
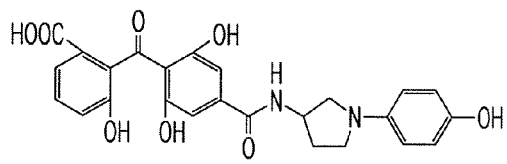
Balanol-10
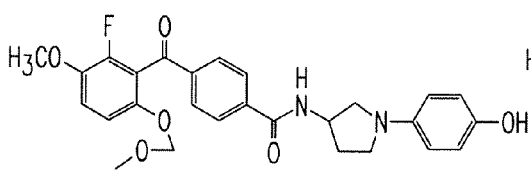
Balanol-11
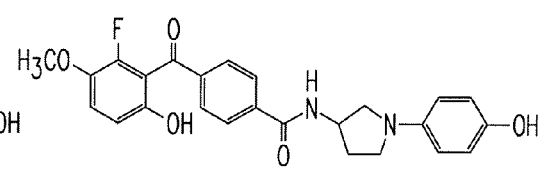
Balanol-12
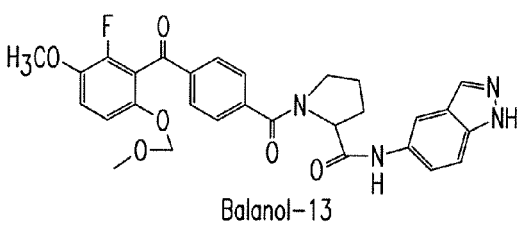
Balanol-13
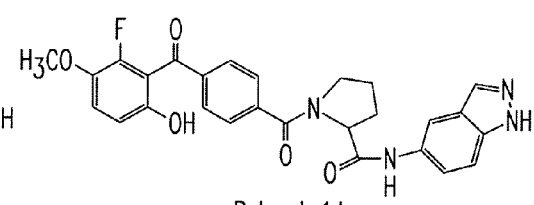
Balanol-14
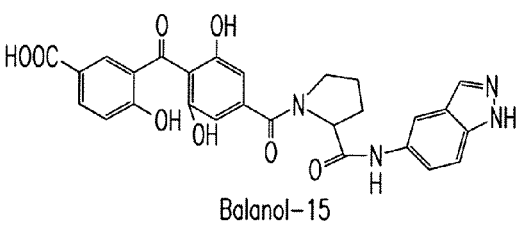
Balanol-15
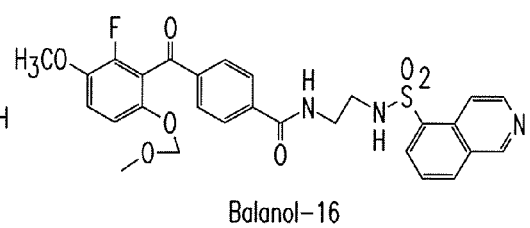
Balanol-16
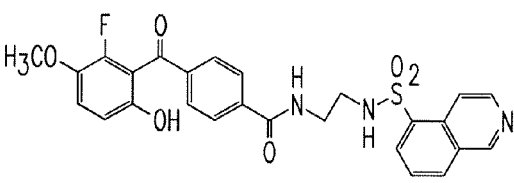
Balanol-17
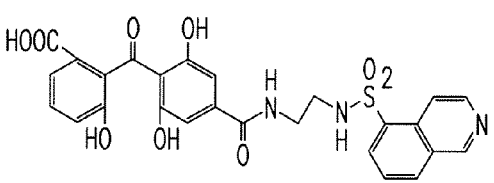
Balanol-18
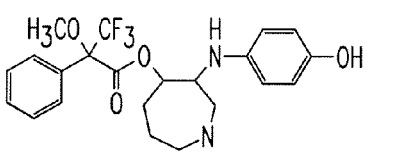
Balanol-19 (R,R)
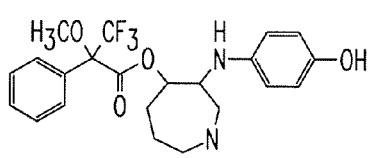
Balanol-20 (R,S)
FIG. 20B-2

Compound 6

Compound 46

NEURONAL PAIN PATHWAY MODULATORS

CROSS-REFERENCE TO RELATED APPLICATIONS

This application claims priority under 35 U.S.C. §119, based on U.S. Provisional Application Ser. No. 60/773,691, filed Feb. 14, 2006, and U.S. Provisional Application Ser. No. 60/815,980, filed Jun. 23, 2006. The teachings of these referenced applications are incorporated herein by reference in their entireties.

GRANT INFORMATION

The subject matter of this application was developed at least in part under National Institutes of Health Grants NS12250 and NS35979, so that the United States Government has certain rights herein.

1. INTRODUCTION

The present invention relates to compounds that inhibit the activated form of protein kinase G ("PKG") and their use in the alleviation of pain, particularly in the context of chronic pain syndromes.

2. BACKGROUND OF THE INVENTION

Pain is perceived as a result of communication between the two main divisions-central and peripheral—of the nervous system. While the two divisions work together to produce our subjective experience, the central and peripheral nervous systems are anatomically and functionally different.

A painful stimulus impinging on a specialized pain receptor is propagated along a peripheral branch of a primary nociceptive sensory neuron whose cell body resides within a dorsal root ganglion (part of the peripheral nervous system) and then along a central branch of the neuron that enters the spinal cord (central nervous system). The signal is subsequently relayed to a second order neuron in the spinal cord that, in turn, transmits the signal to the opposite ("contralateral") side of the spinal cord. The signal is then communicated to higher centers in the brain where it is perceived as painful.

Peripheral pain receptors, which respond to mechanical, thermal or chemical stimuli are located on nerve endings of the primary nociceptive neurons. Activation of these receptors results in pain that can be acute or chronic. Acute pain tends to be sharp and well-localized and is typically transmitted along the thinly myelinated axons of A delta sensory neurons. Chronic pain is usually dull and diffuse, and is conveyed along non-myelinated axons of C-type nociceptive neurons. Chemical mediators of inflammation such as bradykinin and prostaglandins stimulate pain receptors, and are important agents in chronic pain syndromes, such as the persistent pain associated with arthritis, ileitis or cystitis, to name but a few.

The perception of pain can be altered at various stages of the pain pathway. For example, administering a local anesthetic to the peripheral receptor can eliminate the painful stimulus. Drugs like opioids were classically known to intervene at the central nervous system stage of the pain pathway, and non-steroidal anti-inflammatory drugs at the peripheral stage (although it is now realized that there is some cross-reactivity of both). Likewise, what is perceived as chronic pain (not due to primary spinal cord injury) is typically associated with sensitization of peripheral pain receptors as well as changes in the excitability of the second order neurons, and therefore has both peripheral and central nervous system components. The peripheral and central components regulate "primary" and "secondary" hyperalgesia, respectively (Urban and Gebhart, 1999, citing Woolf, 1983 and La Motte et al., 1991). In secondary hyperalgesia, the second order neuron in the central nervous system undergoes changes in gene expression that contribute to the phenomenon of "central sensitization" or "spinal hyperalgesia". Spinal N-methyl-D-aspartate ("NMDA") receptors are believed to play an important role in this process (Urban and Gebhart, 1999, citing Urban and Gebhart, 1998; Palacek et al., 2003; Lee et al., 1993). Spinal cord injury (presumably) without activation of the peripheral nervous system can also produce spinal hyperalgesia resulting in a central pain syndrome (Zhang et al., 2005). Central neuropathic pain has been associated with phosphorylation of the transcription factor, cyclic AMP response element binding protein ("CREB") (Cron et al., 2005).

Chronic pain is initiated in the periphery by either a nerve injury ("neuropathic pain") or an inflammation and both sources result in pain that is a major clinical problem that has mostly resisted effective treatment. In humans (Gracely et al., 1992) and mammalian model systems (Millan, 1999), persistent pain after nerve injury is associated with long-term hyperexcitability (LTH) of those primary sensory neurons whose axons are in the affected nerve. LTH is manifested as increased sensitivity to electrical stimuli in the nociceptive sensory neuron cell body and axon at the injury site (Wall and Devor, 1983; Study and Kral, 1996; Zhang et al., 1997; Chen and Devor, 1998; Kim et al., 1998; Abdulla and Smith, 2001). These changes result in the discharge of action potentials from sensory neurons at rest or during innocuous stimulation, leading to continuing excitation of higher order neurons in the central nervous system, spinal hyperalgesia and persistent pain. Because the appearance of LTH involves alterations in gene expression (Waxman et al., 1994; Wang et al., 2002; Park et al., 2003), a central question is, how are such changes in the neuron nucleus induced by an injury that occurs far from the cell body? Answering this question has been extremely difficult using the complex mammalian nervous system.

An experimentally favorable alternative is the homogeneous cluster of nociceptive sensory neurons that reside in the bilateral pleural ganglia of the mollusk *Aplysia californica* (Walters et al., 2004). Noxious mechanical stimulation of the body wall (Walters et al., 1983a) or crushing sensory neuron axons in vivo or in vitro elicits an LTH with electrophysiological properties similar to those seen after axotomy of mammalian nociceptive neurons (Walters et al., 1991; Walters, 1994; Ambron et al., 1996; Bedi et al., 1998; Ungless et al., 2002; Sung and Ambron, 2004). The LTH appears after a delay, suggesting that its induction after nerve crush is attributable to a positive molecular injury signal (Walters et al., 1991; Ambron and Walters, 1996; Lin et al., 2003). Two studies support this idea. First, blocking axonal transport after nerve injury in excised nervous systems prevented the appearance of LTH (Gunstream et al., 1995). Second, LTH was induced in noninjured sensory neurons by injecting axoplasm from injured axons (Ambron et al., 1995). LTH was also elicited in the neurons after intrasomatic injection of an ERK (extracellular signal-regulated kinase) member of the MAPK (mitogen-activated protein kinase) family (Sung et al., 2001). Other experiments have suggested that cyclic GMP (cGMP) and PKG (cGMP-dependent protein kinase; protein kinase G)

are probably involved (Lewin and Walters, 1999). However, despite these observations, it was only recently that the signal from the axon was identified.

U.S. Pat. No. 6,476,007 by Tao and Johns ("the '007 patent") relates to a proposed signalling pathway in the central nervous system in which stimulation of an N-methyl-D-aspartate ("NMDA") receptor leads to activation of nitric oxide synthase ("NOS") and production of nitric oxide ("NO"), which then stimulates guanylate cylase ("GC") and the production of cyclic guanoside monophosphate (cGMP), which in turn activates cGMP-dependent protein kinase I ("PKG"). It was observed that administration of the PKG inhibitor Rp-8-[4-chlorophenyl)thio]-cGMPS triethylamine into the central nervous system by intrathecal administration, after the induction of an inflammatory response, produced significant attenuation of acute pain in rats 10 and 60 minutes later. Further, the inventors of the '007 patent noted an upregulation of PKG expression in the lumbar spinal cord 96 hours after noxious stimulation was blocked by administration of a neuronal NOS inhibitor, a soluble GC inhibitor, and a NMDA receptor antagonist.

However, the '007 patent is directed toward the mechanism of inflammatory hyperalgesia in the central nervous system; the role of the peripheral nervous system is not considered. Targeting the pain pathway in the central nervous system suffers from several important disadvantages. First the neuronal circuits in the spinal cord are highly complex and not well understood. Thus, drugs that might be predicted to relieve pain can have the opposite effect. Second, the neurons in the central nervous system are sequestered from the rest of the body by the blood-brain-barrier, which is a formidable obstacle that often prevents many therapeutic drugs from ever reaching their targets. The limited permeability means that treatment of spinal hyperalgesia according to the '007 patent would be problematic. Third, drugs that do penetrate the blood brain barrier have access to the entire central nervous system so that side effects can be severe. In contrast, there is no such barrier in the peripheral nervous system. Moreover, the anatomical disposition of the DRG means that it is possible to target specific populations of primary sensory neurons for treatment. Fourth, pain as a sensation is perceived only when signals from the periphery are communicated to higher centers in the brain. Consequently, since the DRG neurons are the portal for these signals, the present invention offers the advantage of intervening in subjective pain as it first arises. Finally, the 007 patent describes methods to prevent the activation of PKG; it does not address the inhibition of the already activated PKG.

Active PKG has a critical role in the initiation of pain. (See International Patent Application No. PCT/US2006/010107, Publication No. WO2006/102267). Following injury to a peripheral nerve there is an increase in nitric oxide synthase ("NOS") activity that results in increased nitric oxide ("NO") production. The NO activates soluble guanylyl cyclase ("sGC"), thereby increasing levels of cyclic guanosine monophosphate ("cGMP") which results in the activation of protein kinase G ("PKG") in the axons of the C-type and A-delta type nociceptive neurons. The activated PKG is then retrogradely transported from the site of injury along the axon to the neuron cell body, where it phosphorylates mitogen-activated protein kinase-erk ("MAPKerk") (Sung et al., Aug. 25, 2004). The activated MAPKerk then translocates into the cell nucleus, where it modulates expression of the pain-related genes that mediate the appearance of LTH. Since inhibiting PKG attenuates pain and reduces the level of mRNAs for proteins that are involved in nociception, the focus of the present invention relates to modulators of the activated PKG.

Balanol is a known protein kinase C(PKC) inhibitor. Various balanol analogs which inhibit PKC have been previously identified by a retro-synthesis of balanol isolated from *Verticillium balanoides* (Lai et al. 1997). The retro-synthesis of the compound divided the compound into the following three main constituents: a tetrasubstituted benzophenone diacid, a trans-3,4-aminohydroxyperhydroazepine, and a 4-hydroxybenzoic acid. The balanol analogs were then synthesized with replacement of the perhydroazepine moiety. Specifically, Lai compared the activity of the analogs to balanol, the parent compound, and found that the analogs were more isozyme selective, demonstrating more selectivity between PKC and PKA than the parent compound (Lai et al. 1997). Lai concluded that the activity and the selectivity of the compounds was largely related to the conformation of the nonaromatic structural elements of the molecule. Ring size of the pyrrolidine nitrogen was found to greatly affect potency, with five molecules considered to have optimal potency.

While Lai was directed to analog development, the focus on the pyrrolidine ring, while valuable in its findings, is limited. The value of different or additional varying substituents at other ring sites within the compound, and the advantage of PKG selective inhibitory activity, were not considered prior to the present invention.

The prior art has demonstrated some additional compounds that exhibit PKC inhibitory action. For example, U.S. Pat. No. 5,432,198 by Jadgdmann et al. ("the '198 patent) discloses additional balanol analogues with different substituents, wherein the compounds have PKC inhibitory activity. The '198 patent discloses a balanol analogue without a pyrrolidine nitrogen, but instead has a carbon ring up to 7 members. Among other substitutions, the '198 compound also requires an alkyl substituted aromatic ring on the amine end of the compound.

U.S. Pat. No. 5,583,221 by Hu et al. ("the '221 patent") similarly discloses compounds that exhibit PKC inhibitory activity. However, the '221 patent is limited in that it does not cover balanol derivatives or pyrrolidine-containing compounds. U.S. Pat. Nos. 6,376,467 and 6,686,334 by Messing et al. ("the '467 patent" and "the '334 patent", respectively) disclose methods to lessen pain with compounds that are specifically directed to an inhibitor of the ϵ isozyme of PKC. The '334 patent further discloses that the amount of inhibitor contemplated would not significantly inhibit other isozymes of PKC.

Thus, there remains a need in the art for unique compounds capable of selectively inhibiting active PKG in a peripheral nervous system. Inhibition of the active kinase would both prevent its transport from the periphery as well as block its activity in the cell body.

3. SUMMARY OF THE INVENTION

The present invention relates to compounds that may be used to inhibit the activated form of protein kinase G ("PKG"). It is based, at least in part, on the prediction of the tertiary structure of PKG and the identification of molecules that either are predicted to bind to the active site of PKG and/or are analogs of balanol.

In one set of embodiments, the present invention provides for pharmaceutical compositions comprising an effective (inhibitory) amount of these PKG modulator compounds.

In another set of embodiments, the present invention provides for methods of inhibiting PKG activity in a neuron by exposing the neuron to an effective inhibitory concentration of one of the PKG modulator compounds. Preferably, but not by way of limitation, the PKG inhibitor is administered to the peripheral nervous system and the neuron in which PKG activity is inhibited is a peripheral neuron.

In related embodiments, the present invention provides for a method of relieving chronic pain in a subject, comprising administering, to the subject, an effective inhibitory amount of one of the PKG modulator compounds of the invention.

4. BRIEF DESCRIPTION OF THE FIGURES

FIG. 1 provides a schematic diagram of *Aplysia* PKG ("apPKG") showing the position of the conserved tandem cGMP binding domains, the ATP binding and catalytic sites, and the position of an autoinhibitory sequence. Bottom, Clustal W sequence alignment of the predicted apPKG amino acid sequence (SEQ ID NO: 11) with *Drosophila* DG1 (GenBank accession number AAB03405) (SEQ ID NO: 12) and DG2T3a (AAA28459) (SEQ ID NO: 13), human I$\alpha$ (BAA08297) (SEQ ID NO: 14) and II (CAA64318) (SEQ ID NO: 15), mouse I$\beta$ (AAD16044) (SEQ ID NO: 16) and II (AAA02572) (SEQ ID NO: 17), and rat II (CAA85284) (SEQ ID NO: 18) PKGs. Conserved amino acids are shaded in black; similar amino acids are shaded in light gray.

FIGS. 2A-C provide the structure for various balanol compounds. FIG. 2A is balanol-7R. FIG. 2B is 10" deoxybalanol. FIG. 2C is 14" decarboxy balanol.

FIGS. 3A and 3B provide an overview of surface dermatomes. FIG. 3A provides the front view, and FIG. 3B depicts the back view.

FIGS. 4A and 4B show schematic drawings of (A) PKA co-crystallized with balanol and (B) balanol docked to a homology model of PKG.

FIGS. 5A and 5B provide a schematic showing differences in PKA and PKG active sites. In FIG. 5A, balanol is docked into the PKA active site. In FIG. 5B, balanol is docked into the PKG active site.

FIG. 6 provides the structures for cyclopentane analogs of balanol.

FIGS. 7A and 7B provide schematic diagrams of docked poses of (A) compound 8H (NOP47935) and (B) balanol in the active site of the PKG homology model, illustrating the sequence differences between PKG type 1 alpha ($\alpha$) and PKA/PKB/PKC.

FIGS. 8A-8L provide structures of compounds 8A-8L, either identified based on similarity to balanol (8A and 8B) or identified by docking to homology models of PKG (8C-8L).

FIGS. 9A-9K provide schematic depictions of PKG bound to various compounds. FIG. 9A shows PKG bound to balanol. FIG. 9B shows PKG bound to compound 8C. FIG. 9C shows PKG bound to compound 8D. FIG. 9D shows PKG bound to compound 8E. FIG. 9E shows PKG bound to compound 8F. FIG. 9F shows PKG bound to compound 8G. FIG. 9G shows PKG bound to compound 8H. FIG. 9H shows PKG bound to compound 8I. FIG. 9I shows PKG bound to compound 8J. FIG. 9J shows PKG bound to compound 8K. FIG. 9K shows PKG bound to compound 8L.

FIG. 14 summarizes the rankings of structural linkages with respect to PKG and PKA.

FIGS. 15A-15L show Compound 6 with varying linkage structures.

Figure 16:
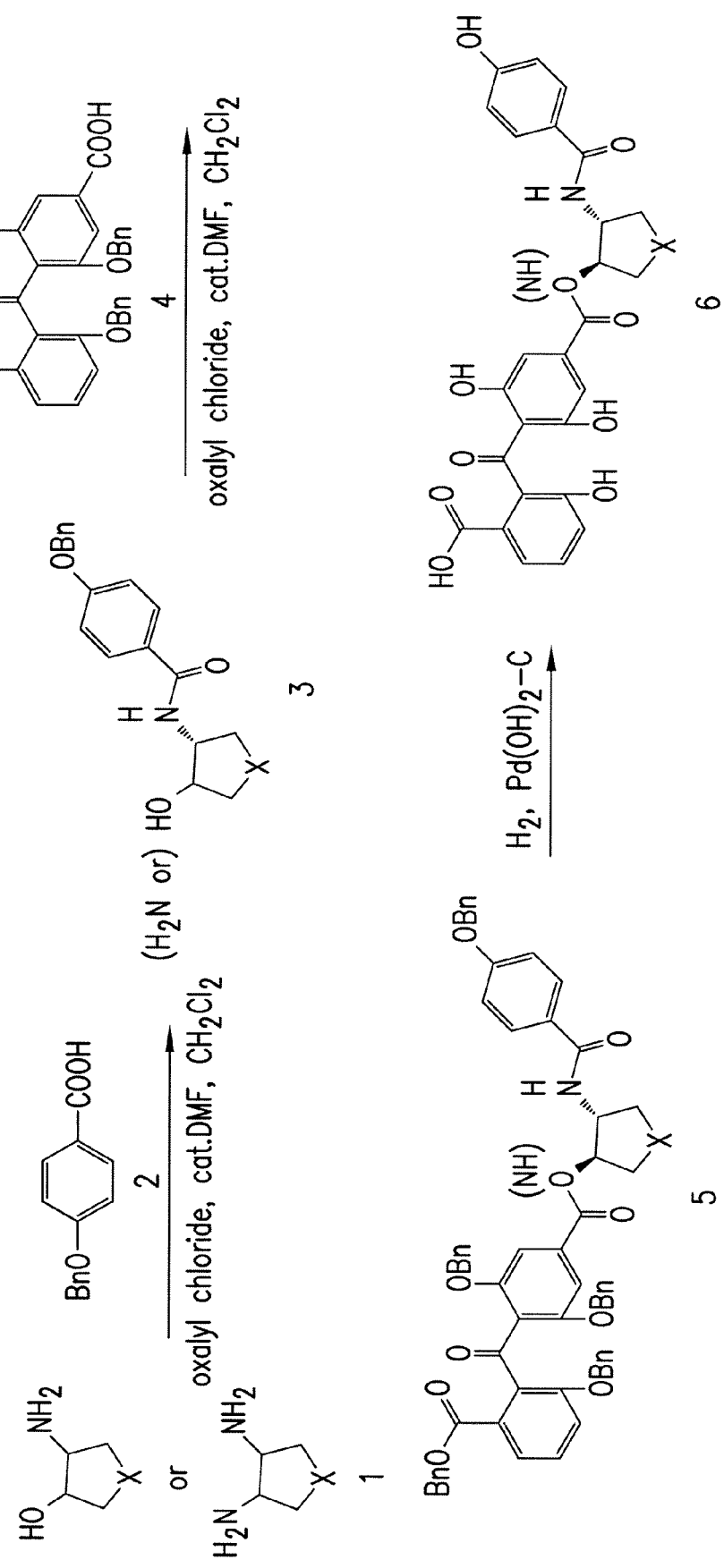

FIG. 16 provides a schematic of the synthesis of balanol analogues.

Figure 17A:
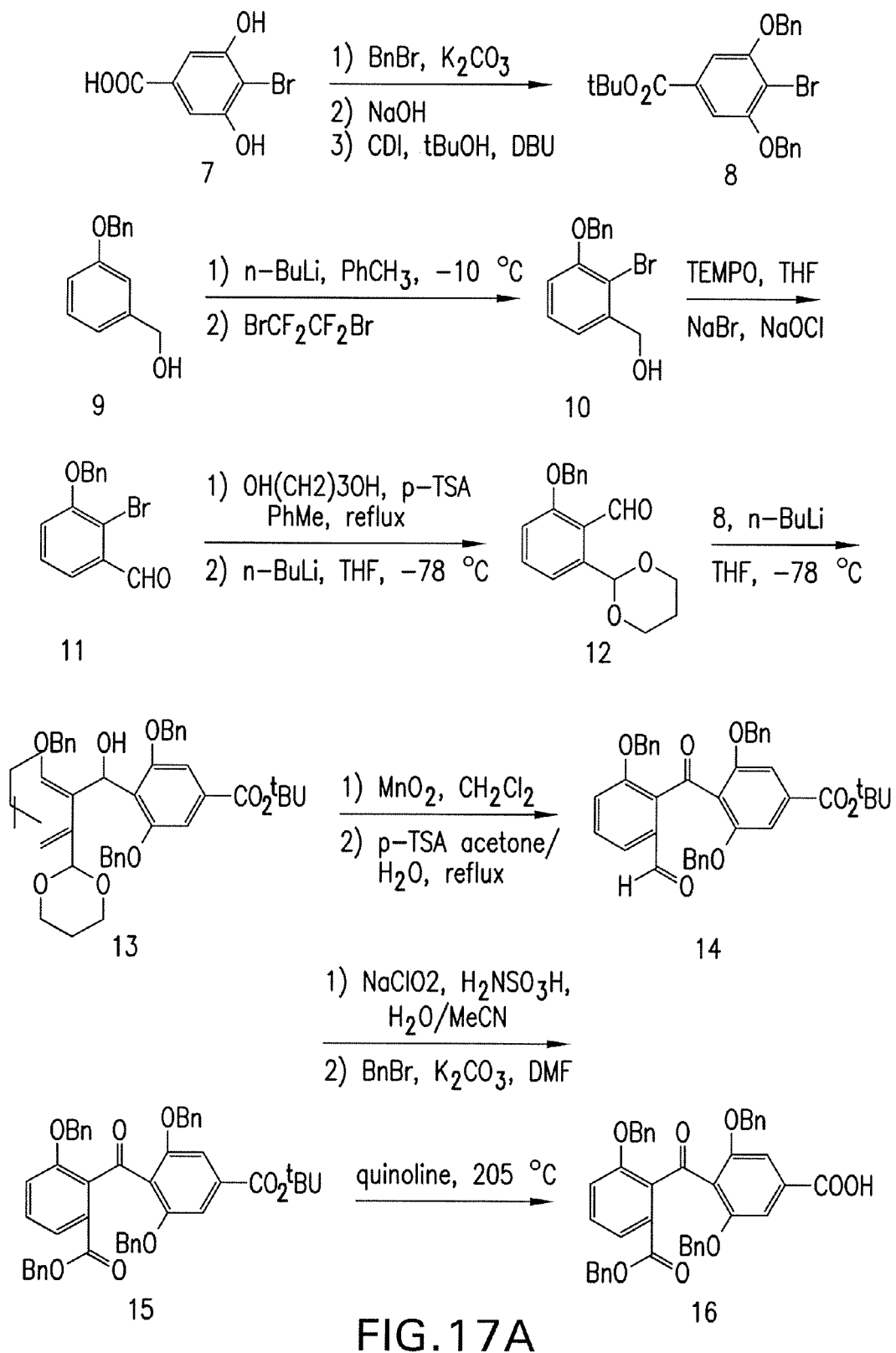
Figure 17B:
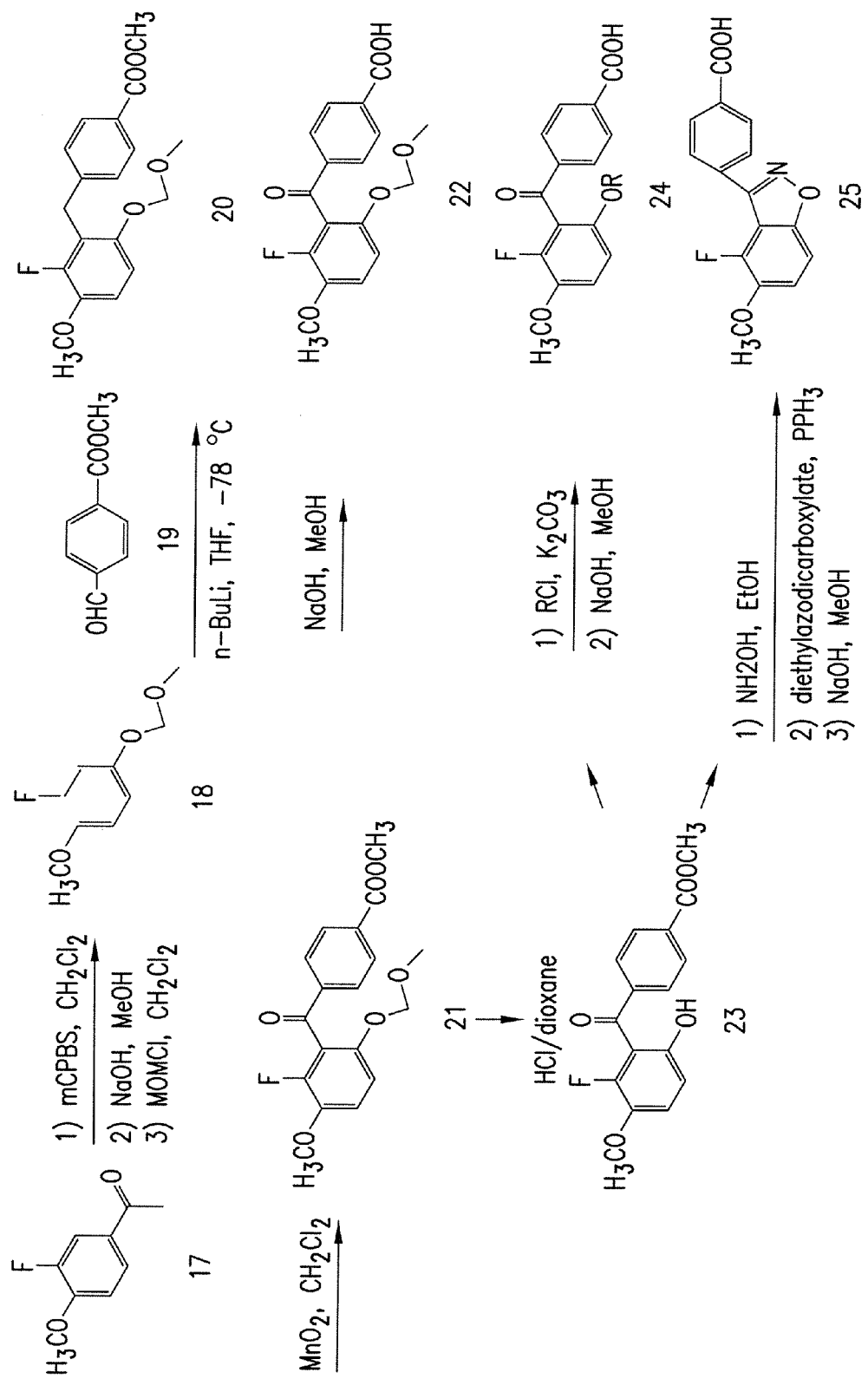
Figure 17C:
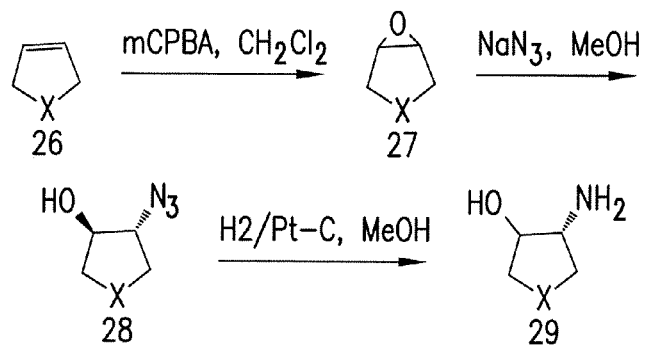
Figure 17D:
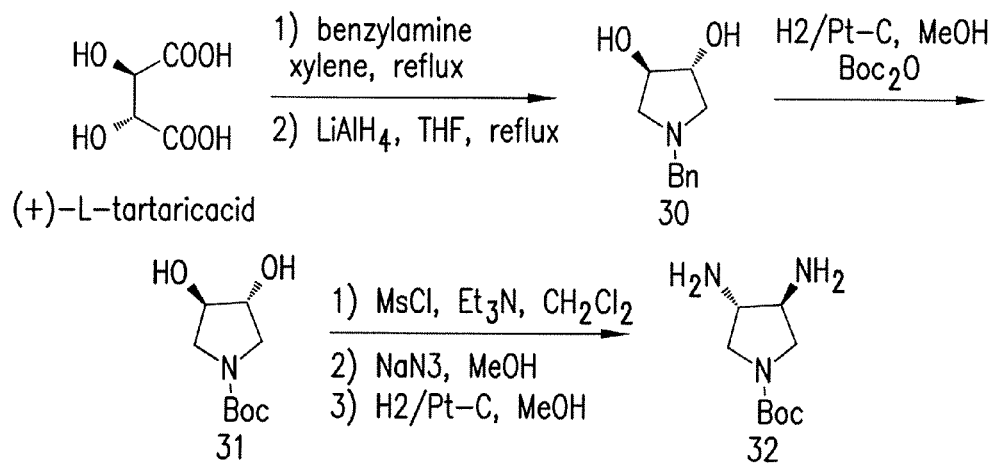
Figure 17E:
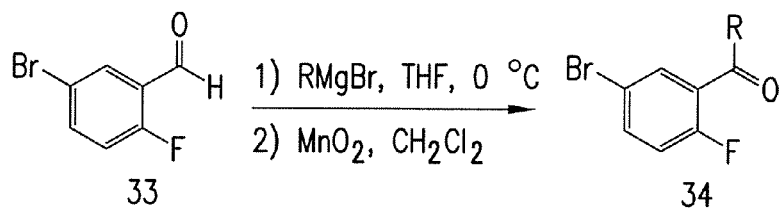
Figure 17E:
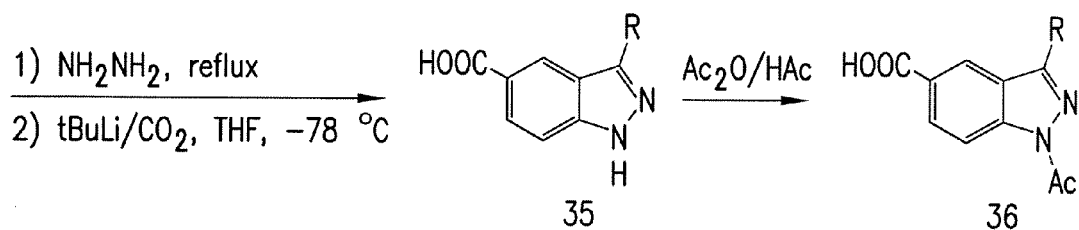

FIGS. 17A-17E provides schematics of the synthesis of various elements in the synthesis of balanol analogues. FIG. 17A shows the synthesis of the benzophenone subunit of balanol. FIG. 17B shows the synthesis of the simplified benzophenone subunit. FIG. 17C depicts synthesis of amino alcohols, and FIG. 17D shows the synthesis of diamines. FIG. 17E shows the synthesis of indazole acids.

Figure 18:
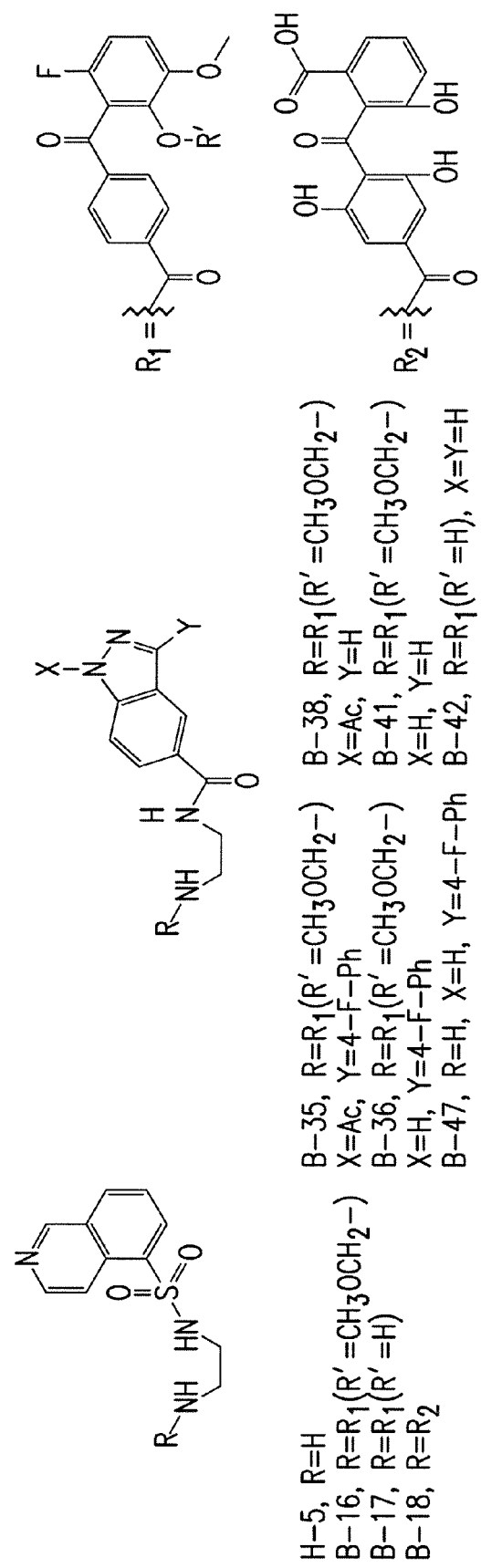

FIG. 18 shows the structures of certain balanol analogues.

Figure 19:
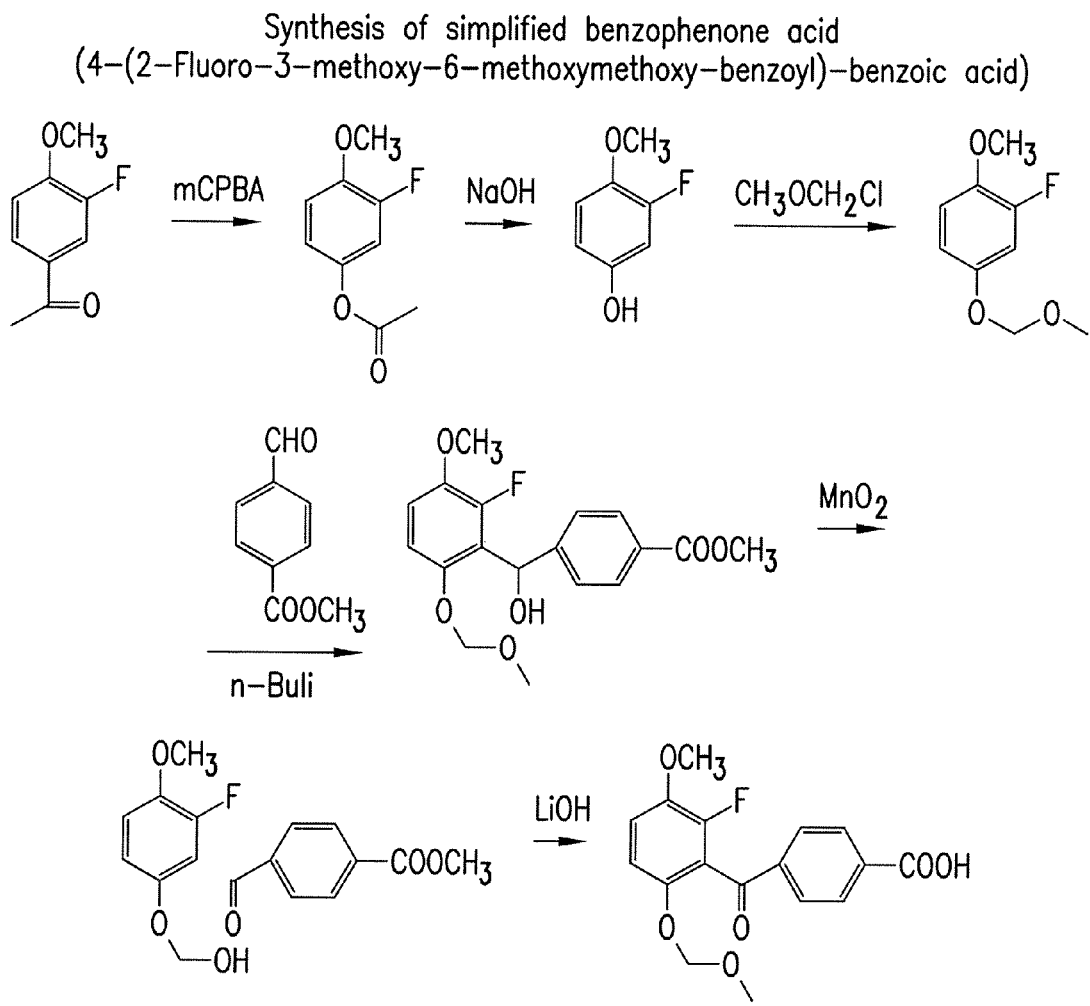

FIG. 19 shows a schematic of the synthesis of simplified benzophenone acid (4-(2-Fluoro-3-methoxy-6-methoxymethoxy-benzoyl)-benzoic acid).

Figure 20A:
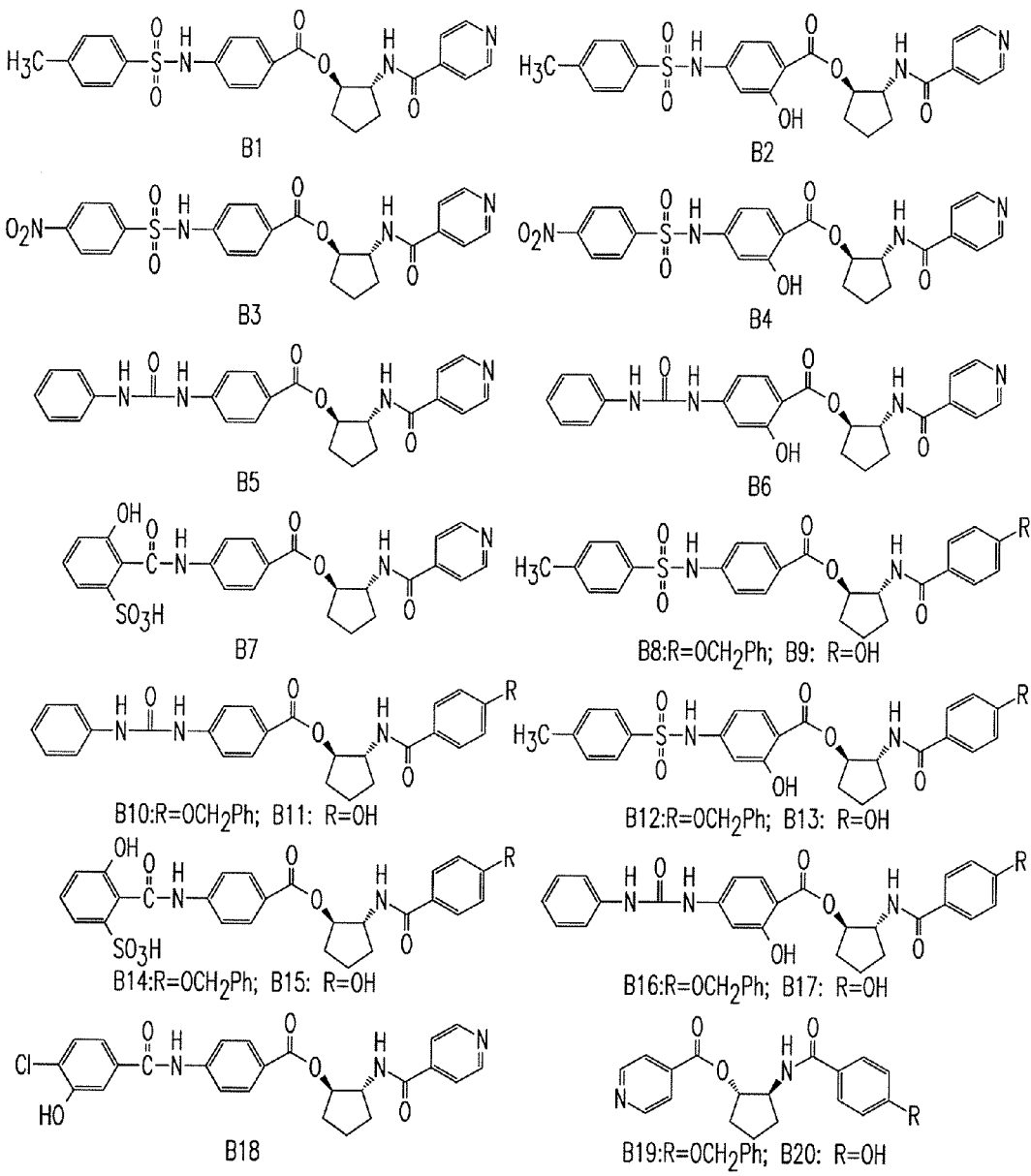
Figures 1, 20B:
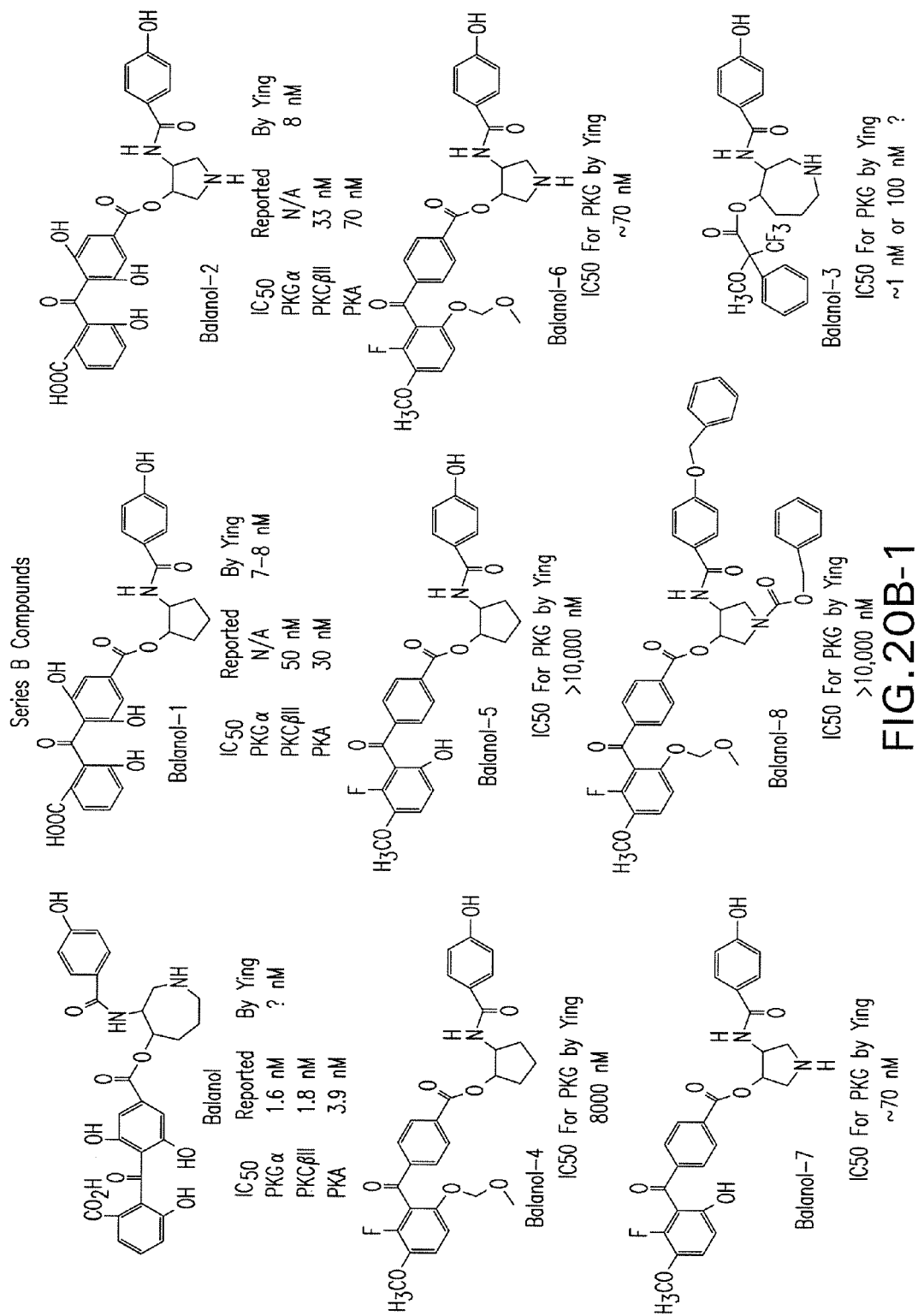

FIG. 20 provides the structures and inhibitory activity of various balanol type compounds. FIG. 20A represents the Series A compounds and FIG. 20B represents the Series B compounds.

Figure 21:
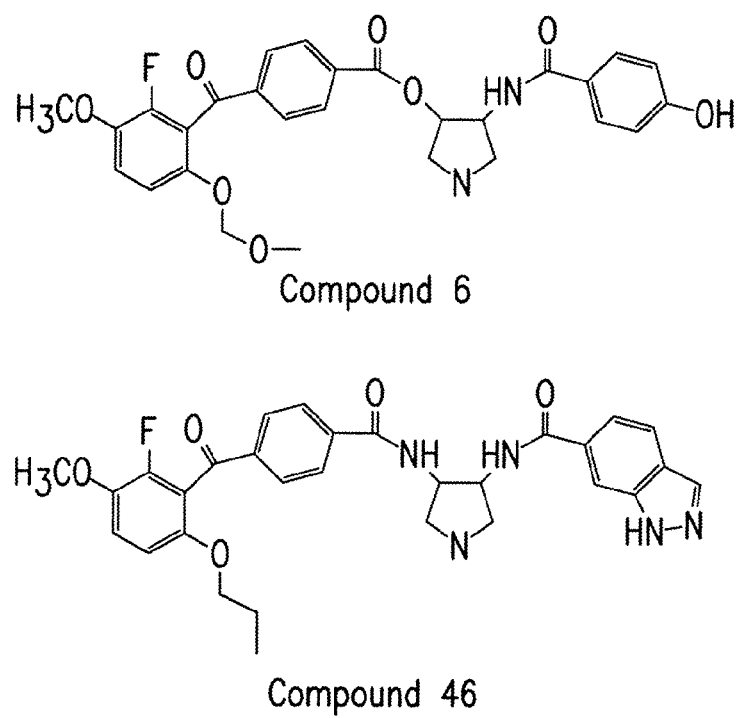

FIG. 21 shows the structures for compounds 6 and 46.

SEQUENCE LISTING

The specification further incorporates by reference a Sequence Listing submitted via EFS on Oct. 8, 2009. Pursuant to 37 C.F.R. §1.52(e)(5), the Sequence Listing text file, identified as 0700503258seqlist.txt, is 51,104 bytes and was created on Feb. 15, 2008. The Sequence Listing, electronically filed herewith, does not extend beyond the scope of the specification and thus does not contain new matter.

5. DETAILED DESCRIPTION OF THE INVENTION

For clarity of description, and not by way of limitation, this section is divided into the following subsections:
(i) modulators of PKG;
(ii) synthesis of modulators;
(iii) methods of use of modulators of PKG;
(iv) a PKG model system; and
(v) linkers to modify the lead compounds.

The following are terms relevant to the present invention:
Long-term hyperexcitability ("LTH"), as defined herein, is increased, persistent, sensitivity of a primary sensory neuron cell body or axon to stimuli. During electrophysiological testing, LTH is manifested as a decrease in spike threshold, an increase in repetitive firing, broader spikes, and/or an increase in spike amplitude. In animals that perceive pain, LTH is associated with persistent (chronic) pain (see Sung and Ambron, Mar. 22, 2004).

Electrophysiological testing may be performed using methods known in the art. One specific, non-limiting example of electrophysiological testing using *Aplysia californica* (hereafter referred to as either "*Aplysia californica*" or simply as "*Aplysia*") sensory neurons (SN) may be performed as follows (see Liao et al., 1999). Intracellular recordings from SN somata may be made with glass microelectrodes filled with 3 M potassium acetate (electrode resistance 8-20 M). Recordings may be made at 19-21° C. while the preparation is bathed in buffered artificial sea water ("ASW"), L15 medium, or a 1:1 mixture of ASW and L15, pH 7.6. Soma spike threshold may be measured with a standard series of 20 msec depolarizing pulses. Repetitive firing (spike accommodation) may be quantified by counting the number of spikes evoked by a 1 second intracellular depolarizing pulse using 2.5 times the threshold current determined with the 20 msec pulse. Repetitive firing may, for example, be examined by counting the number of spikes evoked by a series of 1 sec depolarizing pulses at 1.25, 2.5, and 5 times the threshold current, or by 1, 2, 3, and 5 nA. Input resistance (Rin) may be determined from the voltage change produced during injection of a 1 sec hyperpolarizing pulse (0.5 nA). Axon excitability may be tested by passing current between two compartments through a narrow, Vaseline-sealed opening containing nerves p7, p8, and p9. Threshold may be determined with a rapid series of 2 msec pulses.

Persistent pain (also referred to as chronic pain) includes pain that endures longer than the period of acute injury, and includes chronic pain syndromes such as, but not limited to, neuropathic pain (see Bennett et al., 2005). In specific, non-limiting embodiments, the duration of persistent pain is at least 1 day, at least one week, at least one month, or at least one year.

The terms aryl and heteroaryl include fused and unfused ring(s); and the term alkyl includes both branched and unbranched alkyls.

5.1 Modulators of PKG

In various embodiments of the invention, the present invention provides for compounds that bind to the active site of PKG and preferably inhibit PKG activity. Non-limiting examples of compounds that may be used as PKG modulators were identified by docking compounds to two homology models of the ATP binding domain of PKG, as described in Example Section 6 and FIG. 8C-8L. A number of classes, subclasses and specific examples of PKG inhibitors are set forth herein.

One class of identified PKG modulators may be represented by general Formula I:

*A-D-E*    Formula I wherein the following substituents are named with respect to Formula I:

A may be a substituted or unsubstituted ring structure which may comprise fused rings; for example, and not by way of limitation, A may be substituted or unsubstituted chromanyl or isochromanyl, where the substituent may (without limitation) be one or more ketone, one or more hydroxyl, or a ketone, halogen, carbamoyl, amido, and hydroxyl group;

A may be a substituted or unsubstituted pyridyl, where the substituent may (without limitation) be $(C_1-C_4)$ alkyl, halo, hydroxyl, carbamoyl, amido, amino, and carbonyl;

A may be a substituted or unsubstituted indole, isoindole, or indazole, where the substituent may (without limitation) be $(C_1-C_4)$alkyl, halogen, hydroxyl, carbamoyl, amido, amino, and carbonyl; or A may be a substituted or unsubstituted phenyl, where the substituent may, without limitation, be hydroxyl, $(C_1-C_4)$ alkoxy, $(C_1-C_4)$alkyl, preferably (p)hydroxyphenyl, and wherein more than one such substituent may be present;

D may be a 5-11 atom chain, preferably comprised of carbon and at least one heteroatom such as (without limitation) N, O, or S, optionally comprising one or more amide bond; and/or one or more $(C_4-C_7)$ ring, said ring optionally comprising at least one unsaturated bond and optionally fused to A; and/or $SO_2$; and E may comprise (i) $(C_1-C_4)$alkyl; (ii)$(C_5-C_{13})$cyclic or heterocyclic (including fused cyclic or heterocyclic); or (iii) $(C_1-C_4)$alkyl$(C_5-C_{13})$heterocyclic; E may optionally comprise unsubstituted or substituted phenyl (e.g. fluorophenyl, chlorophenyl, hydroxyphenyl), and may comprise one or more of N, O, S, Br, Cl, F or I.

More particularly, in various non-limiting embodiments, the present invention provides a pharmaceutical composition for treating chronic pain in a subject using PKG inhibitor compounds, in an amount effective at inhibiting long-term hyperexcitability of sensory neurons in a subject to which it is administered, represented by Formula II:

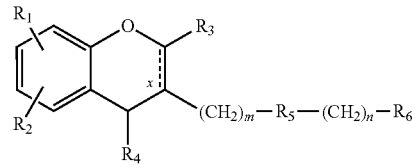

Formula II wherein the following substituents are named with respect to Formula II:

wherein $R_1$ may be H, $(C_1-C_4)$alkyl, $(C_2-C_4)$alkenyl, $(C_1-C_4)$alkoxy, $(C_2-C_4)$alkynyl, halo, carbamoyl, amido, amino, cyano, $(C_1-C_4)$alkylcarbonyl or hydroxyl;

wherein $R_2$ may be H, $(C_1-C_4)$alkyl, $(C_2-C_4)$alkenyl, $(C_1-C_4)$alkoxy, $(C_2-C_4)$alkynyl, halo, carbamoyl, amido, amino, cyano, $(C_1-C_4)$alkylcarbonyl or hydroxyl or hydroxyl;

wherein $R_3$ may be H, $(C_1-C_4)$alkyl, keto-, $(C_2-C_4)$alkenyl, $(C_1-C_4)$alkoxy, $(C_2-C_4)$alkynyl, halo, carbamoyl, amido, amino, cyano, $(C_1-C_4)$alkylcarbonyl or hydroxyl or hydroxyl;

wherein $R_4$ may be H, $(C_1-C_4)$alkyl, keto-, $(C_2-C_4)$alkenyl, $(C_1-C_4)$alkoxy, $(C_2-C_4)$alkynyl, halo, carbamoyl, amido, amino, cyano, $(C_1-C_4)$alkylcarbonyl or hydroxyl or hydroxyl, and wherein if $R_4$ is keto, x is a single bond, and wherein if $R_4$ is not keto, x is a double bond;

wherein m may be 0-4;

wherein $R_5$ may be amido, $(C_1-C_4)$alkylamido, amido$(C_1-C_4)$alkyl; carbonyl$(C_1-C_4)$alkylamido; $(C_1-C_4)$alkylcarboxy$(C_1-C_4)$alkylamido, or amido$(C_1-C_4)$alkylamido;

wherein n may be 0-4;

wherein $R_6$ may be $(C_1-C_4)$alkylhydroxyphenyl or a $(C_5-C_{13})$cyclic or heterocyclic ring preferably comprising N and one or more additional heteroatom selected from N, O, or S; and wherein each of the aforesaid groups being capable to have one or more substituents may optionally be substituted with one or more substituents independently selected from halo, $(C_1-C_4)$alkyl, hydroxyl, amino, $(C_1-C_4)$alkoxy, or $CF_3$.

Figure 8A:
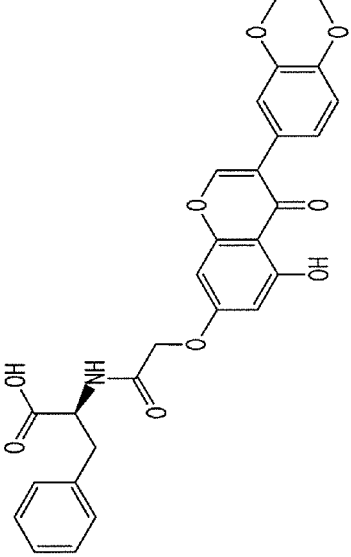
Figure 8B:
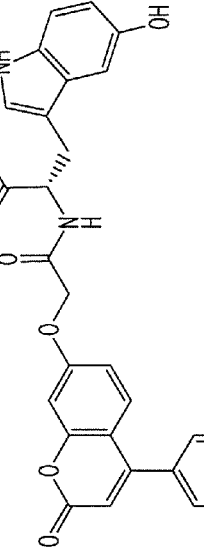
Figure 8C:
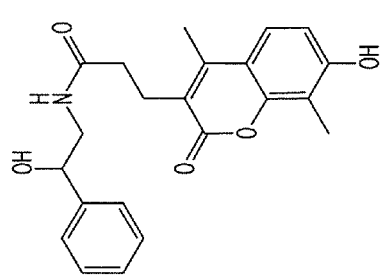

Compound 8C, shown in FIG. 8C, is a non-limiting example of a compound of Formula II.

In other non-limiting embodiments, the present invention provides a pharmaceutical composition for treating chronic pain in a subject using PKG inhibitor compounds, in an amount effective at inhibiting long-term hyperexcitability of sensory neurons in a subject to which it is administered, represented by Formula III:

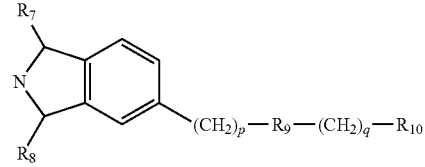

Formula III wherein the following substituents are named with respect to Formula III:

wherein $R_7$ may be H, $(C_1-C_4)$alkyl, $(C_2-C_4)$alkenyl, $(C_1-C_4)$alkoxy, $(C_2-C_4)$alkynyl, halo, carbamoyl, amido, amino, cyano, $(C_1-C_4)$alkylcarbonyl or keto;

wherein $R_8$ may be H, $(C_1-C_4)$alkyl, $(C_2-C_4)$alkenyl, $(C_1-C_4)$alkoxy, $(C_2-C_4)$alkynyl, halo, carbamoyl, amido, amino, cyano, $(C_1-C_4)$alkylcarbonyl or keto;

wherein p may be 0-4;

wherein $R_9$ may be amido, $(C_1-C_4)$alkylamido, amido$(C_1-C_4)$alkyl; carbonyl$(C_1-C_4)$alkylamido; $(C_1-C_4)$alkylcarboxy $(C_1-C_4)$alkylamido, or amido$(C_1-C_4)$alkylamido;

wherein q may be 0-4;

wherein $R_{10}$ may be a substituted or unsubstituted carboline, having one or more substituent selected from $(C_1-C_4)$alkyl, hydroxy, $(C_2-C_4)$alkenyl, $(C_2-C_4)$alkynyl, halo, carbamoyl, amido, amino, cyano, $(C_1-C_4)$alkylcarbonyl, and $(C_1-C_4)$alkoxy; and wherein each of the aforesaid groups being capable to have one or more substituents may optionally be substituted with one or more substituents independently selected from halo, $(C_1-C_4)$alkyl, hydroxyl, amino, $(C_1-C_4)$alkoxy, or $CF_3$.

Figure 8D:
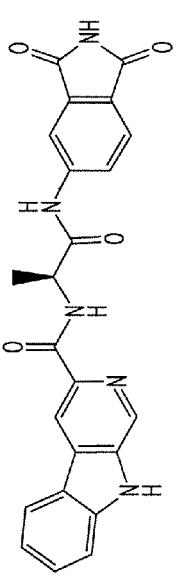

Compound 8D, as shown in FIG. 8D, is a non-limiting example of a compound of Formula III.

In other non-limiting embodiments, the present invention provides a pharmaceutical composition for treating chronic pain in a subject using PKG inhibitor compounds, in an amount effective at inhibiting long-term hyperexcitability of sensory neurons in a subject to which it is administered, represented by Formula IV:

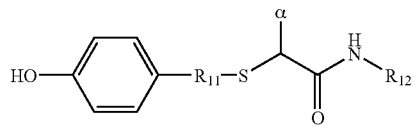

Formula IV wherein the following substituents are named with respect to Formula IV:

wherein $R_{11}$ may be a substituted or unsubstituted oxadiazole or triazole, wherein the substituent may be $(C_1-C_4)$alkyl, hydroxy, $(C_2-C_4)$alkenyl, $(C_2-C_4)$alkynyl, halo, carbamoyl, amido, amino, cyano, $(C_1-C_4)$alkylcarbonyl, and $(C_1-C_4)$alkoxy;

wherein $R_{12}$ may be a substituted or unsubstituted naphthyl, anthryl, phenanthryl, or quinolyl, wherein the substituent may be $(C_1-C_4)$alkyl, hydroxy, $(C_2-C_4)$alkenyl, $(C_2-C_4)$alkynyl, halo, carbamoyl, amido, amino, cyano, $(C_1-C_4)$alkylcarbonyl, and $(C_1-C_4)$alkoxy;

wherein α is H, $(C_1-C_4)$alkyl, halo, $(C_1-C_4)$alkoxy or hydroxy; and wherein each of the aforesaid groups being capable to have one or more substituents may optionally be substituted with one or more substituents independently selected from halo, $(C_1-C_4)$alkyl, hydroxyl, amino, $(C_1-C_4)$alkoxy, or $CF_3$.

Figure 8G:
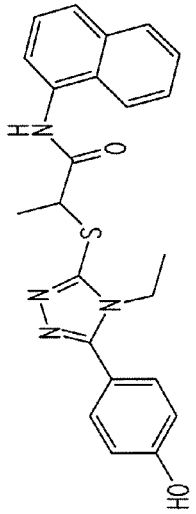
Figure 8H:
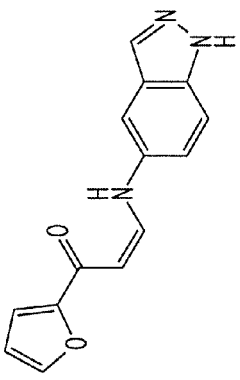
Figure 8I:
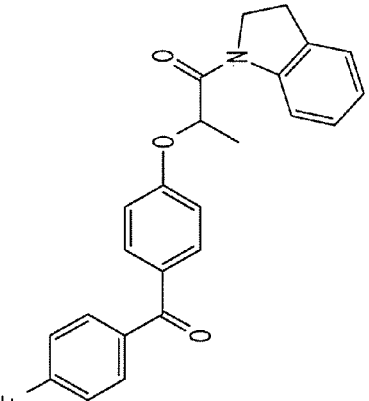
Figure 8J:
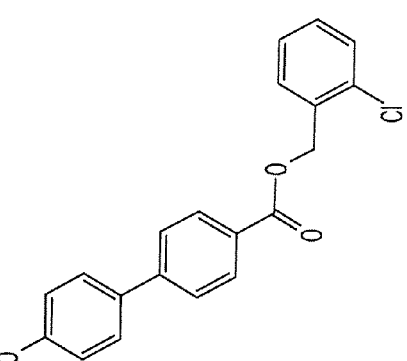
Figure 8K:
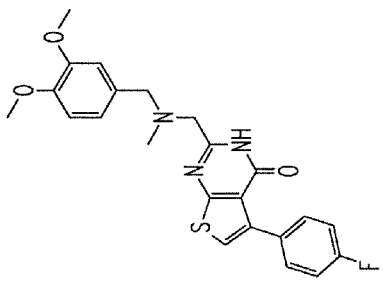
Figure 8L:
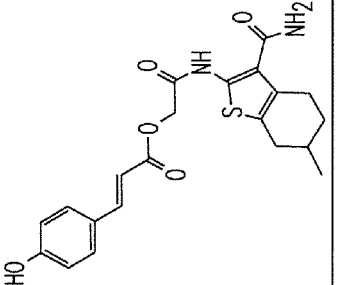
Figure 9A:
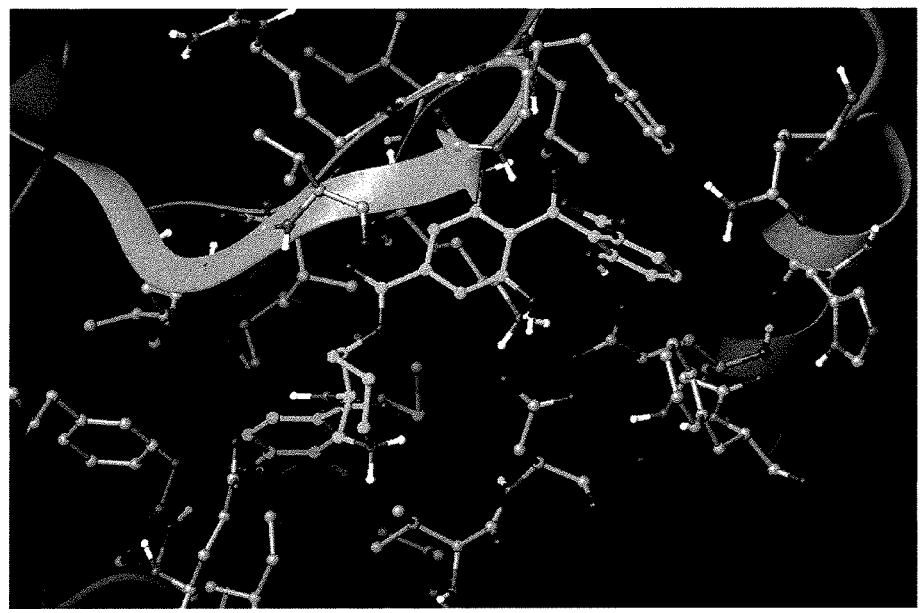
Figure 9B:
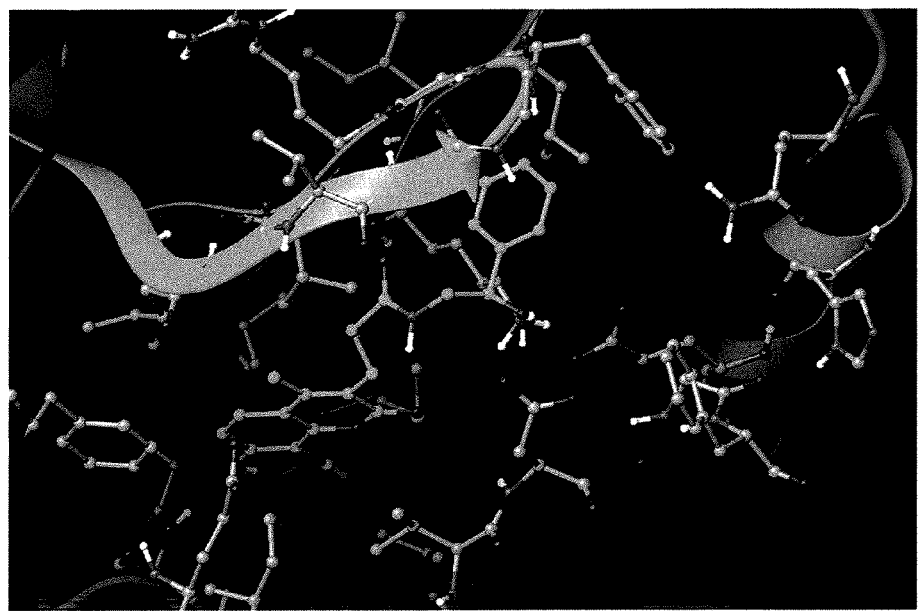
Figure 9C:
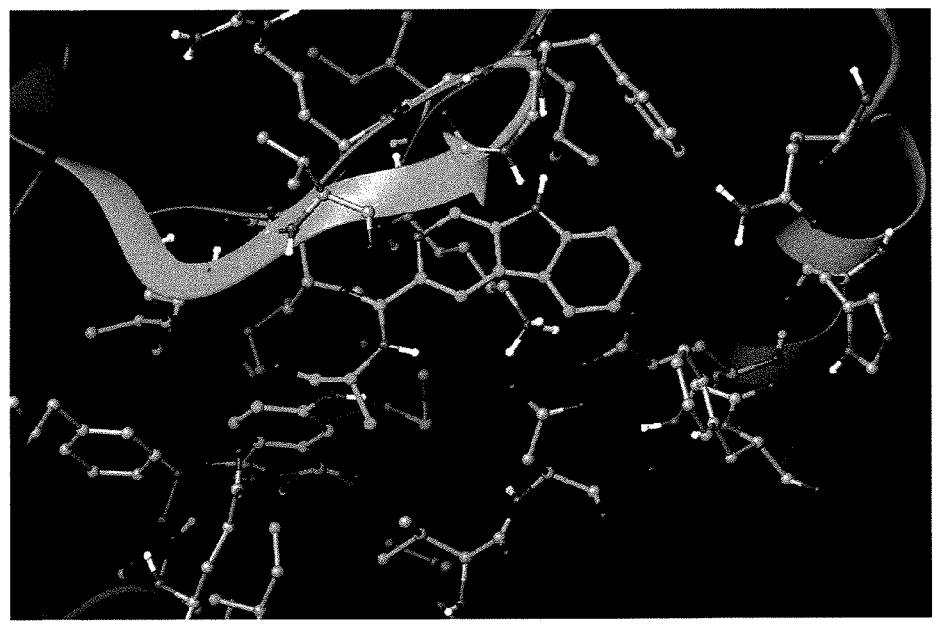
Figure 9D:
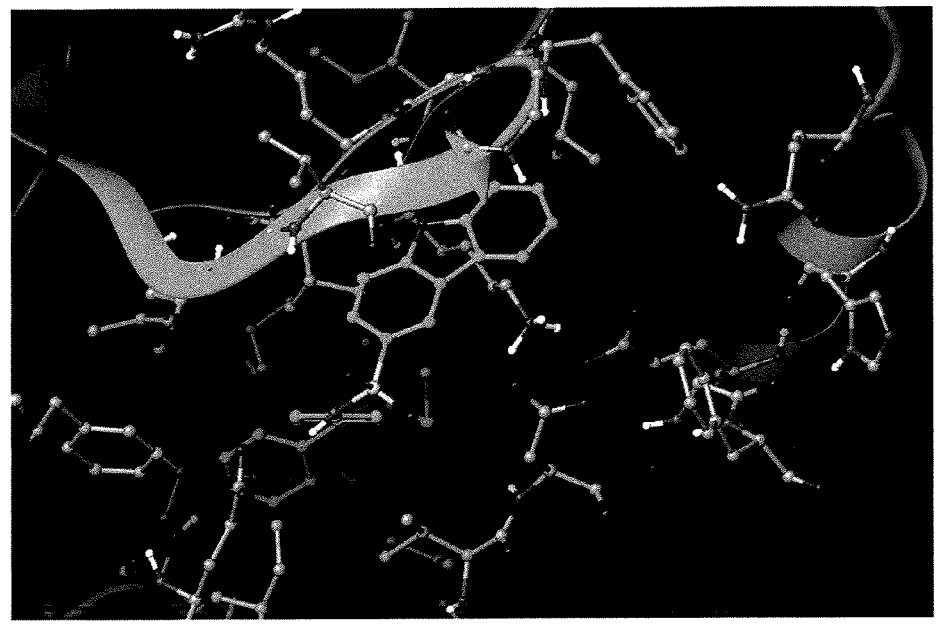
Figure 9E:
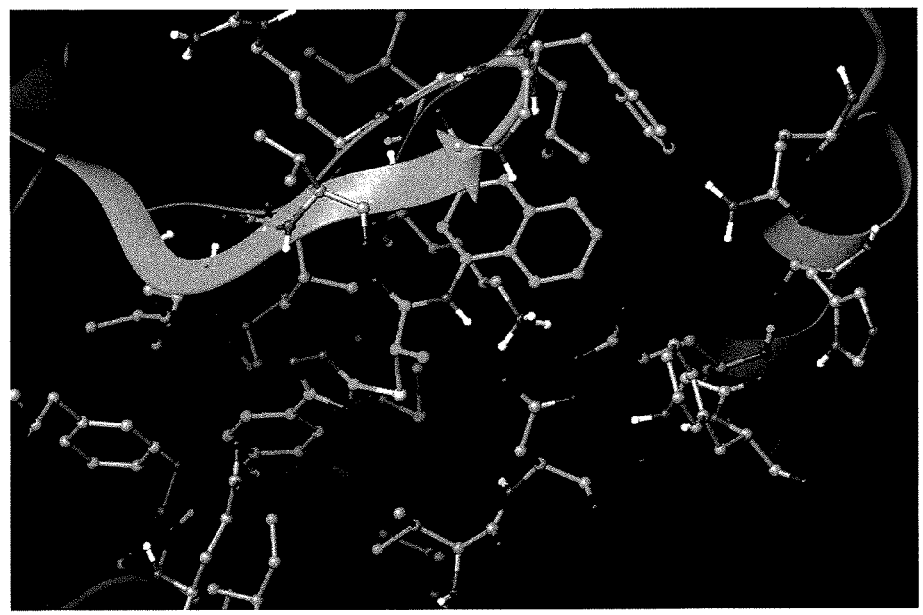
Figure 9F:
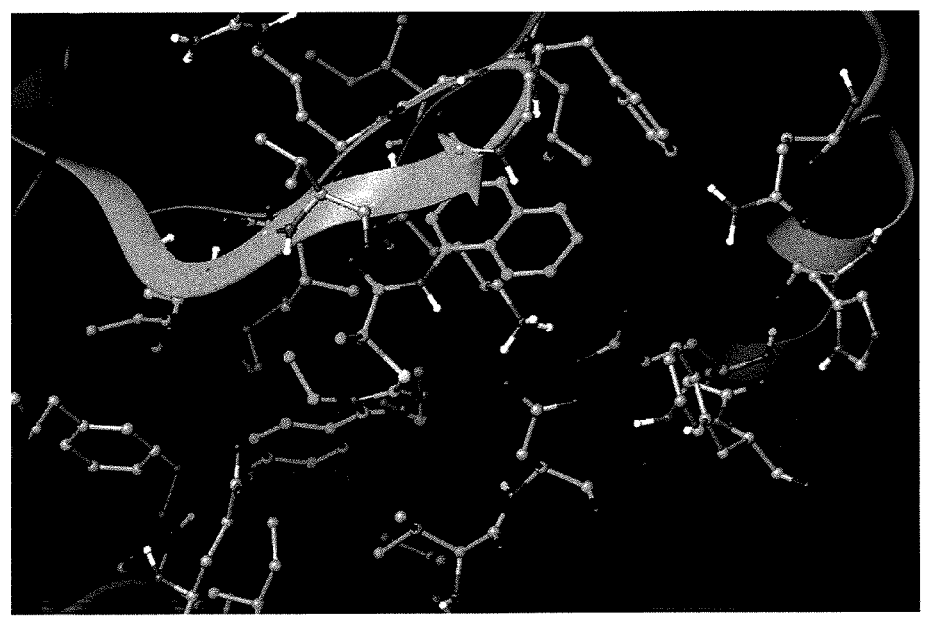
Figure 9G:
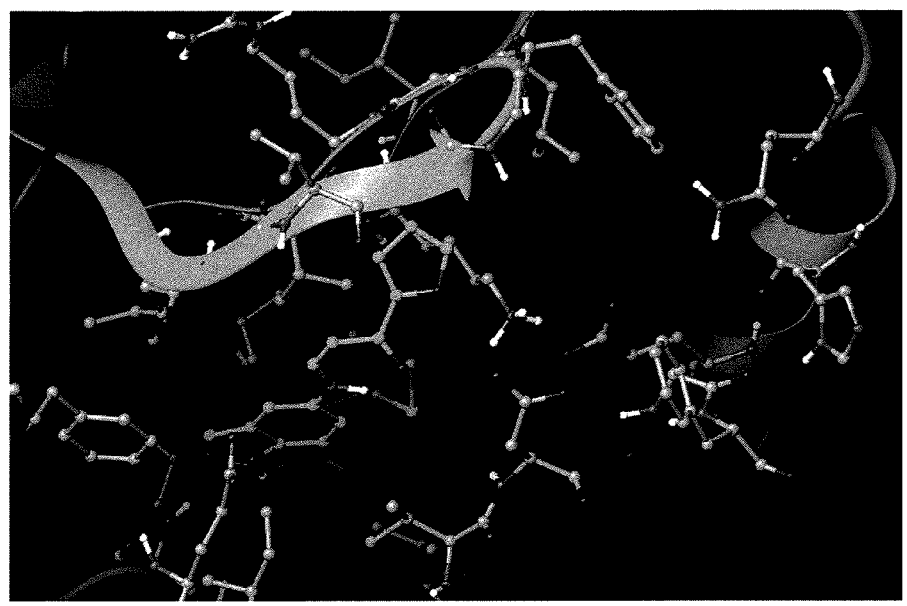
Figure 9H:
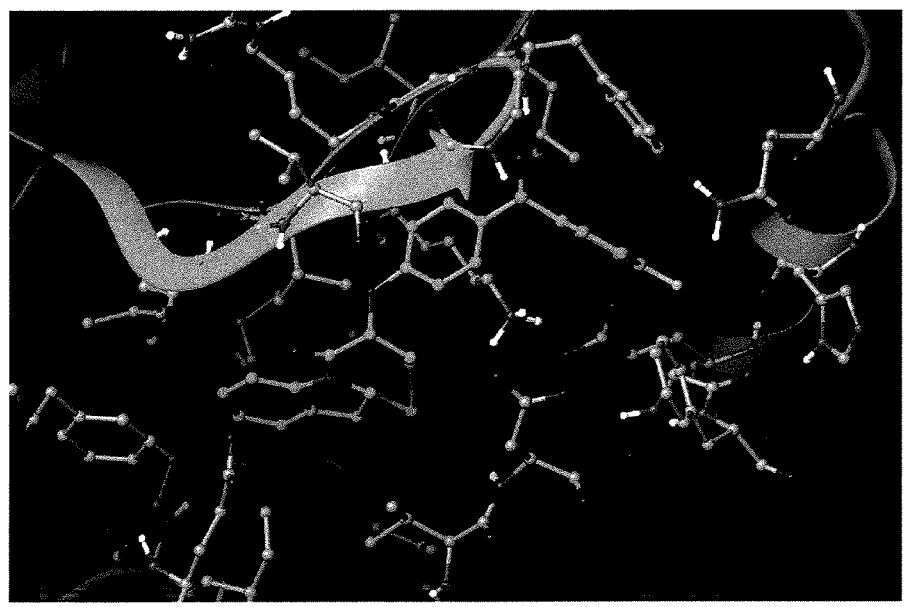
Figure 9I:
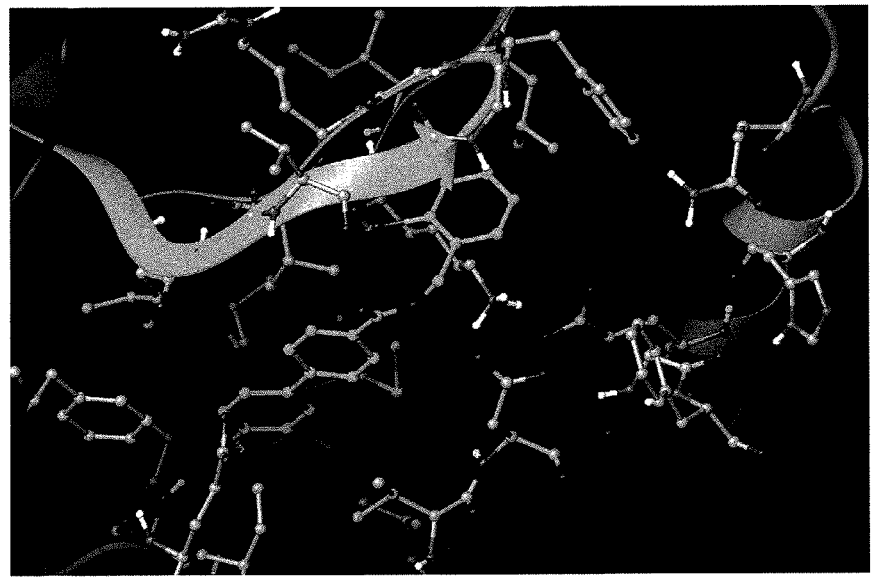
Figure 9J:
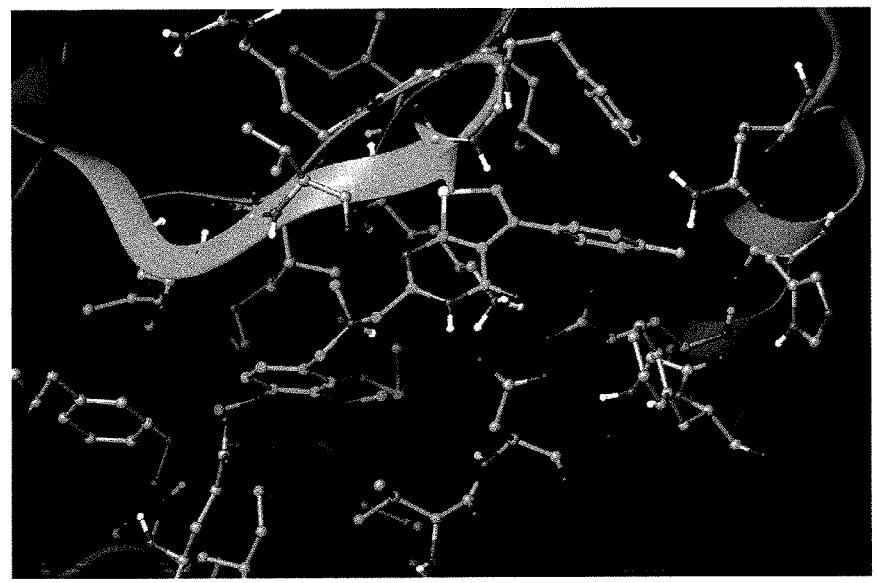
Figure 9K:
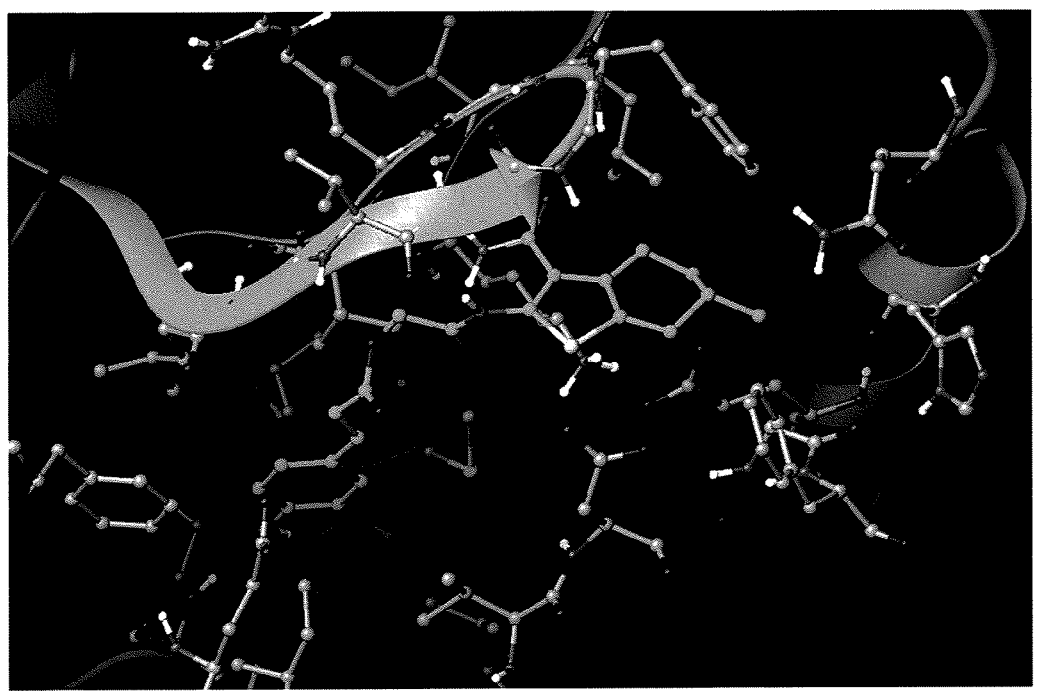

Compounds 8F and 8G, as shown in FIGS. 8F and 8G, are non-limiting examples of compounds of Formula IV.

In one set of non-limiting embodiments, the present invention provides a pharmaceutical composition for treating chronic pain in a subject using derivatives of balanol, in an amount effective at inhibiting long-term hyperexcitability of sensory neurons in a subject to which it is administered, where balanol is disclosed in International Patent Application No. PCT/US92/07124, Publication No. WO93/03730 and the following structural Formula V:

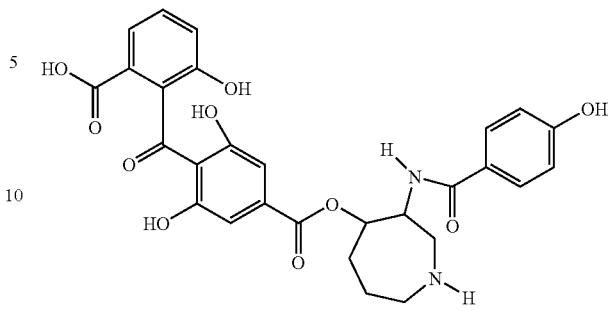

Formula V

Figure 6:
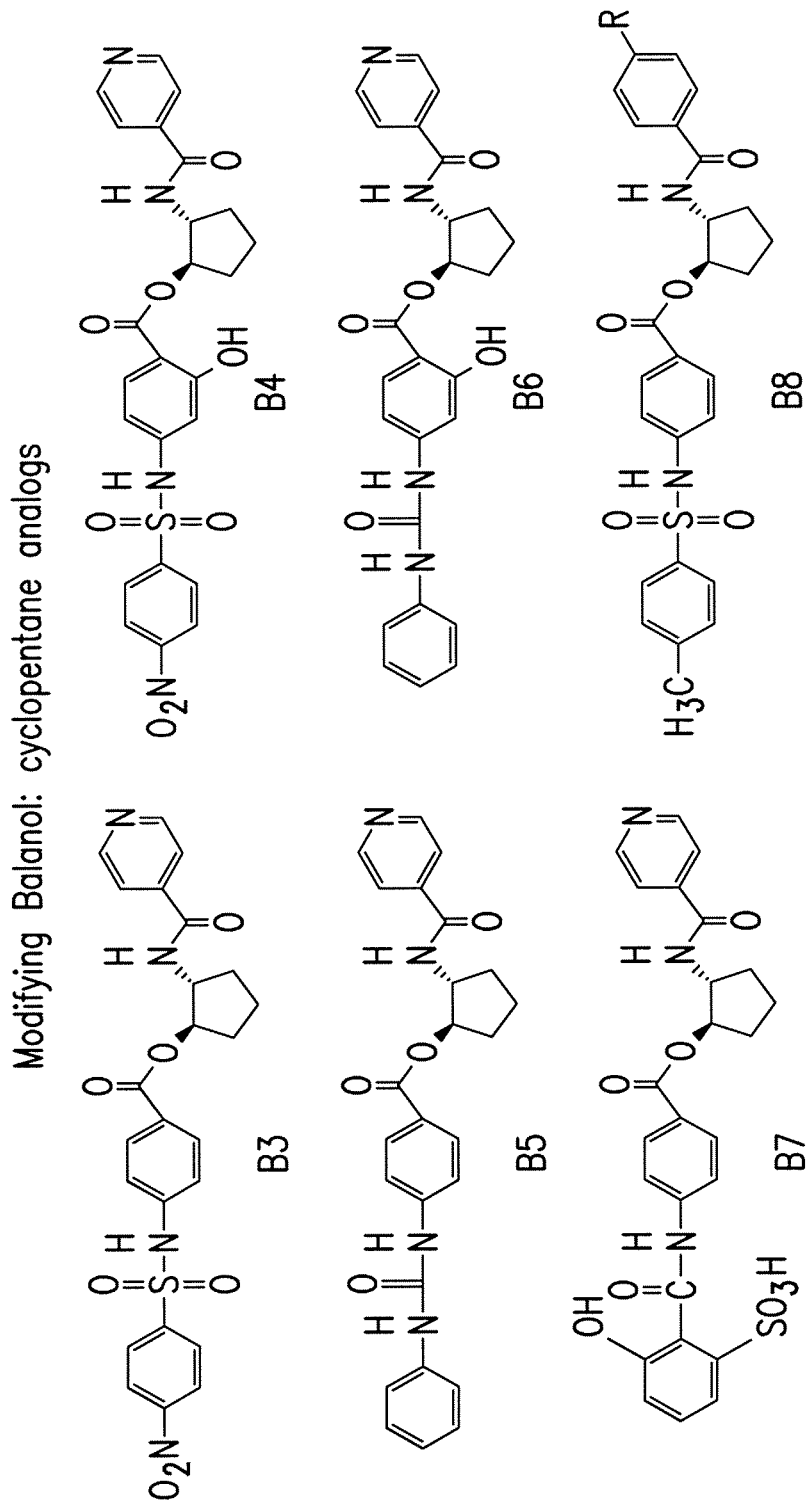

In particular nonlimiting embodiments of the invention, Formula V may be varied to provide "balanol variants" which inhibit PKG. Non-limiting examples of such balanol variants include cyclopentane analogs of balanol, as shown in FIG. 6.

In various embodiments, the present invention provides for PKG inhibitor compounds represented by Formula VI, and pharmaceutical compositions comprising said compounds for treating chronic pain in a subject. Formula VI is represented by the following formula:

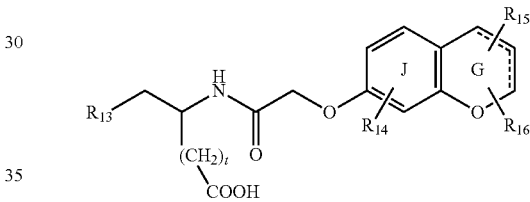

Formula VI wherein the following substituents are named with respect to Formula VI:

wherein $R_{13}$ may be substituted or unsubstituted phenyl, indolinyl, or isoindolinyl, wherein the substituent may be $(C_1-C_4)$alkyl, hydroxy, $(C_2-C_4)$alkenyl, $(C_2-C_4)$alkynyl, halo, carbamoyl, amido, amino, cyano, $(C_1-C_4)$alkylcarbonyl, and $(C_1-C_4)$alkoxy, and wherein more than one (e.g. 2 or 3) such substituents may be present;

wherein t may be 0-4;

wherein $R_{14}$ may be $(C_1-C_4)$alkyl, hydroxy, $(C_2-C_4)$alkenyl, $(C_2-C_4)$alkynyl, halo, carbamoyl, amido, amino, cyano, $(C_1-C_4)$alkylcarbonyl, and $(C_1-C_4)$alkoxy;

wherein $R_{15}$ and/or $R_{16}$ may be hydrogen, hydroxyl, $(C_1-C_4)$alkyl, $(C_1-C_4)$alkoxy, heteroaryl or heterocyclic aryl, or keto or substituted or unsubstituted phenyl, dimethoxyphenyl, or substituted or unsubstituted ethylenedioxyphenyl; preferably (but not by way of limitation) $R_{15}$ or $R_{16}$ is a ketone, and ring G optionally further contains at least one double bond; and wherein each of the aforesaid groups being capable to have one or more substituents may optionally be substituted with one or more substituents independently selected from halo, $(C_1-C_4)$alkyl, hydroxyl, amino, $(C_1-C_4)$alkoxy, or $CF_3$. Preferably, but not by way of limitation, rings G and J together form a substituted or unsubstituted chromenone, e.g. a chromen-4-one or a chromen-2-one, where the substituents, which may be singular or plural, of said chromenone may be as set forth above in this paragraph).

Compounds 8A and 8B, shown in FIGS. 8A and 8B, are non-limiting examples of compounds of Formula VI.

In various embodiments, the present invention provides for PKG inhibitor compounds represented by Formula VII, and pharmaceutical compositions comprising said compounds for treating chronic pain in a subject using PKG inhibitor compounds:

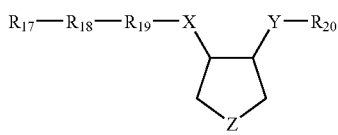

Formula VII wherein the following substituents are named with respect to Formula VII:
wherein X and Y are at trans or cis-configuration; and
wherein Z represents one of the following groups, or groups represented by X or Y;

Z=—O— —CH₂O— —OCH₂— —CH₂CH₂O—
—OCH₂CH₂— —CH₂OCH₂— —N—
—CH₂N— —NCH₂— —CH₂CH₂N—
—NCH₂CH₂— —CH₂NCH₂— —CH₂—
—CH₂CH₂— —CH₂CH₂CH₂— wherein X represents one of the following functional groups:

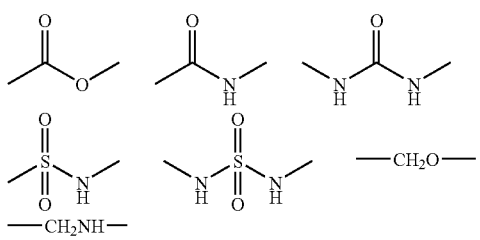

wherein Y represents one of the following functional groups:

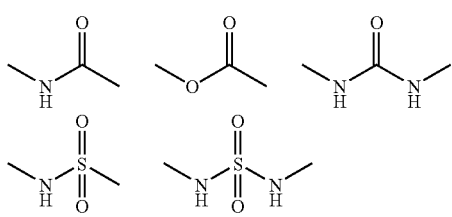

wherein $R_{17}$ may be a substituted or unsubstituted aryl, heteroaryl, wherein there may be more than one substituent and each substituent may be hydroxyl, —CN, —NO₂, ($C_1$-$C_4$)alkoxy, halo, ($C_2$-$C_4$)alkenyl, ($C_2$-$C_4$)alkynyl, ($C_1$-$C_4$) alkyl, or —SO₃H;
wherein $R_{18}$ may be amide, sulfonamide, or urea group; examples of the R18 are listed below:

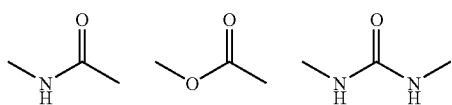

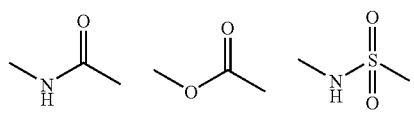

wherein $R_{19}$ may be ($C_1$-$C_5$)alkyl, aryl or heteroaryl un-substituted or substituted by one or more lower-alkyl, lower-alkoxy, hydroxy, alkoxy, amino, alkylamino or halogen groups; and
wherein $R_{20}$ represents aryl or heteroaryl groups un-substituted or substituted by one or more lower-alkyl, lower-alkyl, hydroxy, ($C_2$-$C_4$)alkenyl, ($C_2$-$C_4$)alkynyl, carbamoyl, amido, carbonyl, amino or halo groups
wherein each of the aforesaid groups being capable to have one or more substituents may optionally be substituted with one or more substituents independently selected from halo, ($C_1$-$C_4$)alkyl, hydroxyl, amino, ($C_1$-$C_4$)alkoxy, or CF₃.
Examples of the aryl or heteroaryl groups are listed below:
When Y is:

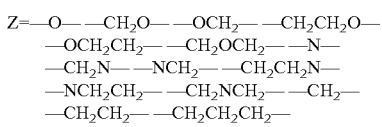

R20 is:

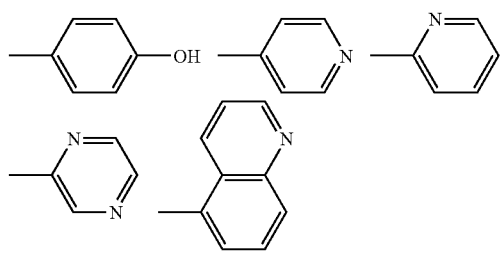

When Y is:

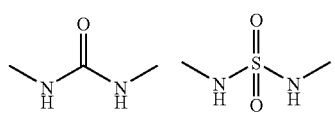

R20 is:

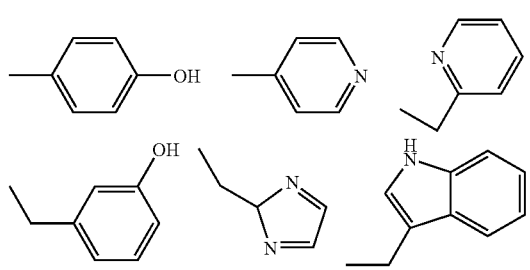

Examples of compounds having Formula VII include compounds 8A and 8B.

In various embodiments, the present invention provides for PKG inhibitor compounds represented by Formula VIII and pharmaceutical composition comprising said compounds:

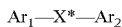  Formula VIII wherein the following substituents are named with respect to Formula VIII:

wherein X* represents, but not limited to, one of the following groups;

X* =

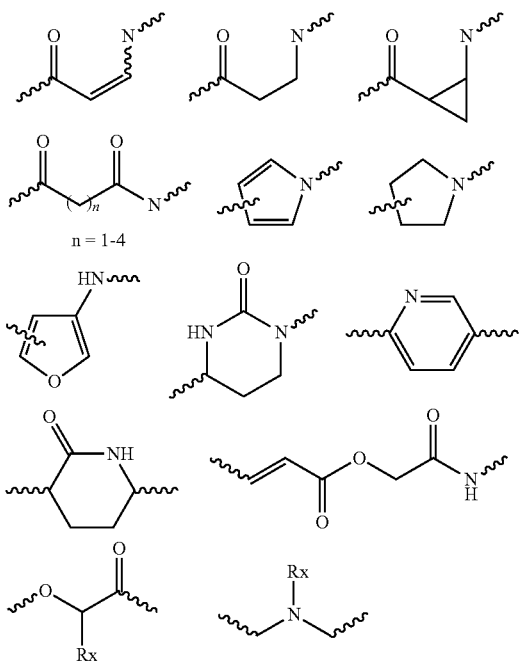

n = 1-4 wherein Ar₁=Aryl, or heteroaryl, substituted or unsubstituted, for example:

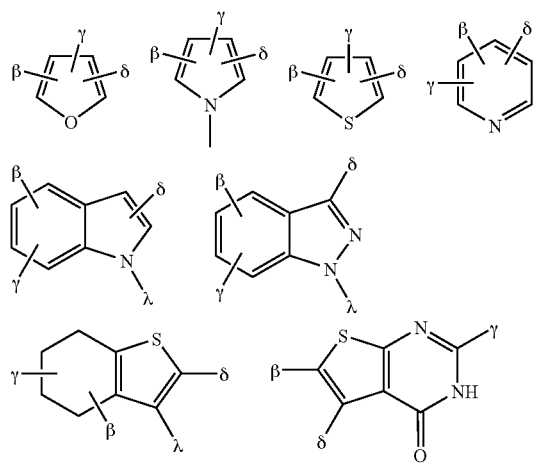

wherein one of δ, β, γ and λ— is the bond to X*, and the others are respectively H, $(C_1-C_4)$alkyl, $(C_2-C_4)$alkenyl, $(C_2-C_4)$alkynyl, halo, carbonyl, amido, cyano, carbamoyl, or aryl;

wherein Ar₂=aryl, or heteroaryl, substituted or unsubstituted, for example:

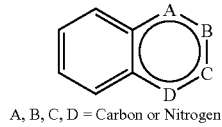

A, B, C, D = Carbon or Nitrogen wherein the substitutent(s) of any of the foregoing groups, which are optionally present and may be singular or plural, include, but are not limited to, alkyl (e.g., $(C_1-C_4)$alkyl), aryl, alkoxy (e.g. $(C_1-C_4)$alkoxy), alkylcarbonyl (e.g., $(C_1-C_4)$alkylcarbonyl), phenyl, alkylphenyl, halo, alkenyl (e.g., $(C_2-C_4)$alkenyl), alkynyl (e.g., $(C_2-C_4)$alkynyl) or hydroxy;

wherein $R_x$ is hydrogen, halo, $(C_1-C_4)$alkoxy or $(C_1-C_4)$alkyl and wherein each of the aforesaid groups being capable to have one or more substituents may optionally be substituted with one or more substituents independently selected from halo, $(C_1-C_4)$alkyl, hydroxyl, amino, $(C_1-C_4)$alkoxy, or $CF_3$.

One specific, non-limiting example of a compound having Formula VIII is compound 8H.

In various embodiments, the present invention provides for PKG inhibitor compounds represented by Formula IX and pharmaceutical compositions comprising said compounds:

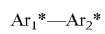  Formula IX wherein the following substituents are named with respect to Formula IX:

wherein X** represents, but not limited to, one of the following groups:

X** is:

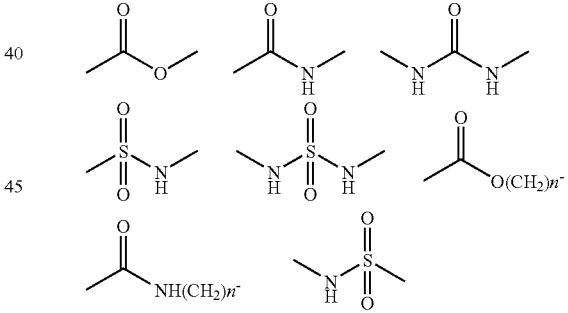

wherein n=1 to 4;

wherein Ar₁*=substituted or unsubstituted group, which include, but are not limited to, alkyl (e.g., $(C_1-C_4)$alkyl), aryl, alkoxy (e.g. $(C_1-C_4)$alkoxy), alkylcarbonyl (e.g., $(C_1-C_4)$alkylcarbonyl), furan, pyrrole, pyridine, phenyl, alkylphenyl, alkenyl (e.g. $(C_2-C_4)$alkenyl), alkynyl (e.g. $(C_2-C_4)$alkynyl), halo, or hydroxy, wherein the substitutent(s) of Ar₁* are optionally present and may be singular or plural, include one or more substituents independently selected from the following:

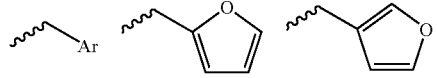

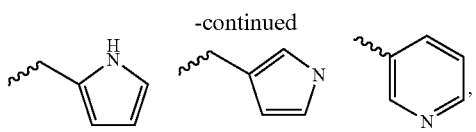

halo, $(C_1$-$C_4)$alkyl, hydroxyl, amino, $(C_1$-$C_4)$alkoxy, or $CF_3$;

wherein $Ar_2^*$=aryl, or heteroaryl, substituted or unsubstituted, for example:

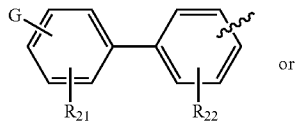

or

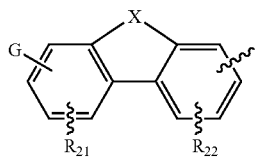

wherein G is H, $(C_1$-$C_4)$alkyl, hydroxy, $(C_2$-$C_4)$alkenyl, $(C_2$-$C_4)$alkynyl, halo, carbamoyl, amido, amino, cyano, $(C_1$-$C_4)$alkylcarbonyl, and $(C_1$-$C_4)$alkoxy; X is O, N, or S; $R_{21}$ and $R_{22}$ are respectively H, alkyl (e.g., $(C_1$-$C_4)$alkyl), aryl, alkoxy (e.g. $(C_1$-$C_4)$alkoxy), alkylcarbonyl (e.g., $(C_1$-$C_4)$alkylcarbonyl), phenyl, alkylphenyl, alkenyl (e.g., $(C_2$-$C_4)$alkenyl), alkynyl (e.g., $(C_2$-$C_4)$alkynyl), halo or hydroxy;

each of the aforesaid groups optionally having one or more substituents selected from the group consisting of halo, $(C_1$-$C_4)$alkyl, hydroxyl, amino, $(C_1$-$C_4)$alkoxy, and $CF_3$.

One specific, non-limiting example of a compound having Formula IX is compound 8J.

In various embodiments, the present invention provides for PKG inhibitor compounds and pharmaceutical compositions thereof comprising said inhibitors in amounts effective at inhibiting long-term hyperexcitability of sensory neurons, represented by Formula X:

*D* ring-*C* ring-*B* ring-*A* ring          Formula X wherein the following substituents are named with respect to Formula X:

wherein the D ring is a substituted or unsubstituted aromatic ring (for example, and not by way of limitation);

wherein the C ring is a substituted or unsubstituted aromatic ring (for example, and not by way of limitation);

wherein the B ring is a cycloalkyl, preferably a cyclopentyl, or pyrrolidine (for example, and not by way of limitation); and wherein the A ring is a substituted or unsubstituted aromatic ring (for example, and not by way of limitation).

The rings of Formula X are connected by various linkage groups, including but not limited to amide, ester, alkoxy, or ketone groups (for example, and not by way of limitation). Additional linkages groups contemplated by the invention are discussed below.

In particular embodiments, the PKG inhibitor compounds of Formula X are represented by Formula XI.

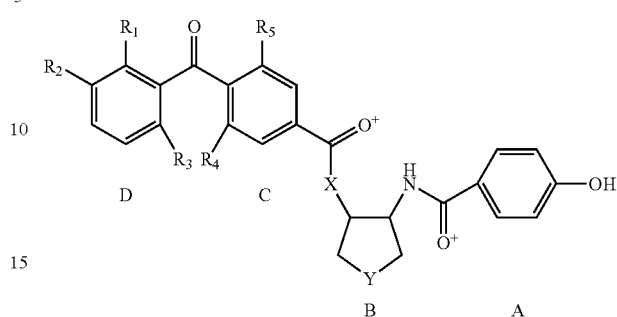

Formula XI wherein the following substituents are named with respect to Formula XI:

wherein $R_1$ may be F, COOH, Cl, or I, hydrogen, lower alkyl (e.g., straight chain, branched or cyclic moiety having 1-6 carbons), aryl, alkylamino, arlamino, aryloxy or alkoxy, preferably lower alkyl (for example, and not by way of limitation), wherein $R_2$ may be $CH_3O$, $CH_3CH_2O$, $(C_1$-$C_4)$alkoxy, or OH, hydrogen, lower alkyl (e.g., straight chain, branched or cyclic moiety having 1-6 carbons), aryl, alkylamino, arylamino, aryloxy or alkoxy, preferably lower alkyl (for example, and not by way of limitation), wherein $R_3$ may be a halogen, alkyl, aryl, cycloalkyl; alkoxy, cycloalkoxy (e.g. cyclo-pentane-O—, cyclo-pentane-$(CH_2)_n$—O—), allyl-O—, aryl-O—, amide(—NCO—R') sulfonamide(—$NSO_2R'$); alkylcarbonayl (—CO—R') $CH_3OCH_2O$, $CH_3CO$, $CH_3COO$, $CH_2OCH$, $O(CH_2)_2CH_3$, hydrogen, lower alkyl (e.g., straight chain, branched or cyclic moiety having 1-6 carbons), aryl, alkylamino, arlamino, aryloxy or alkoxy, preferably lower alkyl, COOH, COOR', $CONR'_1R'_2$, F, Cl, I,

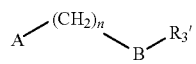

wherein n=0-5, preferably 1,2; and A,B=O,S,N,CH2, C=O, preferably O,N;

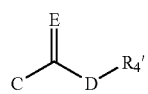

wherein C,D=O, N, S preferably O or N; and E=O,S, preferably O;

wherein F=O, S,N, $CH_2$, C=O, S=O, preferably O, N (for example, and not by way of limitation), wherein $R_4$ may be H, OH, $CH_3O$, or $(C_1$-$C_4)$alkoxy, lower alkyl (e.g., straight chain, branched or cyclic moiety having 1-6 carbons), aryl, alkylamino, arlamino, aryloxy or alkoxy, preferably lower alkyl (for example, and not by way of limitation), wherein $R_5$ may be H, OH, $CH_3O$, or $(C_1$-$C_4)$alkoxy, lower alkyl (e.g., straight chain, branched or cyclic moiety having 1-6 carbons), aryl, alkylamino, arylamino, aryloxy or alkoxy, preferably lower alkyl (for example, and not by way of limitation), wherein X may be O or N (for example, and not by way of limitation), and wherein Y may be N, NH or C (for example, and not by way of limitation), preferably Y is N.

In other non-limiting embodiments, the present invention provides for compounds having the structure of Formula XI, wherein the A ring may be

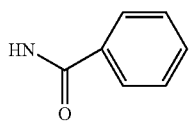

and wherein the A ring is connected to the B ring by an amide linkage as shown above.

In another non-limiting embodiment, the present invention provides for compounds having the structure of Formula XI, wherein the A ring may be

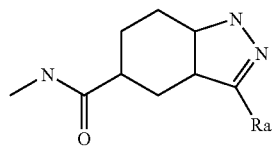

wherein $R_a$ may be an alkyl, alkoxy, substituted aromatic, $CH_3$, $CH_3O$, aromatic ring, $CF_3$, a halogen, or NHCO—$R_b$, and wherein the nitrogen of $R_a$ is linked to an alkyl sulfonamide, formyl, or acetyl group.

In other embodiments, the A ring of Formula XI may have up to 7 members.

In yet other embodiments, the ketones ($O^+$) of Formula XI are separated by 6 carbons, where there are 6 atoms carbonyl to carbonyl, with 4 atoms between the carbonyls.

In other non-limiting embodiments, the present invention provides for compounds having the structure of Formula XI, wherein the C and D rings may be:

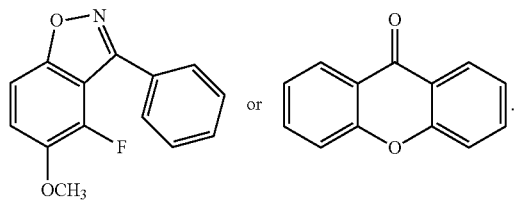 [SMILES: COc1ccc2onc(-c3ccccc3)c2c1F ; O=c1c2ccccc2oc2ccccc12]

In a preferred embodiment of a compound of Formula XI, $R_1$ is F and $R_2$ is $OCH_3$, wherein this particular embodiment has been shown to have high potency. The specificity of these embodiments is achieved by the diether group, which decreases activity.

In an alternative embodiment of a compound of Formula XI, where $R_1$ is not F and $R_2$ is not $OCH_3$, $R_4$ and $R_5$ are preferably OH groups.

In yet another embodiment of a compound of Formula XI, where $R_4$ and $R_5$ are OH groups $R_1$ is COOH and $R_3$ is OH. In another embodiment of a compound of Formula XI, where $R_4$ and $R_5$ are OH groups $R_1$ is OH and $R_3$ is COOH.

The compound of Formula XII (Compound-6) is a specific non-limiting example of a compound of Formula XI:

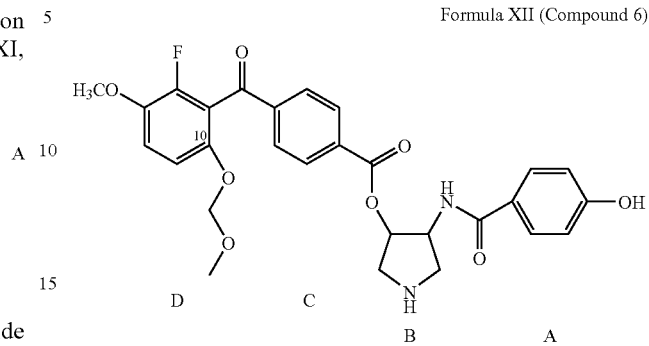

Formula XII (Compound 6)

The compound of Formula XIII (Compound-21) is another non-limiting example of a compound of Formula XI:

Formula XIII (Compound 21)

Figure 13A:
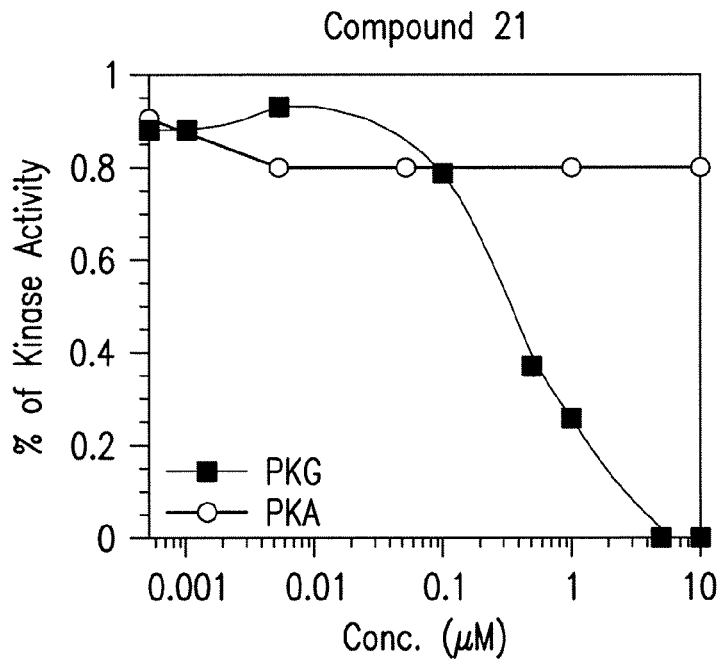
FIGS. 13A and 13B show the selective inhibition of PKG activity by increasing concentrations of compound 21 and compound 6.
Figure 13B:
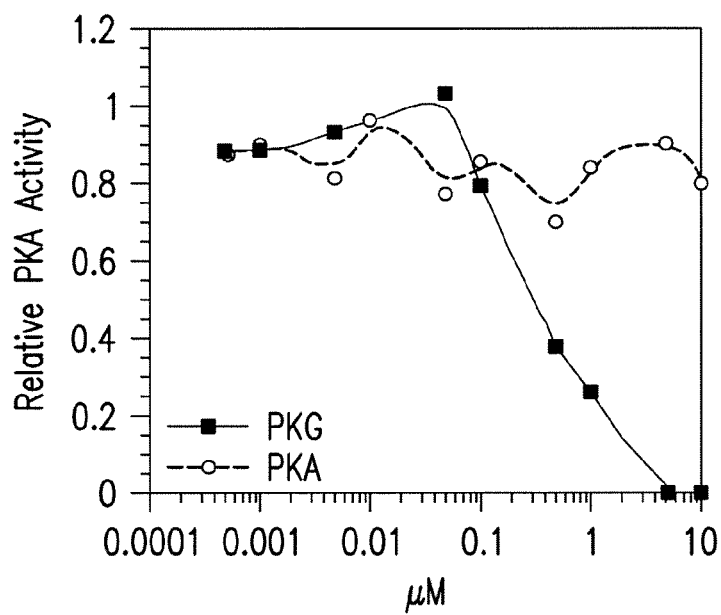
Figure 15A:
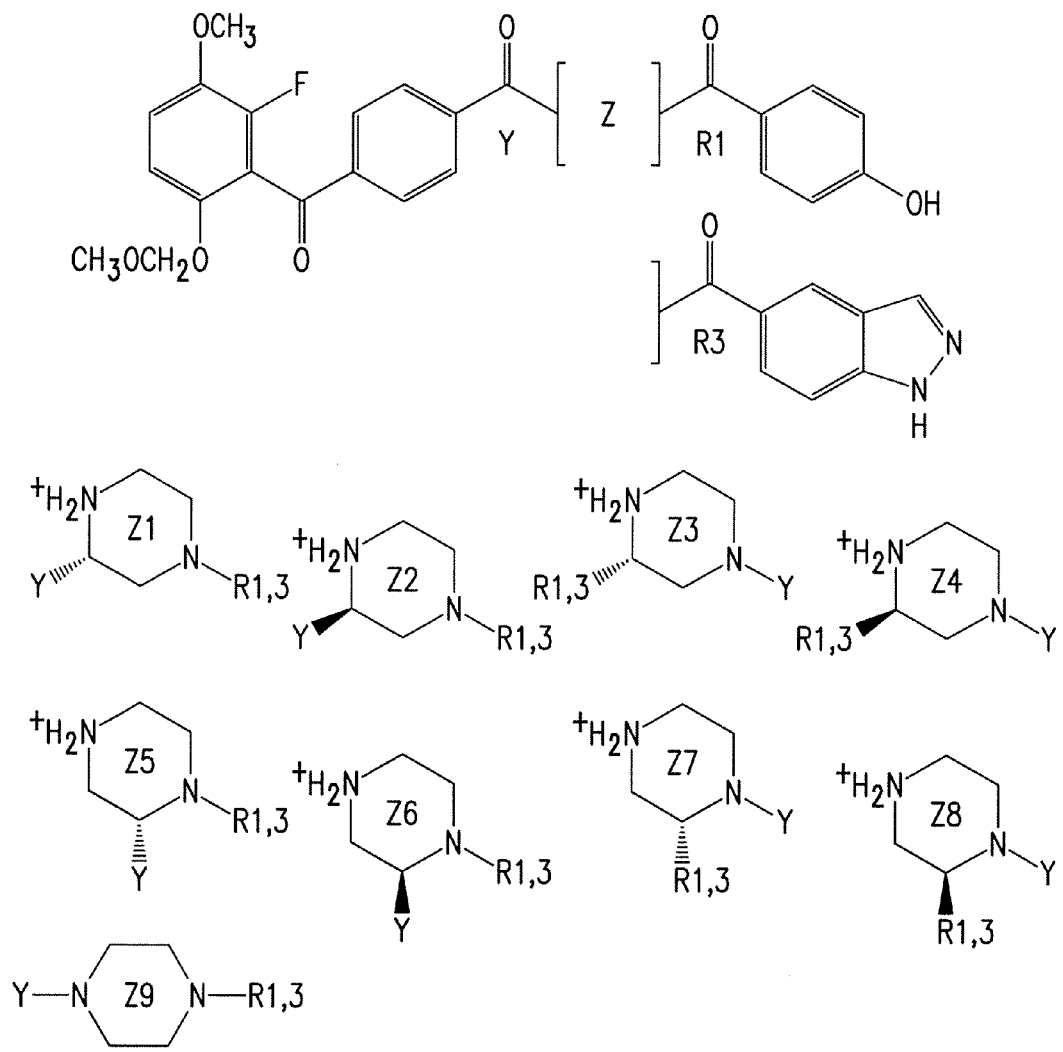
Figure 15B:
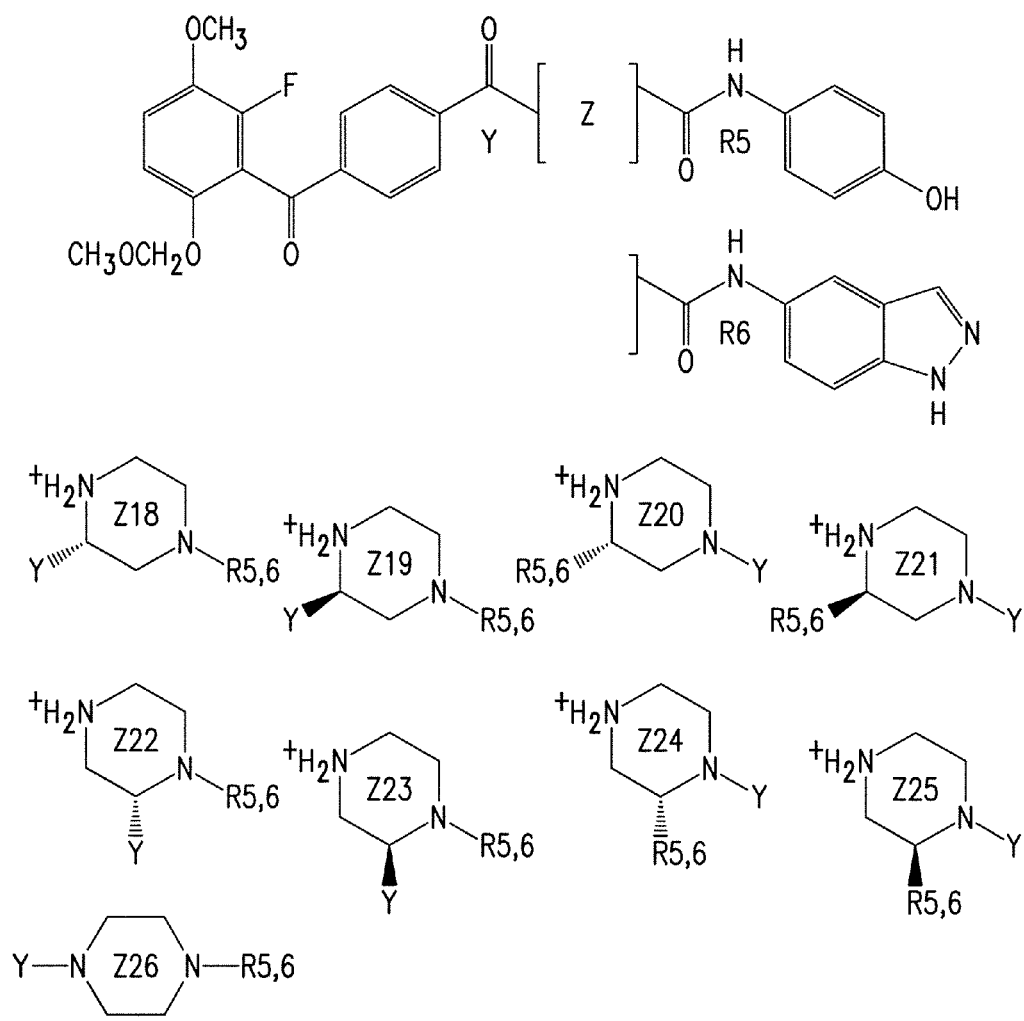
Figure 15C:
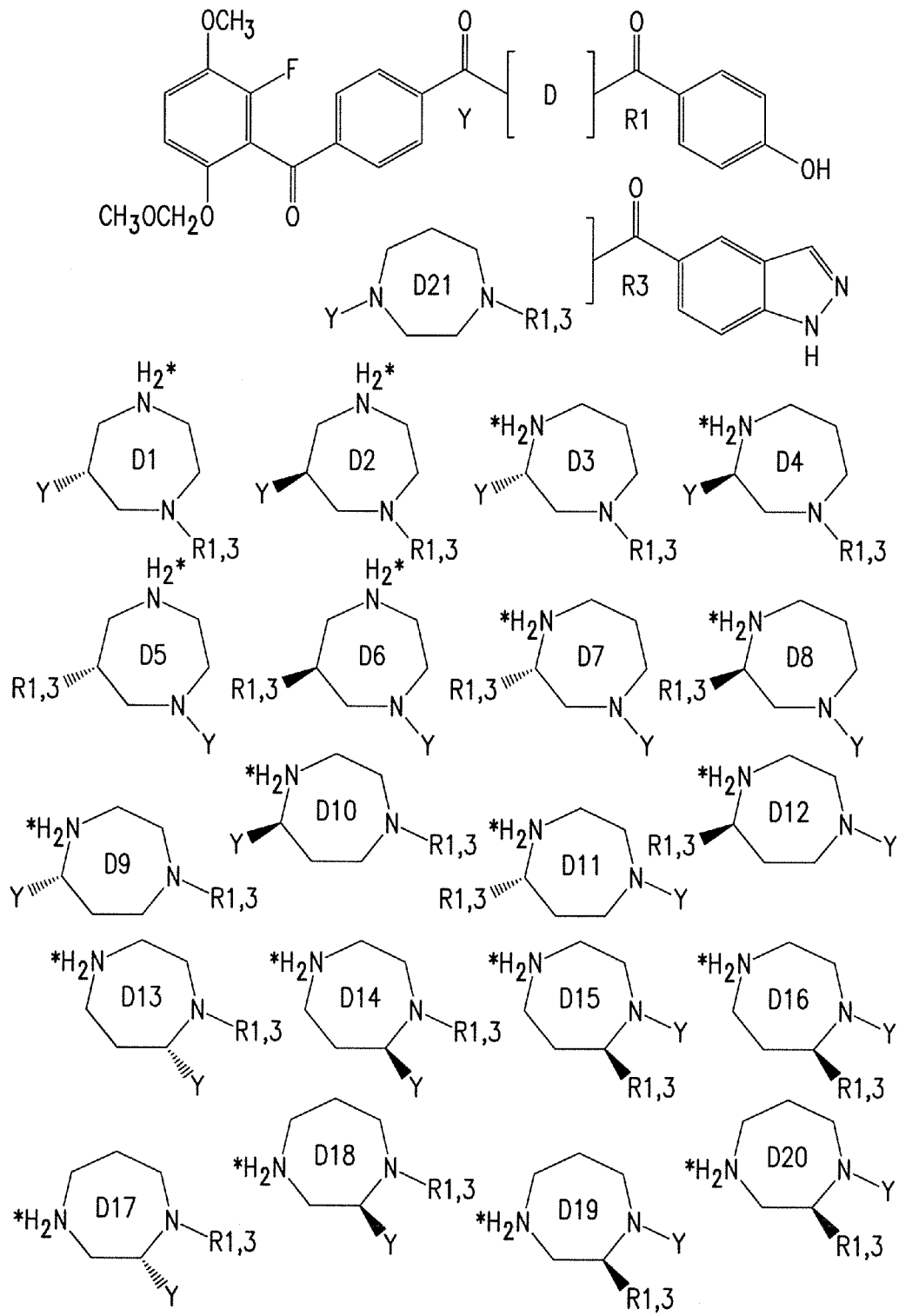
Figure 15D:
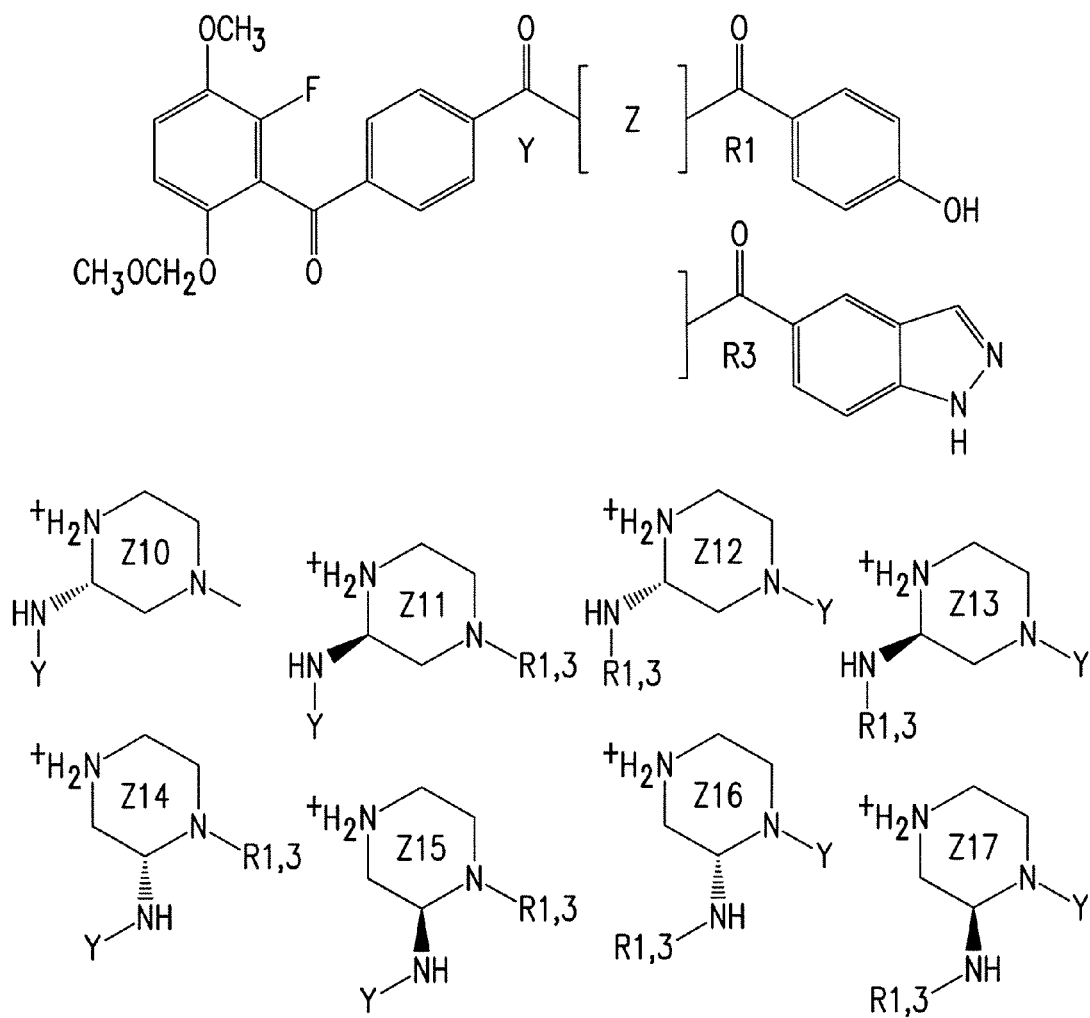
Figure 15E:
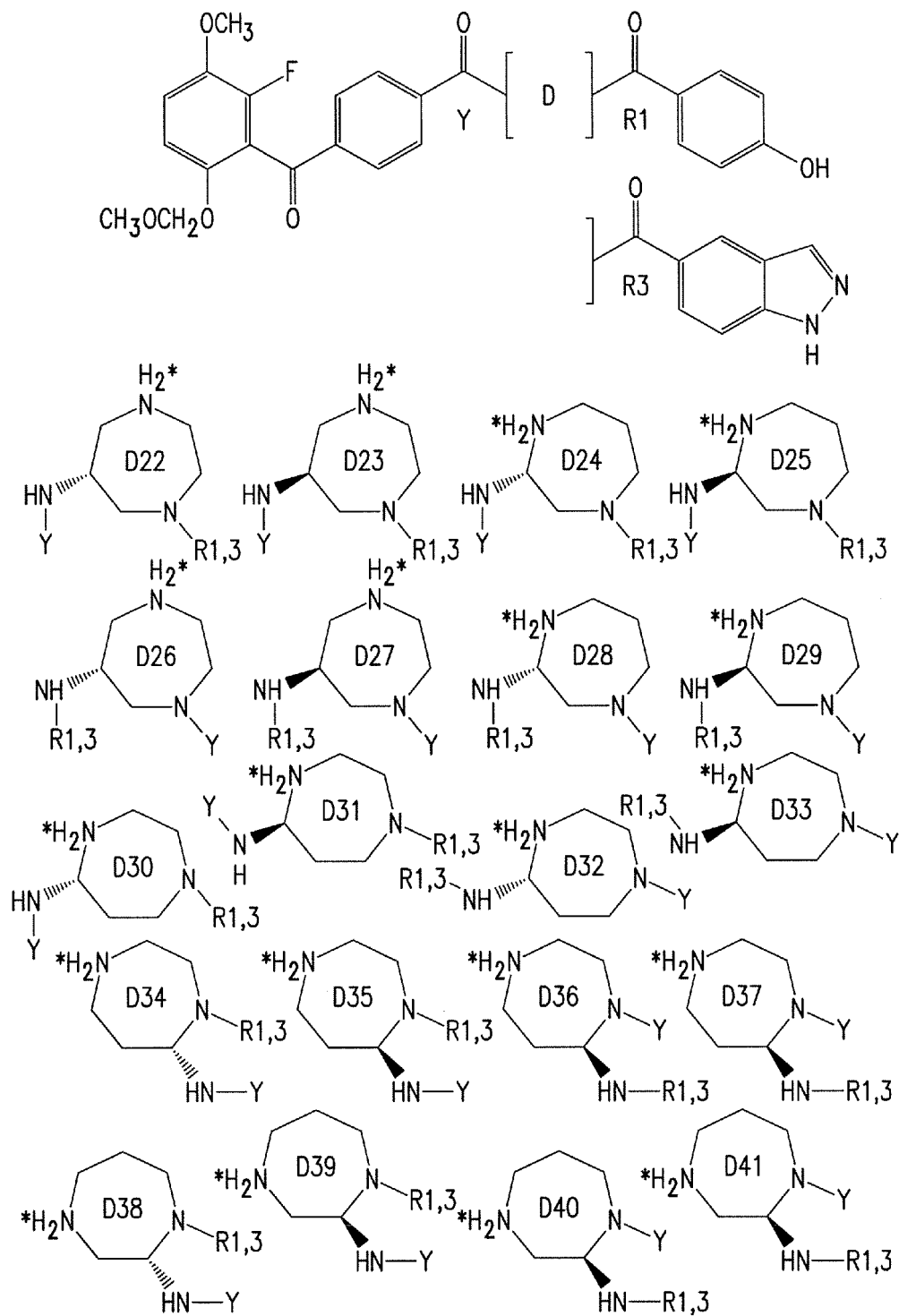
Figure 15F:
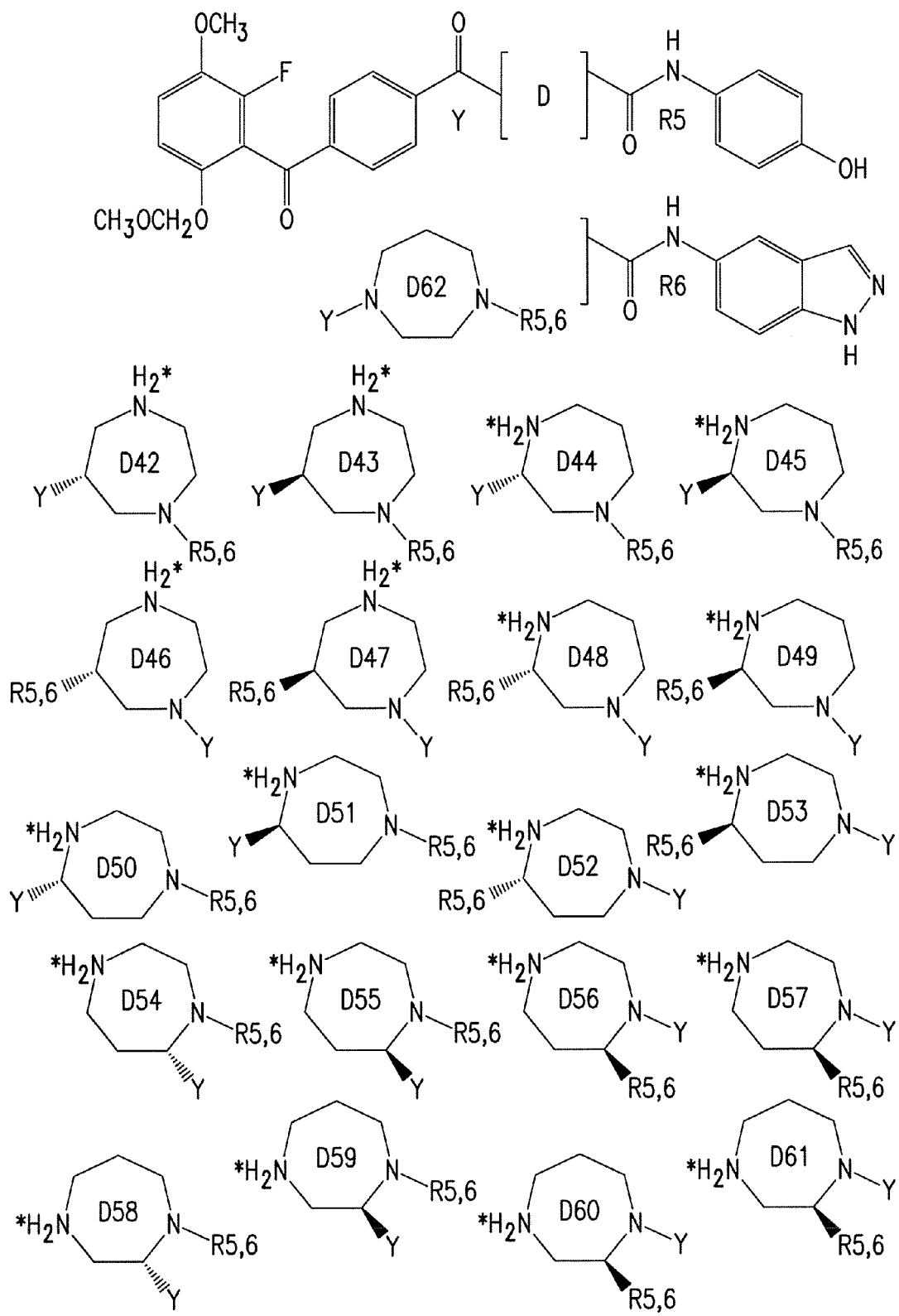
Figure 15G:
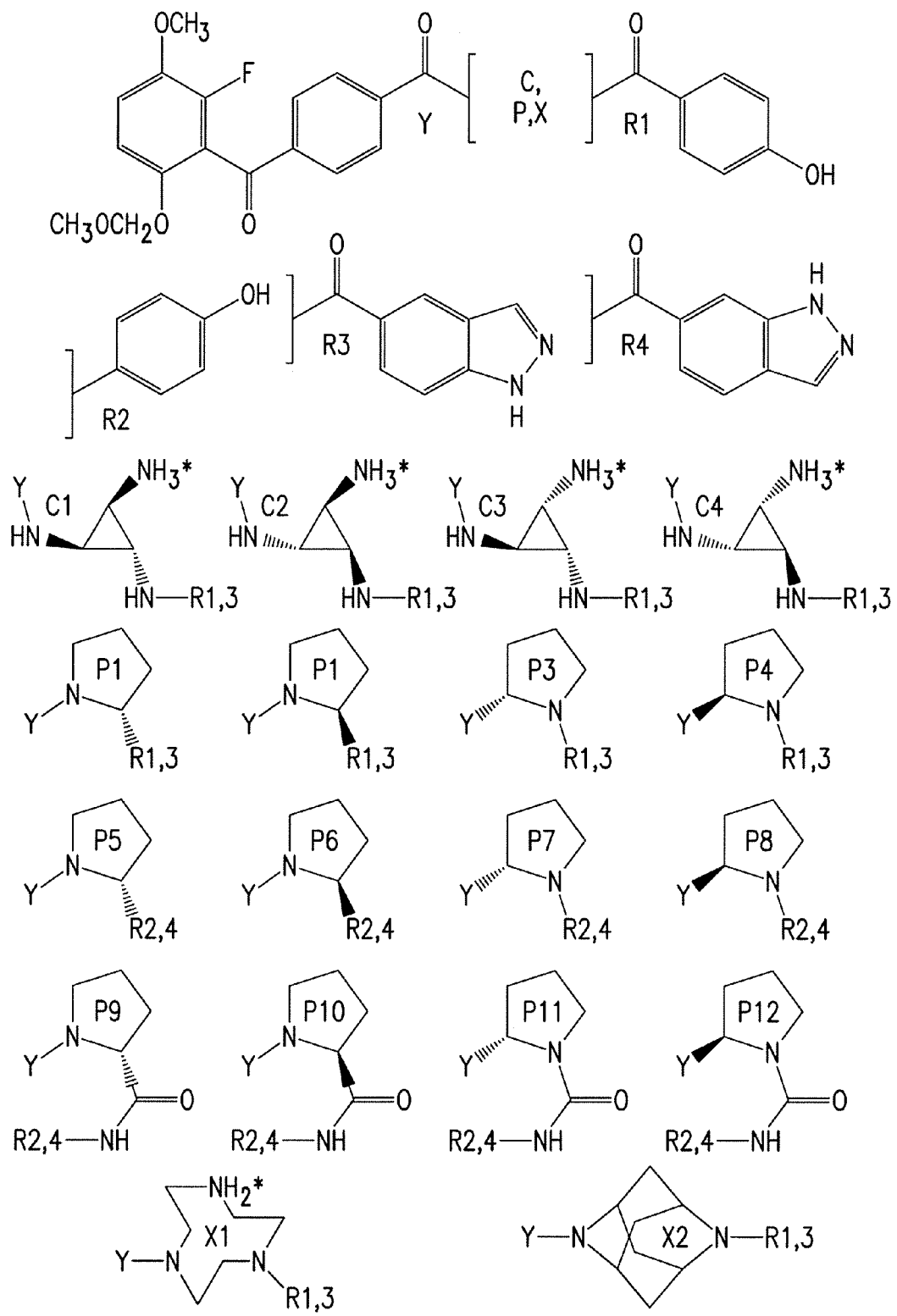
Figure 15H:
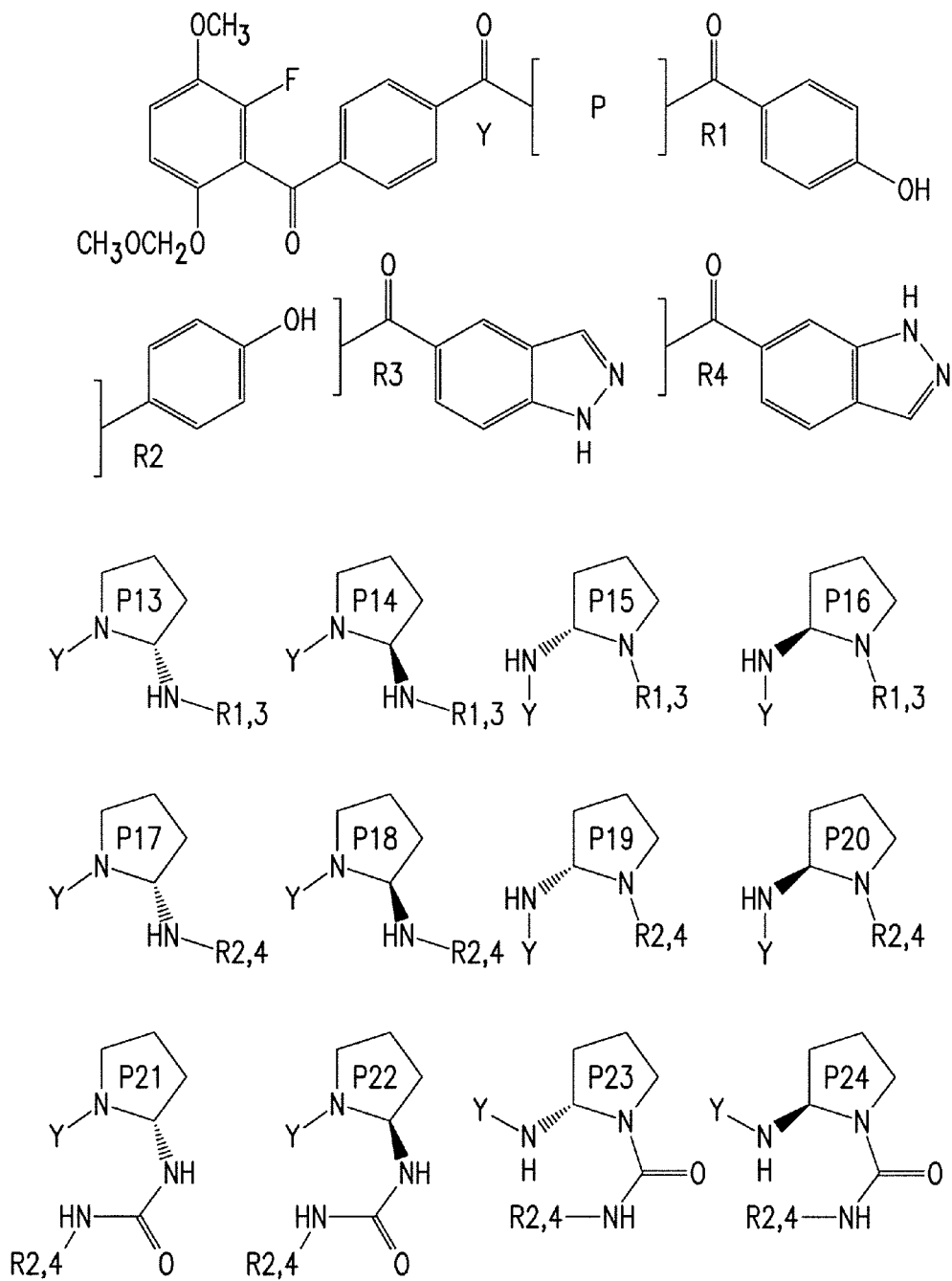
Figure 15I:
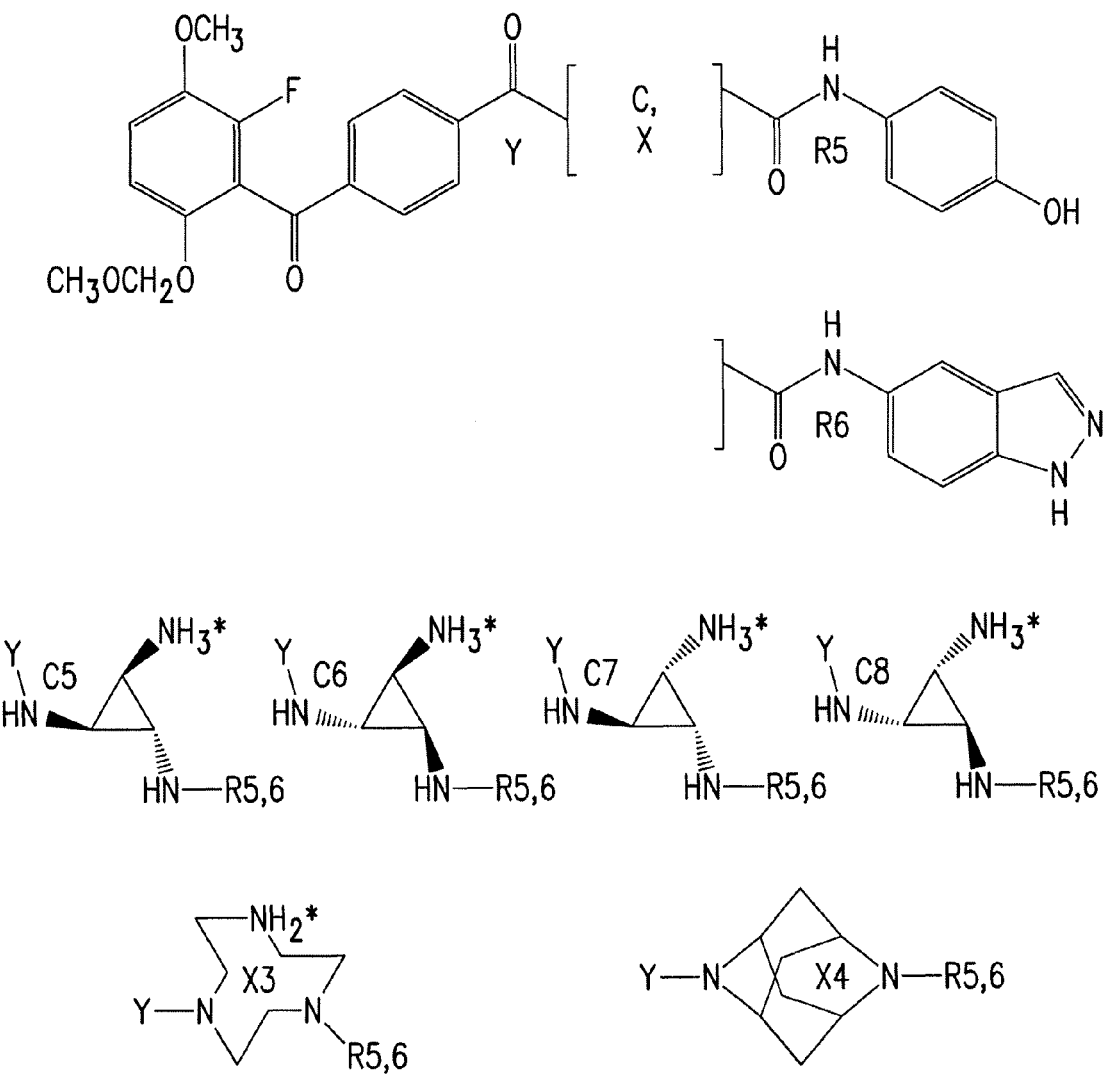
Figure 15J:
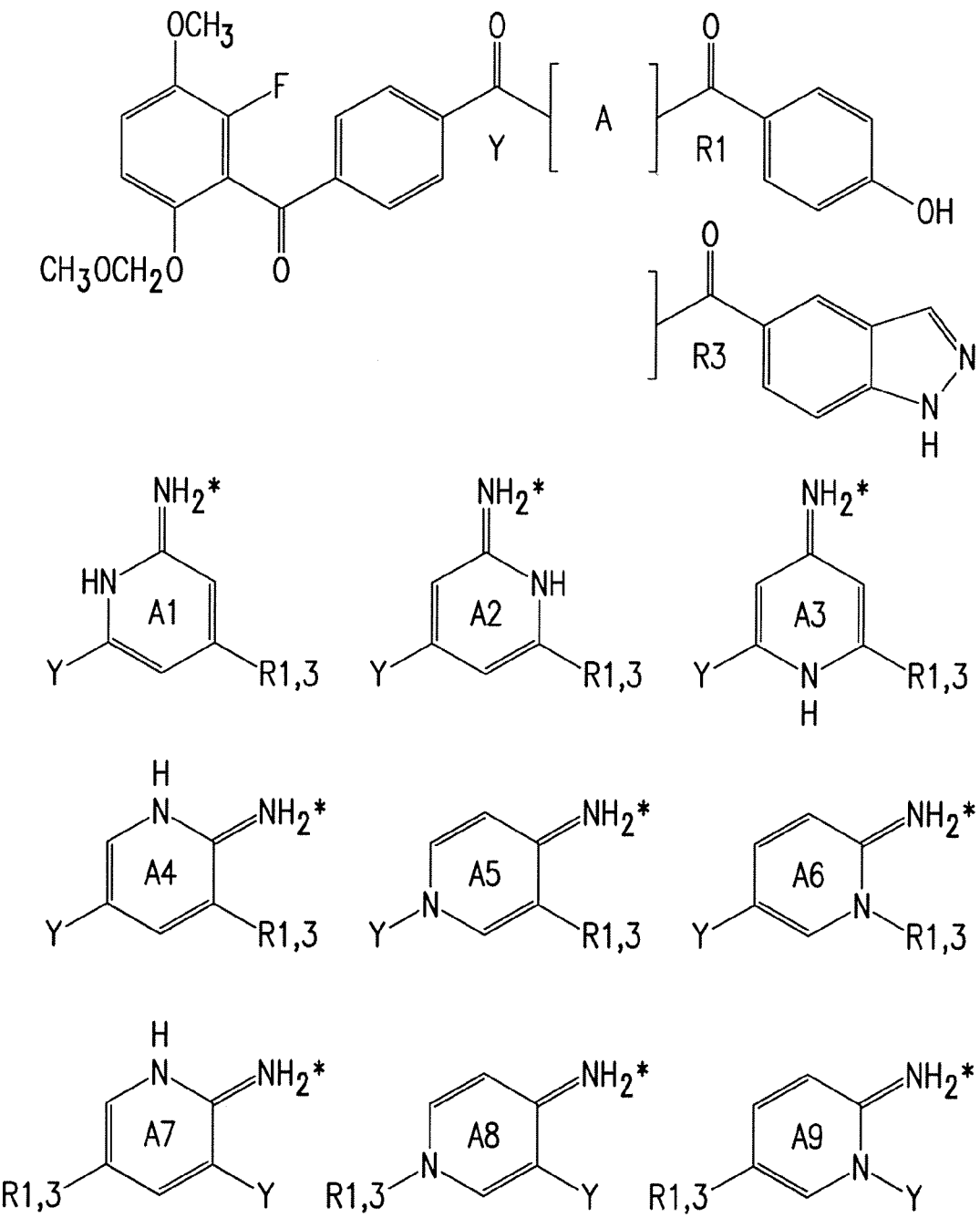
Figure 15K:
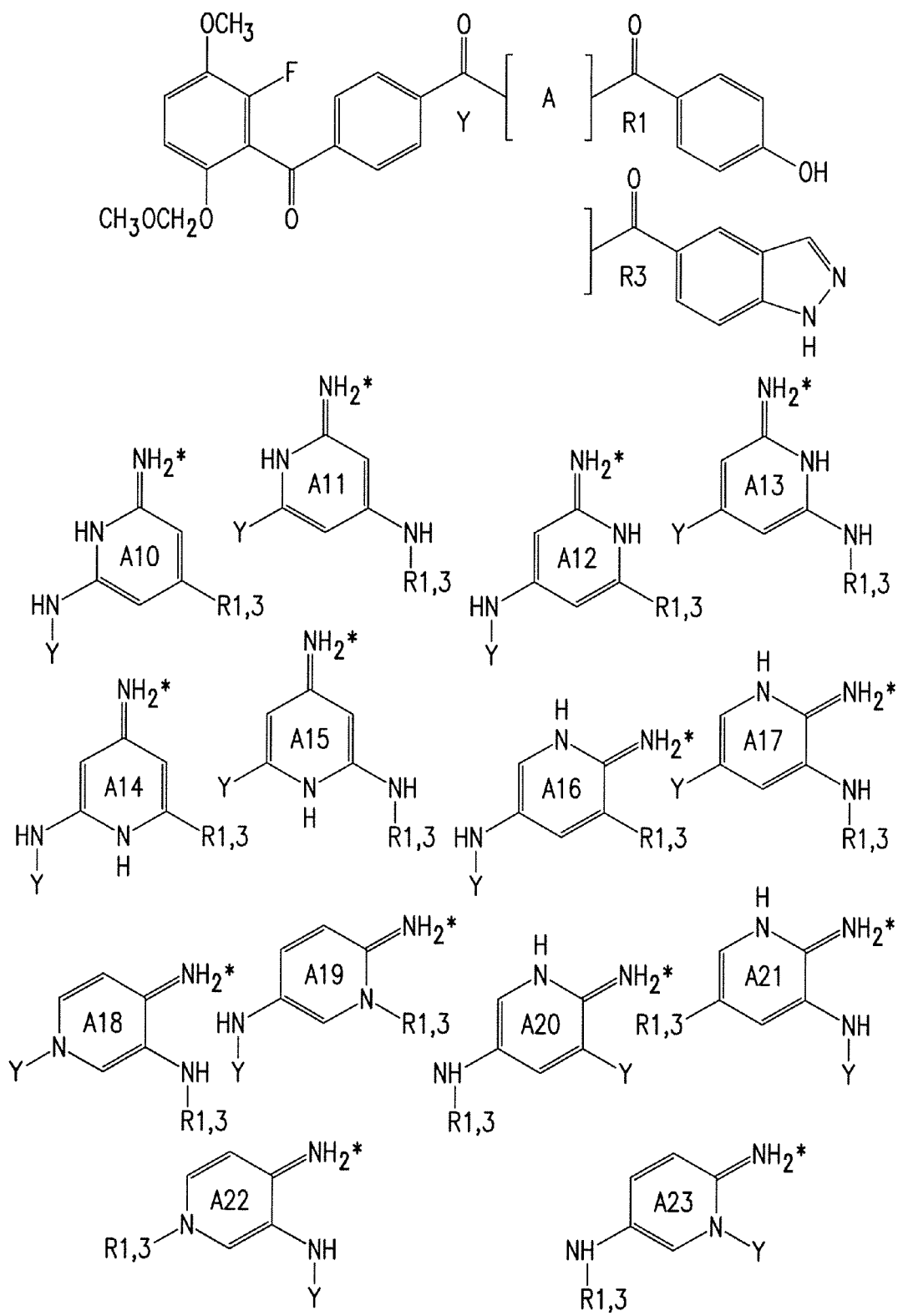
Figure 15L:
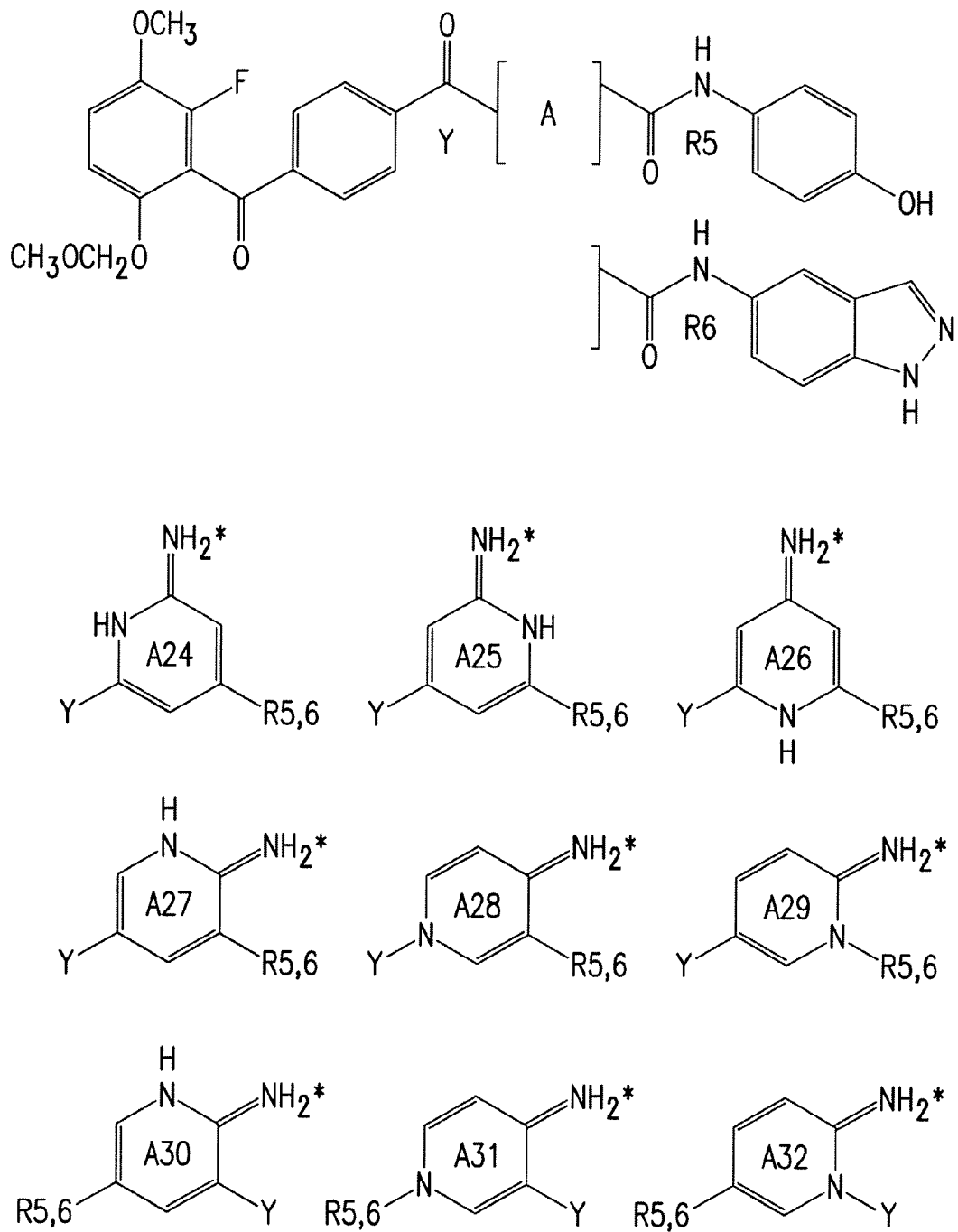

The activity of the compound of Formula XII has shown to have high selectivity for PKG versus PKA. Specifically the alkoxy substituent (at the 10 position) in the D ring of Compound 21 has been shown to account for improved selectivity. See FIGS. 13A and 13B.

In other non-limiting embodiments, the present invention provides for compounds having the structure of Formula XIII, wherein the substituent at the 10 position in the D ring may be $OCH_2CH=CH_2$, O-Cyclopropane, $OCH_2$-Cyclopropane, $OSO_2NR'$, $NHSO_2NR'$, NR''' wherein R''' are alkyl, cycloalkyl, or an aromatic substituent.

The compound of Formula XIV is another non-limiting example of a compound of Formula XI:

Formula XIV

Additional non-limiting examples of PKG inhibitor compounds contemplated by the present invention are identified in the Examples below.

In specific non-limiting embodiments of the invention, a modulator according to the invention binds more tightly to PKG than to other kinases, such as PKA, PKB, and/or PKC. Such modulators may, for example, selectively interact with particular amino acid residues found in PKG but not such other kinases (see FIG. 7). For example, the following residues are different between PKG and PKA: Gly370Ser (PKG amino acid/human PKG Type I alpha residue number/PKA amino acid), Ile406Thr, Val501Thr, Cys441Val, Ala440Tyr, Ile491Leu.

The present invention further provides for molecules of Formulas I-IX which are conjugated to one or more carrier peptide, one or more transport peptide, or one or more carrier peptide and one or more transport peptide (also referred to as balanol variants, or balanol double variants).

The present invention provides for pharmaceutical compositions comprising effective amounts of one or more compound having Formula I-IV, VI-XIV or otherwise described herein. An "effective amount" of compound is an amount which may be administered to produce an effective concentration of compound at the site of action, for example, the sensory neuron affected, wherein effectiveness refers to ability to inhibit PKG and/or produce a significant pain-inhibiting effect. In specific non-limiting embodiments, the concentration of a PKG modulator according to the invention administered to the neuron, for example via its axon, may be between about 1 and 500 nM, or between about 2 and 100 nM, depending on the potency of the compound.

In non-limiting embodiments of the invention, the concentration of a PKG modulator and in particular a PKG inhibitor disclosed herein in the peripheral blood of a subject being treated may be between about 1 nanomolar and 500 microM, or between about 100 nanomolar and 100 microM, or between about 1 and 500 nM, or between about 2 and 100 nM. For compounds of Formulas VIII and IX and compounds 8H (NOP479435) and 8J (NOP952668), the effective concentration may be, without limitation, between about 0.01 and 10 micromolar, and preferably between about 0.1 and 5 micromolar. For compounds of Formula X through XIII, the effective concentration in the peripheral blood may be, without limitation, between about 1 to about 100 nanomolar, and preferably between about 40 and about 70 nanomolar. For the compound of Formula XII (Compound 6), the concentration in the peripheral blood, may be without limitation, about 100 nM to about 500 microM, and preferably between about 100 nM and about 100 microM.

The present invention further provides for pharmaceutical compositions as follows. Compositions of the invention may comprise an inhibitor agent as described above, where the inhibitor agent optionally comprises a carrier molecule that facilitates its translocation through a neuronal cell or nuclear membrane. Examples of carrier molecules which may be used include but are not limited to HIV-1 tat protein (YGRKKRRQRRRPP; SEQ ID NO: 1) and peptides that are about 9-30 or about 9-20 residues long comprising its cores sequence RKKRRQRRR (SEQ ID NO: 2), *Drosophila* Antennapedia homeo-domain (RQIKIWFQNRRMKWKK; SEQ ID NO: 3). Other carrier molecules that may be used according to the invention may be largely comprised (contain at least 60 percent, at least 70 percent, or at least 80 percent) of positively charged amino acids such as arginine (Wender et al., 2000) and/or lysine (Mai et al., 2002). Also encompassed by the invention are peptides and derivatized peptides which are at least about 90 or about 95 percent homologous to the above-recited peptides, as determined using standard homology assessing software such as BLAST or FASTA. The inhibitor agent may optionally alternatively or additionally comprise a transport peptide, as described below.

The present invention provides for such inhibitor agents, in either lyophilized form or dissolved in a suitable pharmaceutical carrier. Compositions that comprise more than one inhibitor agent are encompassed by the invention.

In non-limiting embodiments, the invention provides for a pharmaceutical composition comprising one or more inhibitor agent, as set forth above, together with at least one agent that promotes uptake of the inhibitor agent into a peripheral nerve. Examples of such agents include membrane permeability enhancing agents such as dimethyl sulfoxide and/or 2 hydroxypropyl-b-cyclodextrin.

In other non-limiting embodiments, the invention provides for a pharmaceutical composition comprising one or more inhibitor agent, as set forth above, together with at least one agent that treats an underlying cause of the pain, including, but not limited to, an anti-inflammatory agent (such as aspirin, a non-steroidal anti-inflammatory agent such as ibuprofen, or a corticosteroid).

In other non-limiting embodiments, the invention provides for a pharmaceutical composition comprising one or more inhibitor agent, as set forth above, together with at least one agent having a local anesthetic effect, such as lidocaine.

In a further non-limiting embodiment, the present invention provides for a transdermal device, such as a patch or apparatus comprising one or more inhibitor agent, as set forth above, and optionally one or more additional agent which promotes the uptake of agent in a peripheral nerve, treats an underlying cause of the pain, and/or has local anesthetic effect, where exemplary compounds in each of these categories is provided above. The device may in general utilize transdermal patch technology known in the art to facilitate sustained release of its therapeutic agents through the skin of a subject. In specific, non-limiting embodiments, the device creates an electrical potential which promotes uptake of the inhibitor agent(s) into local tissue (iontophoresis) or improves drug transfer using ultrasound or radiofrequency waves (see Bryan, 2004; U.S. Pat. No. 5,405,614, U.S. Pat. No. 4,708,716).

5.2 Synthesis of Balanol-Related Modulators

Balanol structurally consists of three different parts: the tetra substituted benzophenone, the p-hydroxybenzamide moiety, and the perhydroazepine ring. This convenient analysis serves well as a guideline in planning the total synthesis of balanol and its analogs and also identified three major subjects of the SARs study of these interesting molecules. In the present invention, a systematic study of the SARs of balanol and its analogues was conducted with an aim toward uncovering factors that would allow the preparation of potent and selective PKG inhibitors.

As shown in a typical synthesis (see FIG. 16), preparation of balanol analogs followed a uniform scheme in which the azepine or its replacement was condensed with 4-hydroxybenzoyl residue or its replacements, and then coupled to a suitably protected benzophenone subunit followed by deprotection to give the final product. Specifically, benzoic acid 2 was converted to the corresponding acid chloride and coupled with an azepine replacement at the amino site. Occasionally this resulted in concomitant acylation of the vicinal hydroxyl group, and the crude products were treated with NaOH to provide the desire alcohols. For diamino compound 1 of FIG. 16, the formation of undesirable dimmer was unavoidable and the starting material could be recovered by harsh hydrolysis of diamides. Benzophenone acid 4 was usually converted to the corresponding acid chloride immediately before use and was coupled to amido alcohol or amido amine 3 of FIG. 16. With these common synthetic steps to complete the syntheses, the major task was reduced to construction of the desired three subunits. The synthesis of these required elements are shown in FIGS. 17A-E.

FIG. 17A shows the synthesis of the benzophenone subunit of balanol. Benzophenone acid 16 in FIG. 17A was prepared according to the literature method. As outlined in FIG. 17A, the differentially protected aryl bromide 8 was readily prepared from acid 7 in three steps. First, acid 1 was perbenzylated, and second, the benzyl ester was hydrolyzed and finally the acid was re-esterified. Benzyl alcohol 9 was metalated by reaction with n-butyllithium, and the resulting aryllithium was allowed to react with 1,2-dibromo-1,1,2,2-tetrafluoroethane to give aryl bromide 10. Bromo alcohol 10 was oxidized to aldehyde 11 with TEMPO and protected as cyclic ketal. The required 1,2,3-trisubstituted aldehyde 12 could then be generated by bromine-lithium exchange with n-butyllithium followed by a quench with DMF. Coupling of aryl bromide with aldehyde proceeded to provide carbinol 13 in moderate yield. The ketone could conveniently be generated by oxidation of alcohol with manganese dioxide. The resulting benzophenone was then deprotected by p-TSA-catalyzed acetal hydrolysis to afford the corresponding aldehyde 14. Aldehyde 14 was oxidized with sodium chlorite to carboxlic acid. Benzylation and tert-tutyl deprotection as usual provided the desired benzophenone acid 16.

FIG. 17B shows the synthesis of the simplified benzophenone subunit. Compound 18 in FIG. 17B was conveniently prepared from commercial available 3-fluoro-4-methoxyacetophenone through Baeyer-Villiger oxidation followed by deacetation and subsequent protection with MOM group. MOM-directed ortholithiation followed by aryllithium addition to commercially available aldehyde 19 provided barbinol 20 in moderate yield. Similarly, Oxidation of barbinol 20 with active manganese dioxide gave the crucial intermediate 21. Unmasking the carboxyl group of 21 with NaOH afforded acid 22. To introduce the desired side chain R, 21 was first treated with HCl to remove MOM group and introduction of R followed by the treatment of NaOH gave the desired benzophenone acid 24. Benzisoxazole acid 25 was prepared from benzophenone 23 by a three-step sequence in which oxime formation was accomplished with hydroxyl-amine in ethanol and dehydration with diethylazodicarboxylate and triphenyl phosphine followed by hydrolysis of the methyl ester furnished the final product 25. See FIG. 17B.

As shown in FIG. 17C, mCPBA epoxidation of olefin 26 followed by stereospecific epoxide opening with sodium azide and reduction afforded the trans-vicinal amino alcohol 29. Condensation of (+)-L-tartaric acid with benzylamine provided homochiral 3,4-dihydroxypyrrolidinedione, which was easily reduced to the respective enantiopure (3S,4S)-dihydroxylpyrrolidine 30 with LiAlH4. Debenzylation in the presence of Boc2O afforded the Boc-protected Diol 31. Diol 31 was transformed into its mesyl diester followed by azide substitution and subsequent catalytic reduction to give the enantiopure N-tBoc-(3R,4R)-3,4-diaminopyrrolidine 32. See FIG. 17D.

As shown in FIG. 17E, carbon substitutions in the 3-position of the indazoles was achieved by anion addition of Grignard reagents to 5-bromo-2-fluorobenzaldehyde 33. The resulting alcohol was oxidized with manganese dioxide to give the corresponding ketone 34. The indazole 35 was then formed by refluxing the ketone in hydrazine. Bromine-lithium exchange with n-butyllithium followed by a quench with dry CO2 yielded the indazole acid 35. The unsaturated N atom of indazole acid was often protected with Ac before its coupling with other amines. All compounds were prepared in racemic form, with the exception of diamide compounds.

5.3 Methods of Use of Modulators of PKG

A PKG inhibitor of the invention may be administered to a sensory neuron in need of such treatment in an amount effective in inhibiting LTH. Where the SN to which the inhibitor is to be administered is a SN in vivo in an animal subject, the inhibitor may be administered systemically (e.g. by intravenous injection, oral administration, inhalation, etc.), may be injected locally (in proximity to the damaged nerve), may be applied topically (for example, together with a skin permeability enhancing agent, such as a chemical compound or an electrical stimulus, optionally in the form of a sustained-release transdermal patch) or may be administered by any other means known in the art. In preferred non-limiting embodiments, the compound would not be administered directly into the central nervous system (for example, via intrathecal administration). However, in other embodiments, administration into the central nervous system (e.g. by intrathecal administration or by access to the central nervous system of drug administered by another route) may be appropriate, either alone or in conjunction with delivery to the peripheral nerve and/or systemic administration.

The amount of inhibitor to be administered may be determined using methods known in the art, for example, by doing dose response studies in one or more model system, such as the *Aplysia* system described above or a mammalian model of peripheral neuropathic pain, followed by approved clinical testing in humans. Where concentrations are set forth below, they refer to the concentration to which the sensory neuron or any component thereof, including axon, cell body or receptor, is exposed.

In related embodiments, an effective amount of an inhibitor may be administered to a subject in need of such treatment, where the subject suffers from chronic pain. The chronic pain preferably has a peripheral nervous system (primary) hyperalgesia component, where the method inhibits pain mediated by the peripheral nervous system, but in specific non-limiting embodiments the present invention also encompasses the treatment of spinal hyperalgesia as either a component of or the basis of (e.g., chronic central neuropathic pain resulting from spinal cord injury) chronic pain. Any of the foregoing modes of administration may be used, but if a spinal hyperalgesia component is to be treated, the inhibitor, which is directed to a neuron having its cell body in the central nervous system and not in the dorsal root ganglion, should be administered intrathecally.

An effective amount is an amount of inhibitor which decreases the level of pain subjectively perceived by the subject, preferably amount determined, in controlled experiments, which is greater than placebo effect. For example, and not by way of limitation, in certain embodiments of the invention, where perceived pain can be quantified on a scale from 0 to 10, where 0 is no pain, 1-5 is progressively more intense mild pain, 6-7 is progressively more intense moderate pain, 8-9 is progressively more intense severe pain, and 10 is the worst pain possible (to the subject), an effective amount of inhibitor may decrease the pain scale quantification of perceived pain by at least 2 points, or by at least 3 points.

In specific, non-limiting embodiments, the present invention provides for a method for treating chronic pain in a subject comprising administering, to the location from which the pain arises, an effective amount of an inhibitor as set forth herein (alternatively referred to as an "LTH inhibitor"), where administration can be by local injection or topical application (e.g. via a cream, ointment, or transdermal device, which may be a patch or may be an apparatus or an apparatus containing or otherwise associated with a patch), and the location can be, as non-limiting examples, a wound site, tissue overlying an inflamed joint, or an area within the dermatome associated with the perceived pain (e.g., L4, L5, S1, C3, C4, C5, C6 or C7, see below and FIG. 3).

In specific, non-limiting embodiments, the present invention provides for a method for treating post-operative pain in a subject comprising administering an effective amount of an inhibitor as set forth herein. Since the PKG is activated at a peripheral site, an incision on the skin should sever the surrounding sensory nerve endings resulting in the local activation of the NOS-sGC-PKG pathway. Subsequently, active PKG is transported along the axotomized sensory axons to the corresponding DRGs, initiating the development of hyper excitability and concomitantly pain. Therefore, the use of PKG inhibitors may be an effective means of treating post-operative pain.

The present invention provides for a method for modulating and specifically inhibiting pain pathways comprising a PKG inhibitor compound as set forth herein to an axon of a sensory nerve such that the compound is retrogradely transported along the axon to the nociceptive sensory neuron cell body in the dorsal root ganglion. In one non-limiting example, the transport peptide is PKKKRK (SEQ ID NO: 4), or a peptide or derivatized peptide which is at least about 80 percent homologous thereto as determined using standard homology assessing software such as BLAST or FASTA and which facilitate axonal transport. In another non-limiting example, the transport peptide is the related peptide CTPP-KKKRKV (SEQ ID NO: 5) (see Ambron, 1992), or a peptide or derivatized peptide which is at least about 70, at least about 80, or at least about 90 percent homologous thereto as determined using standard homology assessing software such as BLAST or FASTA and which facilitate axonal transport. In specific, non-limiting embodiments of the invention, the transport peptide is between 5 and 20 amino acids long and comprises the peptide KKKRK (SEQ ID NO: 6), PKKKRK (SEQ ID NO: 4), PPKKKRK (SEQ ID NO: 7), TPPKKKRK (SEQ ID NO: 8), or PKKKKRKV (SEQ ID NO: 9).

Figure 1A:
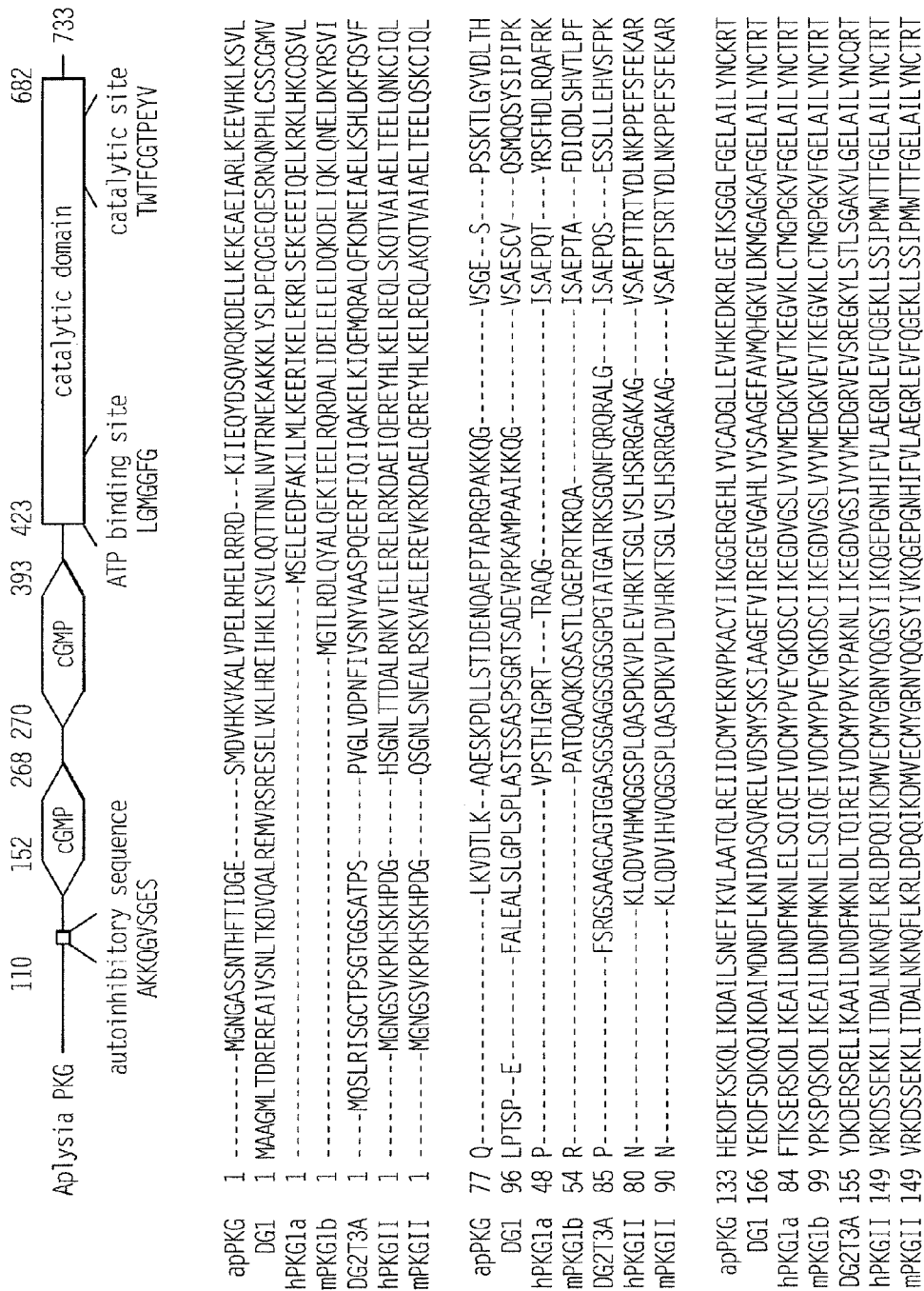
Figure 2A:
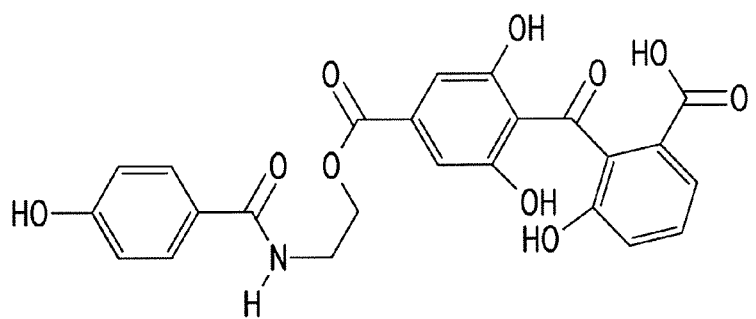
Figure 2B:
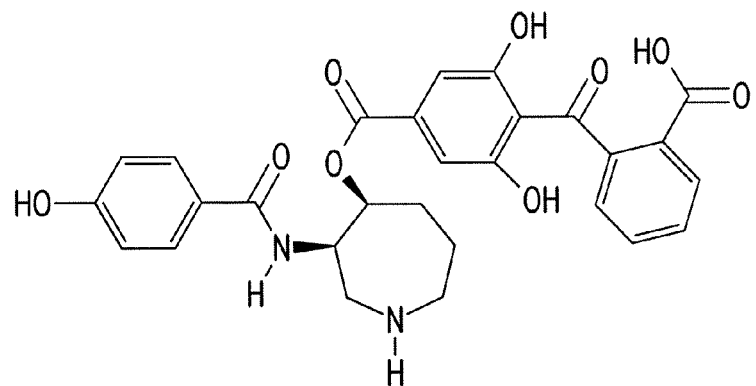
Figure 2C:
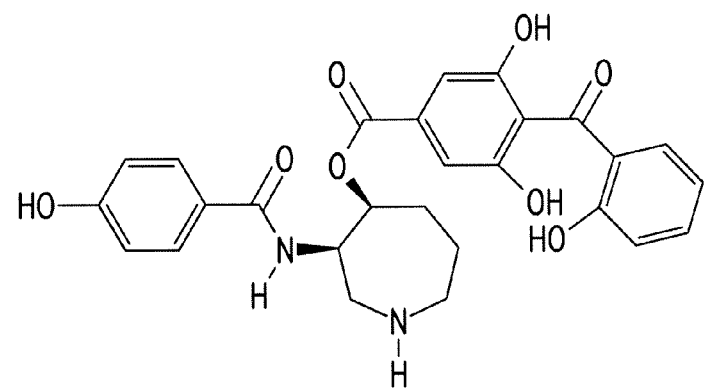
Figure 3A:
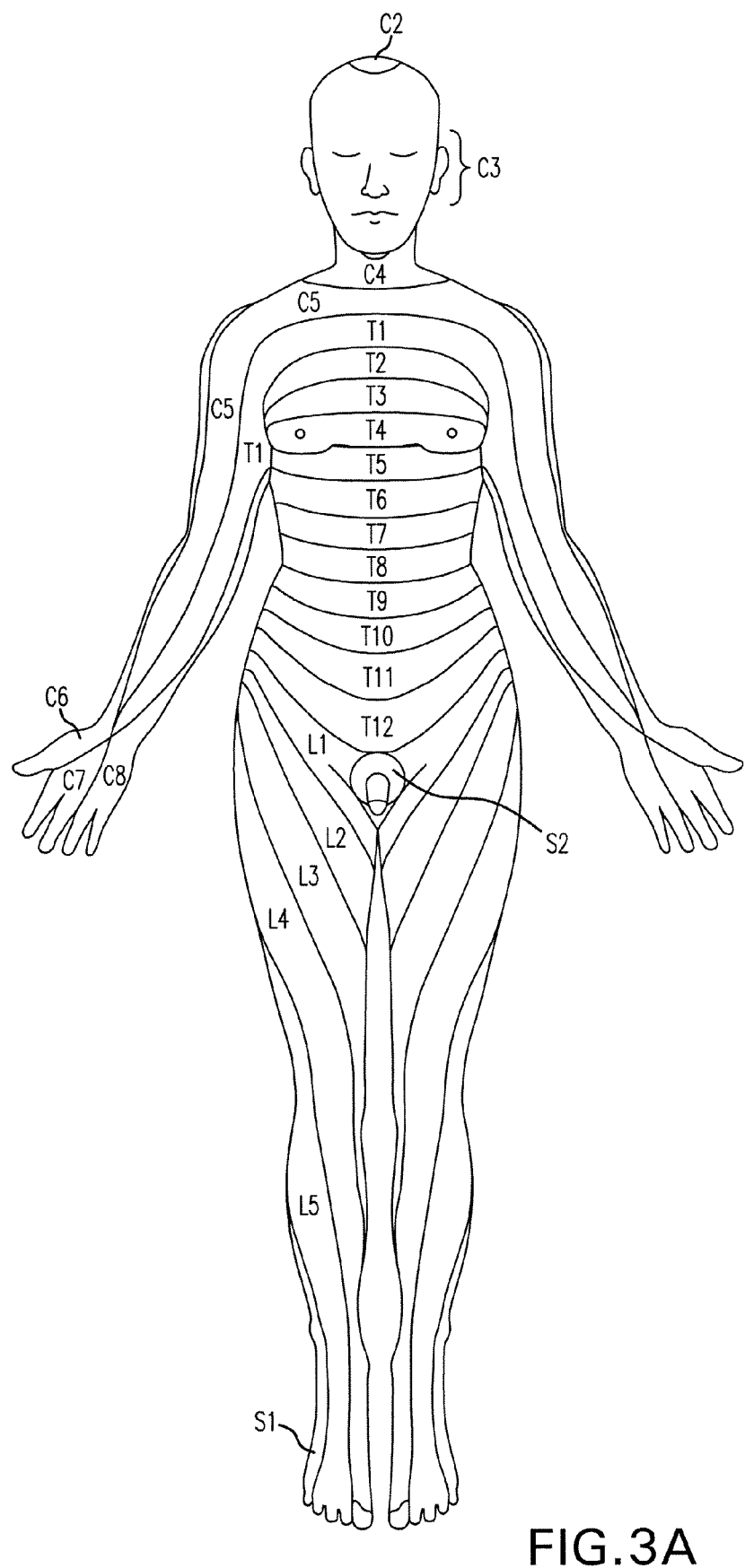
Figure 3B:
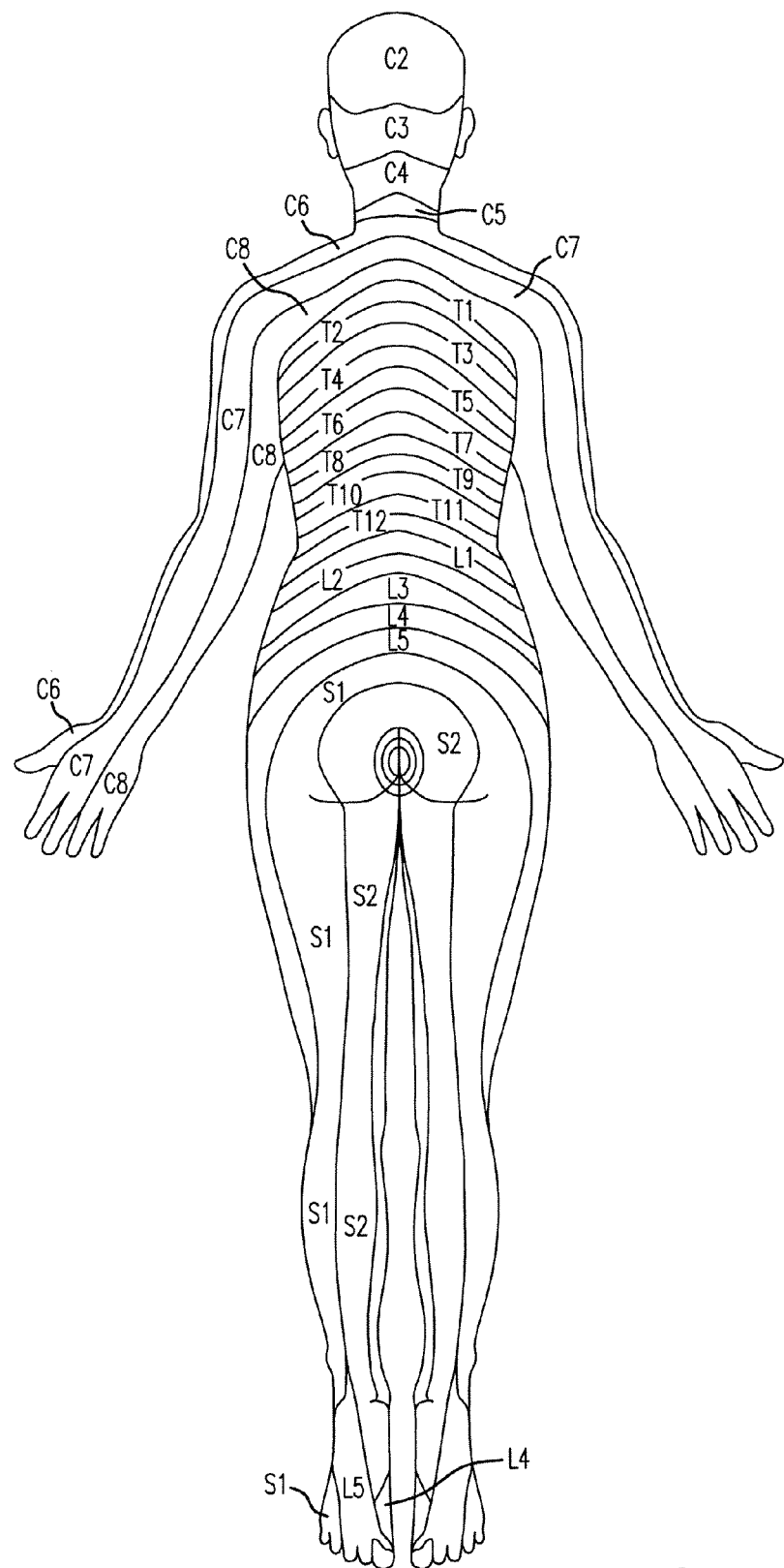

For example, the PKG inhibitor compound comprising a transport peptide may be delivered to a peripheral pain receptor at the site of injury or in the same dermatome as the injury, as sensory axons arising throughout the dermatome converge on the same dorsal root ganglion. FIG. 3A-B presents the sensory dermatomes (from The Merck Manual of Diagnosis and Therapy, Section 14, Chapter 165, FIG. 165-2, which references Keegan J J and Garrett F D, "Anatomical Record 102:409-437, 1948, used with permission of the Wistar Institute, Philadelphia, Pa.). As examples, arthritis pain associated with the fingers is communicated via axons whose cell bodies reside in DRGs at levels C5-T1 and pain from the knees is communicated via axons whose cell bodies reside in DRGs at levels L3-S2.

Accordingly, the present invention provides for a method of treating pain in a subject, where the pain is determined to be associated with a dorsal root ganglion at a particular spinal cord level, comprising topically applying a PKG inhibitor comprising a transport peptide to skin lying within the dermatome corresponding to the spinal cord level associated with the pain.

A PKG inhibitor compound may be comprised in a cream, ointment, or transdermal device (see above), applied to the appropriate dermatome.

For example, a person suffering from lower back pain as a result of compression of the nerve exiting a bony foramen in the lower spine (lumbar, sacral, or lumbosacral radiculopathy) could be treated with a transdermal patch containing a PKG inhibitor compound (comprising a transport peptide) applied to the dermatome corresponding to the spinal cord level from which the compressed nerve originates, which may be identified by the person's symptoms and physical exam. As one specific example, because the radiculopathy often involves nerves that supply the L4, L5 and/or S1 dermatomes, a transdermal patch according to the invention may be applied to the appropriate region of the thigh or leg of the patient. As another specific non-limiting example, a person having arthritis involving the finger joints, dermatomes C6-C8, could wear a patch according to the invention on the upper arm or shoulder.

5.4 A PKG Model System

The present invention provides for assays that identify modulators (inhibitors or promoters/inducers) of PKG. Such assays may be used to evaluate a test agent in order to determine whether the test agent is an agent that modulates PKG and thereby modulates LTH. An inhibitor of PKG may be used to inhibit LTH and may be used to inhibit and/or treat (lessen, delay or prevent) persistent pain in a sensory neuron and/or a subject. A promoter/inducer of PKG may be used to develop a model system for persistent pain, preferably in an animal which, like *Aplysia*, is believed to not subjectively experience pain.

The assays of the invention utilize homology models of PKG built based on crystal structures of the ATP catalytic domain of PKA with balanol and a balanol analog (1BX6 and 1 SVE, respectively). Putative modulators of PKG were then identified by docking 3-dimensional structures of commercially available drug-like small molecules to the foregoing PKG homology models.

Once a compound is identified as putatively binding to the PKG active site ("a putative modulator"), it may be tested for physiologic activity in a suitable model system. One non-limiting example of a suitable model system comprises a test sensory neuron ("TSN") under physiological conditions that at least approximate the in vivo environment in which the sensory neuron exists in nature. The TSN comprises a cell body that contains the nucleus as well as an axonal segment, which constitutes at least a portion of the TSN's axon and more preferably constitutes the complete axon. In certain non-limiting embodiments, the TSN is an *Aplysia* SN. In other non-limiting embodiments, the TSN is a vertebrate SN, preferably a mammalian SN. The TSN may be maintained isolated in a culture, as part of a group of neurons that may or may not all be SNs, or as an explanted nerve or section thereof (e.g., an excised segment of rat sciatic nerve). In alternate embodiments, the TSN may be retained in an animal in vivo. In still further non-limiting embodiments, the axonal segment may contain at least one ligation.

To test the activity of the putative modulator in said model system, the TSN may be injured. For example, and not by way of limitation, the injury may be created by crushing, cutting and/or chemically injuring the TSN using methods known in the art. Other methods include inducing an inflammatory response, ischemia, a reduction of the blood supply to neurons, and hyperglycemia. The putative modulator may be administered to the TSN, either prior to, concurrent with, or following injury, either comprised in culture medium, systemically administered, locally injected, or directly injected or otherwise introduced into the TSN. In non-limiting embodiments, the putative modulator may be administered to a particular cellular location of the TSN, such as the cell body or the axon. Preferably, the effects of the putative modulator on the TSN are compared to comparable values in a control SN ("CSN"), such as an injured CSN. Preferably within 48 hours of injury, the assay of the present invention determines whether the putative modulator modulates protein kinase G ("PKG") activity in an injured TSN, preferably relative to PKG activity in an injured CSN to which test agent has not been administered. An ability to inhibit PKG activity associated with SN injury indicates that the test agent is an LTH inhibitor. An ability to promote a further increase in PKG activity relative to control values indicates that the test agent is an LTH promoter. PKG activity may be measured, for example and not by way of limitation, by measuring the kinase activity in a SN extract. For example, the amount of PKG activity in a SN extract may be determined by measuring transfer of $^{32}$P from [$^{32}$P]-ATP to BPDEtide (Calbiochem, La Jolla, Calif.). Further, electrophysiologic testing may be performed to determine whether the putative modulator modulates the development of LTH in the injured neuron, as compared to a control, injured neuron not exposed to putative modulator.

5.5 Linkers to Modify the Lead Compound

The most active known PKG ligands have a chemical structure involving a linker:

(tail)Ar—C:O—Ar—C:O—X-linker-Y—Ar(head)

The linkers known to work well at PKG have had at their core a saturated alicyclic or aliphatic ring, such as azepane (in balanol), cyclopentane and pyrrolidine, connected in a trans-substituted arrangement via ester or amide to the tail and via an amide to the head (X and Y above). The main function of the linker is to provide the appropriate distance and angle between the head and tail, while remaining compatible with the size, shape, and electrostatic properties of the receptor in this region. If the linker is positively charged, it may make also make a salt bridge with anionic sidechains bordering the pocket. The goal in designing new linkers is to retain or improve the activity by retaining the right spatial and geometric characteristics, and to find new linkers that are convenient to use.

With numerous possibilities to investigate, one could specify rings with some similarities in terms of charge and size to the known rings, using medicinal chemistry and from looking at the binding mode of the known ligands at PKG. For consistency, and to limit the size of the search space, one tail end can be the focus, however, the combinatorics is easily expanded to different tails. Certain rings that can be tested include, but are not limited to, aminocyclopropane, aminopyridine, piperazine, diazepane, proline. Additional larger rings or cages with nitrogens (triazacyclononane, diazaadamantane), by way of example, can also be tested to determine if they fit. Each of these rings has several substitution points, which means there are many possible combinations, including stereochemistry. Rings could also be joined directly via a C—C bond, or via an amide —N—C:O— or —C:O—N— (See FIGS. 15A-L and Example 10 below).

In designing linkers, if the ring has a nitrogen, it may be synthetically convenient to link directly to that nitrogen via an amide, removing a stereocentre and making the system generally easier to handle. Simultaneously varying the head group from phenol to indazole is also of interest, since prior screens have turned up an active indazole, which is novel as a PKG inhibitor chemotype, and in many cases the tests showed superior scores when docked to the binding site.

Thus, having defined the space to investigate, the possibilities are enumerated into a 156×2 virtual combinatorial library (See FIG. 14). These are then converted into low energy three dimensional models using standard techniques (Monte Carlo conformational searching, MMFFs and OPLS2005 forcefields).

Previously, structures were prepared of the catalytic domain of PKA from the PDB: structures 1bx6, 1sve and 1rek, all of which have balanol or balanol analogues bound. Likewise, using comparative homology modelling in Schrodinger's Prime software, corresponding PKG(1bx6), PKG (1sve) and PKG(1rek) models were prepared. Scores from docking ligands to such models using Schrodinger's Glide XP docking-and-scoring software provides a positive correlation between score and experimental affinity. While the correlation is not perfect, this allows a large set of potential ligands to be prioritized for synthesis and testing. In particular, this is a good method for increasing the efficiency of resource usage by ruling out what not to make and test (e.g., prolines are not necessarily promising).

Each candidate in the virtual combinatorial library is docked with Schrodinger's Glide XP software four times (in four input conformations) to each of the above six receptors or receptor models. This provides thorough sampling of both the ligand and protein conformational flexibility, and a best score to be obtained. The raw scores are modified by a term that takes account of the ligand strain energy according to OPLS2005 forcefield. The purpose of adding the strain energy is to penalize linkers that need to fold into a high energy conformation or transfer that energy to the protein in order to bind, and thus would take a hit in terms of their affinity. The final result is prioritization of all of the structures in the library, in terms of their scores at PKG, their preference for PKG over PKA, and whether the phenol or indazole head performs better with that particular linker. This same method was carried with a smaller library to list priorities for swapping out the acid-labile methoxymethyl group on the tail of the selective lead compound Compound-6.

6. EXAMPLE

Modeling of PKG and Identification of Putative Modulator Compounds

6.1 Method A—Homology Model Generation and Ligand-Receptor Docking

Two homology models of PKG were generated at Schrödinger Inc. (Portland, Oreg.; New York City, N.Y.) from structures of PKA co-crystallized with balanol and a balanol analog, 1bx6 and 1sve, using the protein structure prediction package Prime (version 1.5102) (http://www.schrodinger.com/; Jacobsen et al., 2004). Approximately 100,000 commercially available drug-like compounds were virtually screened against these homology models using increasingly accurate modes of the docking algorithm Glide (version 4.0108) (Friesner et al., 2004; Halgren et al., 2004). Compounds were selected for purchase and biological screening based on their resultant extra precision (XP) GlideScores and a brief visual inspection of the structures for chemical reasonableness.

6.2 Method B—Similarity Analysis and Docking

Balanol was used as a probe to search a database of approximately 1.3 million commercially available compounds to identify similar compounds. Similarity was calculated using the atom-pair similarity measure described by Carhart et al. (1985) where atom pairs are defined in terms of the atomic environments of, and shortest path between, all pairs of atoms in the topological representation of the chemical structure. A similarity cutoff of 0.55 identified 4 compounds which were docked against the aforementioned PKG homology models using the XP mode of Glide (Friesner et al., 2004; Halgren et al., 2004). Two compounds were selected for purchase and biological screening based on their XP GlideScores and brief visual inspection.

6.3 Results

Figures 4A, 4B:
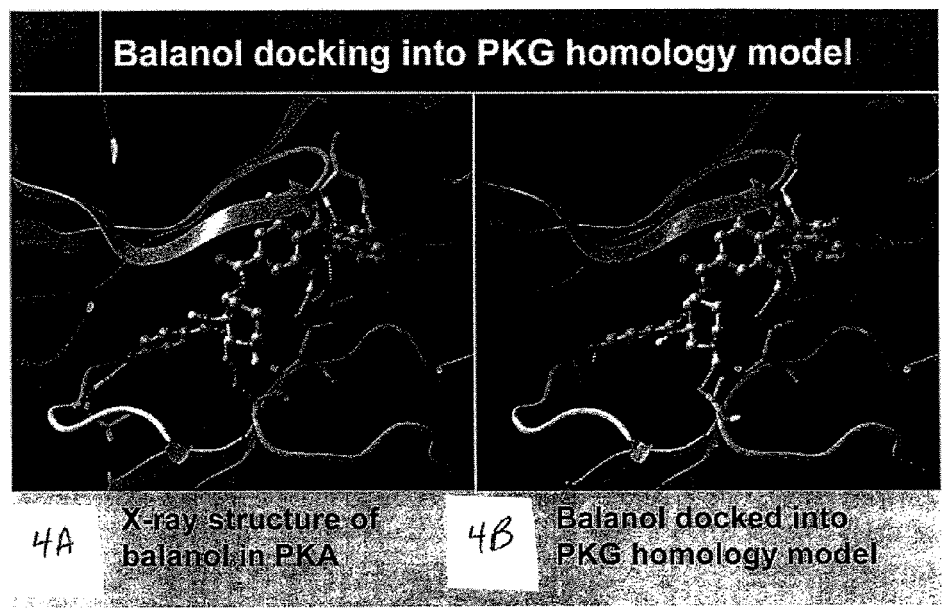
Figure 5B:
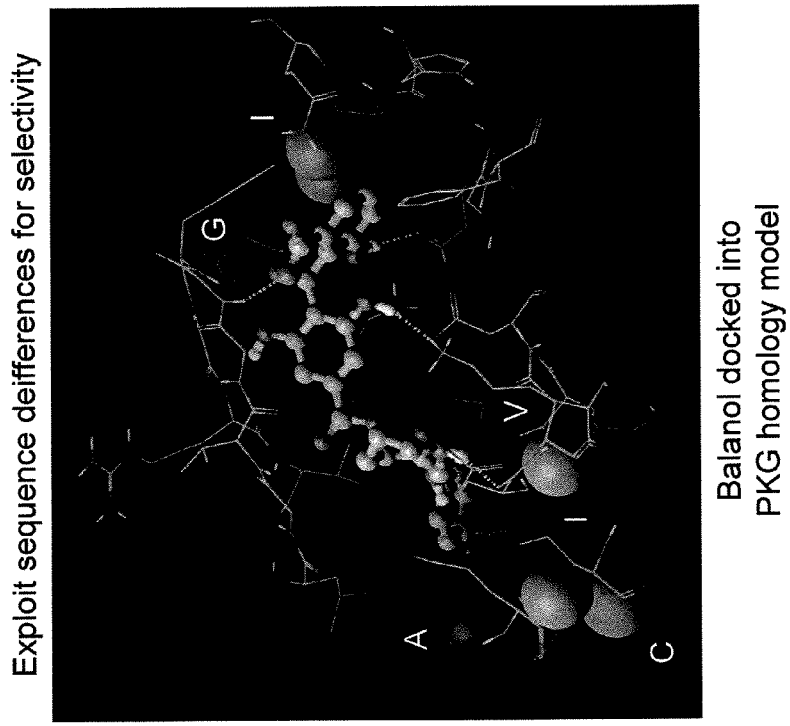
Figure 5A:
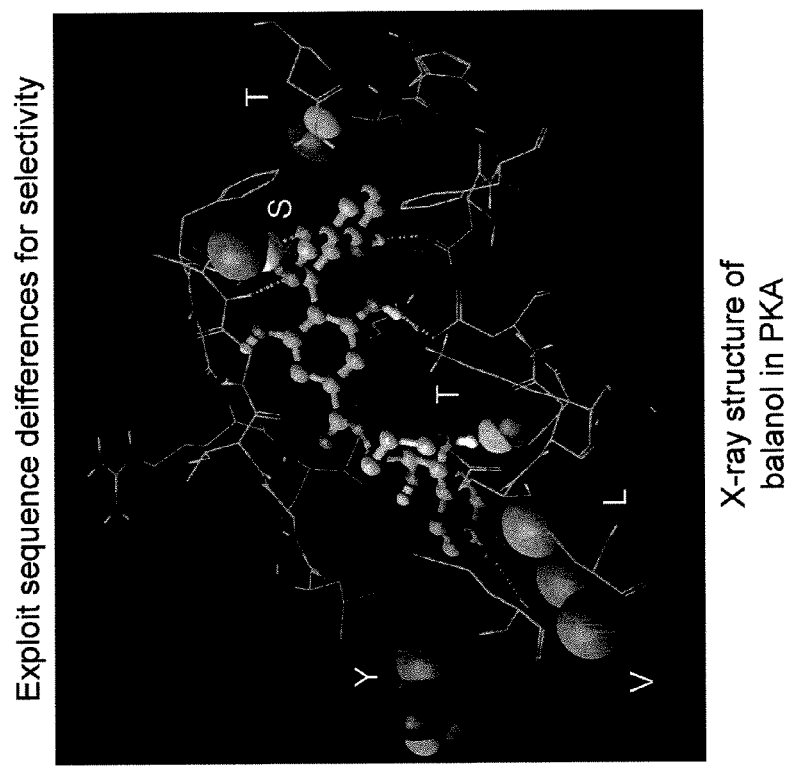

Using Method A above, two homology models of PKG were generated. Docking balanol to these structures produced docked poses very similar to that seen in the crystal structure of balanol bound to PKA [see FIG. 4A (1BX6) and FIG. 4B (balanol docked into PKG homology model based on 1BX6)]. FIGS. 5A-B and FIG. 7 highlight the residues that are different in PKG and PKA/PKB/PKC, and thus can be exploited in the identification and design of PKG selective modulators. For example, the residues that are different between PKG and PKA are: Gly370Ser (PKG amino acid/human PKG Type 1 alpha residue number/PKA amino acid), Ile406Thr, Val501Thr, Cys441Val, Ala440Tyr, Ile491Leu. A number of compounds were identified by docking as being predicted to be modulators of PKG, the structures of which are depicted in FIGS. 8C-L. These molecules are referred to herein as compounds 8C-8L, respectively. FIGS. 9A-K depicts the docked poses of various compounds and PKG, including balanol (FIG. 9A) and compounds 8C-8L (FIGS. 9B-K).

Further, using Method B, compounds 8A-8B were identified by atom-pair similarity followed by docking to the homology model of PKG based on 1 BX6 (FIGS. 8A-B). FIG. 6 shows a series of cyclopentane analogs of balanol.

7. EXAMPLE

Selection of Compound 6 as a PKG Inhibitor Drug Candidate

7.1 Methods

Two building blocks were required to make Compound 6: Benzofenone acid and the linkage with para-hydroxy benzene ring. Each block required 5 steps to make them respectively as discussed below. In total, there was a convergence of 13 steps to make Compound 6. See FIG. 19.

Acetic acid 3-fluoro-4-methoxy phenyl ester

A mixture of 25 g (0.15 mole) of 3-fluoro-4-methoxyacetophenone (1) and 40 g (0.2 mole) of 85% 3-chloroperoxy-benzoic acid in 350 ml of methylene chloride was refluxed for 48 h, cooled and washed with 5% potassium carbonate solution (200 ml) three times. The organic phase was dried with $MgSO_4$ and the solvent was evaporated. The product (24 g, 87.0%) was used next step without purification.

3-Fluoro-4-methoxyphenol 20 g of 2 (0.11 mole) obtained above was dissolved in 200 ml of ethanol and 100 ml of 20% of NaOH was added slowly. After addition, the reaction was stirred at room temperature for 3 h. The aqueous solution was washed with ether and acidified with 6N HCl. The oil which separated was extracted into ether and the extracts dried with $MgSO_4$. Removal of the solvent left a solid residue which was recrystallized from hexane to give 13 g product (83.3%)

2-Fluoro-1-methoxy-4-methoxymethoxy-benzene

A mixture of 3.0 g (21 mmole) of 3 and 7 ml of N,N-diisopropylethylamine (73 mmole) was dissolved in 100 ml of methylene chloride. To this solution cooled with ice-water bath, 0.3 ml of Chloromethyl methyl ether (39.5 mmole) was added dropwise. After addition, the reaction was stirred at room temperature for 3 h. After removing solvent, the residue was purified by chromatography on silica gel (elute with methylene chloride) to give 3.9 g product as light yellow oil (100%).

4-[(2-Fluoro-3-methoxy-6-methoxymethoxy-phenyl)-hydroxy-methyl]-benzoic acid methyl ester 10 ml of 1.6M of n-BuLi in THF (16 mmole) was added to 2.5 g of 4 (13.4 mmole) in 50 ml of dry THF at −78° C. The solution was stirred at the same temperature for 40 minutes. To this solution, a solution of 2.2 g of 4-Formyl-benzoic acid methyl ester (13.4 mmole) in 50 ml of dry THF was added by canal slowly (internal temperature was kept under −65° C.). The reaction was stirred at −65° C. for 6 h and the reaction was allowed to warm up to room temperature in 15 h. The reaction was quenched with water and extracted with ethyl actate (100 ml) three times. Combined organics was dried with $MgSO_4$ and after removing solvent, the residue was purified by chromatography on silica gel (elutes: ethyl actate: hexane=4:6) to give 3.1 g of product as yellow oil. (66.0%)

4-(2-Fluoro-6-hydroxymethoxy-3-methoxy-benzoyl)-benzoic acid methyl ester 2.0 g of 5 (5.7 mmole) was dissolved in 50 ml of methylene chloride and to this solution, 15 g of activated $MnO_2$ was added in portions. The reaction was stirred at room temperature overnight. The solution was filtered through a celite pat and after removing the solvent, 1.7 g of product was obtained as yellow oil (86%).

4-(2-Fluoro-3-methoxy-6-methoxymethoxy-benzoyl)-benzoic acid 1.5 g of 6 (4.3 mmole) was dissolved in 15 ml of methanol and water was added dropwise until the solution became cloudy. 1.0 g of LiOH (2.4 mmole) was added slowly and the reaction was stirred at room temperature overnight. The reaction was quenched with 7.0 g of citric acid. After removing most of methanol, the aqueous solution was extracted with methylene chloride (30 ml) three times and combined organics was washed with brine twice, dried ($MgSO_4$). 1.4 g of product was obtained as while solid after removal of the solvent (98.0%).

7.2 Results and Discussion

The following features and characteristics are predictions of Compound 6 based on data of similarly situated drug-like and nondrug-like molecules, based on QikProp software (by William L. Jorgensen, available at http://www.schrodinger.com/ProductDescription.php? mID=6&sID=10). The following predictions suggest that Compound 6 would be a good candidate for a drug compound.
   (1) The molecular weight of Compound 6 is 536. Additional variants at about this molecular weight value or lower would be desirable. The number of properties that fall outside the range of 95% of similar values for known drugs is zero.

(2) The compound is predicted to have 2 metabolites, which would be favorable for plasma and gut stability.
(3) The oral bioavailability is predicted to be about 76%. Log MDCK and logCACO-2 cell permeability values are predicted to be within acceptable limits.
(4) The predicted logBB for crossing the blood brain barrier is −1.3. This value is on the lower end for drugs in general.
(5) The predicted log aqueous solubility is estimated between −3 to −5.
(6) The predicted logP is estimated at about 2.4.
(7) The predicted logIC50 for HERG K+ channel blockage is estimated at about −6.5 micromolar, which would fall within the average value for known drugs.
(8) As opposed to fluoro derivative compounds, Compound 6 polyphenols would be expected to be less drug-like.

8. EXAMPLE

Compounds 8H and 8J Significantly Inhibited PKG Activity In Vitro

Figure 10A:
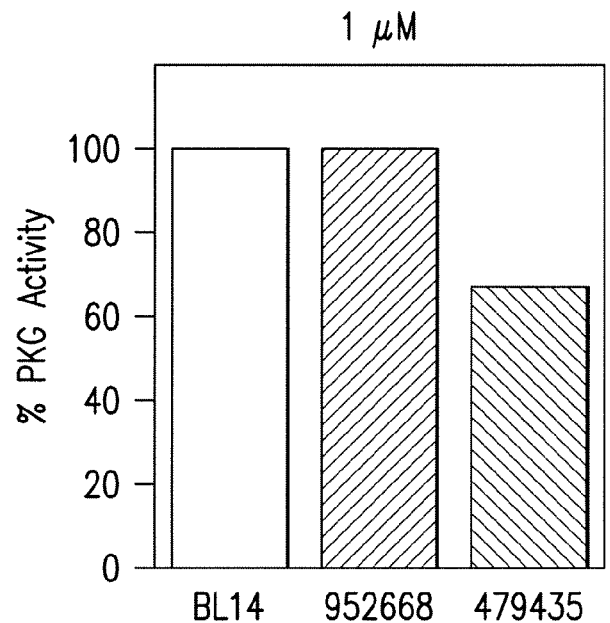
FIGS. 10A and 10B show inhibition of PKG activity by (A) 1 micromolar of either compound 8J (NOP952668) or compound 8H (NOP479435); or (B) 10 micromolar of either compound 8J (NOP952668) or compound 8H (NOP479435).
Figure 10B:
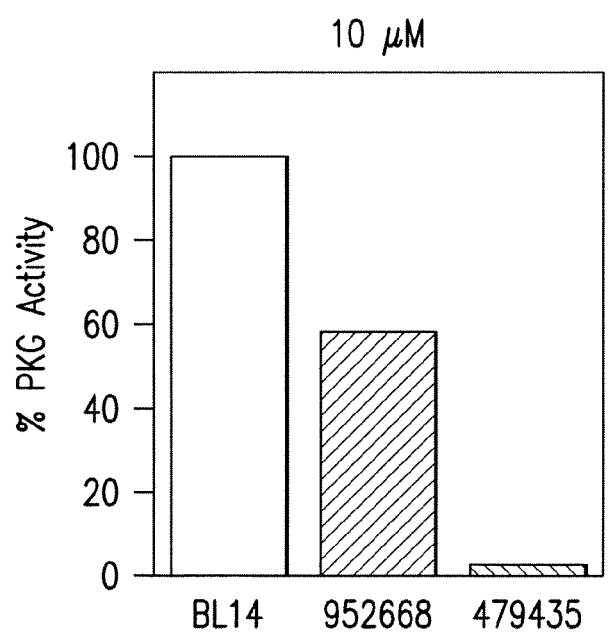

Compounds identified by in silico screening, including compounds of FIG. 8, were tested to determine whether they inhibit active recombinant PKG in an assay that measured the transfer of gamma-labeled $^{32}$P from radiolabeled ATP to a peptide substrate (RKISASEFDRPLR, SEQ ID NO: 10) in the absence or presence of compound. Compounds 8H (NOP479435) and 8J (NOP952668) were found to exhibit significant inhibitory activity at these concentrations (see FIGS. 10A-B), whereas other compounds tested did not show, under the assay conditions, significant inhibition at these concentrations. The results shown in FIGS. 10A-B were calculated from the average values of two independent experiments, and show the percentage PKG activity in the presence of the putative inhibitors relative to the activity in the absence of inhibitor. Of the compounds tested, 10 μM compound 8H (NOP479435) inhibited almost 100 percent of PKG activity. This activity is comparable to the inhibition of PKG by Rp-8-pCPT-cGMPS, which is the most widely used commercially available non-peptide inhibitor. Compound 8J (NOP952668) showed weaker inhibition.

Figure 7A:
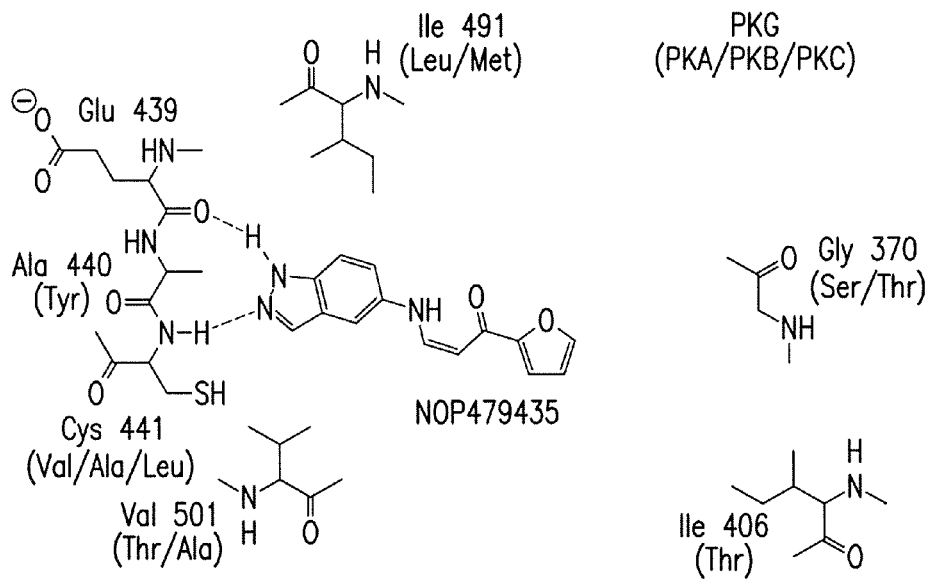
Figure 7B:
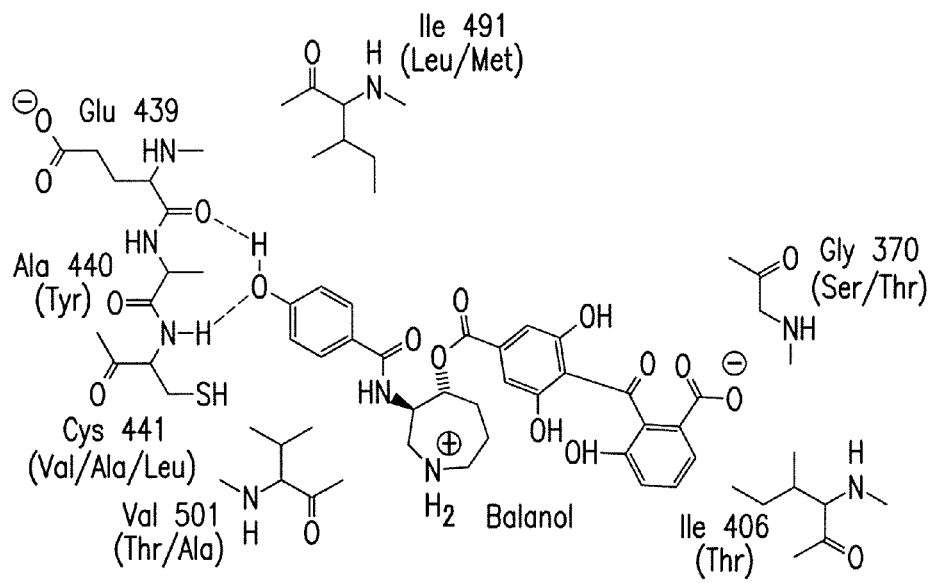
Figure 11:
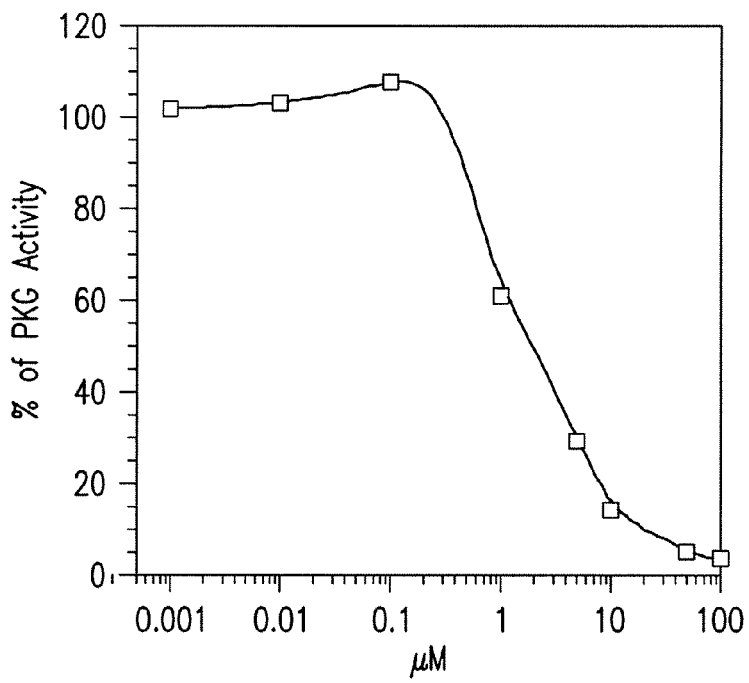
FIG. 11 shows the inhibition of PKG activity by increasing concentrations of compound 8H (NOP479-435).
Figure 12:
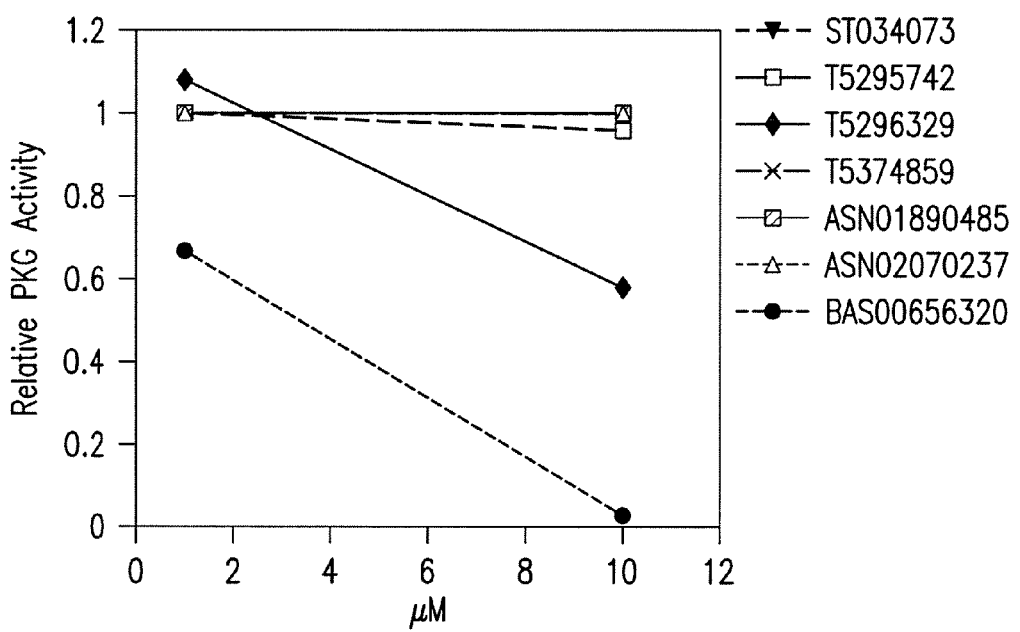
FIG. 12 shows the inhibition of PKG activity toward a peptide substrate in presence of 1 or 10 micromolar of each of the indicated compounds.

The ability of compound 8H (NOP479435) to decrease PKG 1α (activity was assessed by assaying PKG activity towards BPDEtide in the absence or presence of various concentrations of the compound. FIG. 11 shows the average values of duplicate experiments, plotted as the percentage of PKG activity in the absence of inhibitor. The IC$_{50}$ value calculated for compound 8H is 2 μM at 30 μM ATP. FIG. 7A shows compound 8H (NOP47935) docked to PKG; FIG. 7B shows balanol in the corresponding site, illustrating the sequence differences between PKGα and PKA/PKB/PKC.

9. EXAMPLE

Comparison of Selectivity of Compound Derivatives

Compounds including compound 6, were tested to determine whether they selectively inhibit PKG according to the methods described above.

Compounds 1 and 2, as known in the art (Lai et al. 1997), at high concentrations (5-10 times higher than comparative tests described below) demonstrate the ability to inhibit PKC and PKA. These compounds, along with compounds 6 and 7 (diagrammed below) were compared for their ability to inhibit PKG and PKA. See Table 1.

TABLE 1

| Compound | PKG activity (IC50) | PKA activity (IC50) |
|---|---|---|
| 1 | 7-8 nM | 30 nM (compound 24, Lai et al. 1997) |
| 2 | 7 nM | 4-33 nM (compound 22, Lai et al. 1997) |

TABLE 1-continued

| Compound | PKG activity (IC50) | PKA activity (IC50) |
|---|---|---|
| 6 | 40 nM | 950 nM |
| 7 | 40 nM | 38 nM |

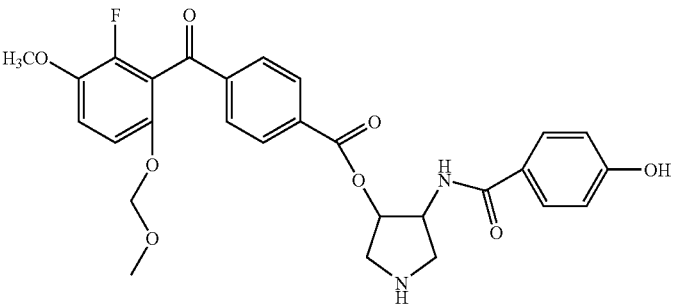

The data clearly show that Compound 6 was more selective than compound 7 and compounds 1 and 2 with respect to PKG. Compound 6 had an IC50 value that was about 20 times higher to inhibit PKA, whereas compound 7 had approximately the same IC50. Compounds 1 and 2 only exhibit a 3 fold difference.

Additional compounds (Series A and Series B compounds, including compounds 6 and 7 discussed above) were tested and their inhibitory activity measured. The structures of Series A and B compounds are summarized in FIGS. 20A and 20B. The inhibitory activity results of these compound is provided below in Table 2.

TABLE 2

SERIES A
Compounds (at 10 µM) screened for ability to inhibit PKG at 30 µM ATP

| Identity Number | Activity |
|---|---|
| 1 | ca. 37% inhibition |
| 2 | no inhibition |
| 3 | no inhibition |
| 4 | ca. 10% inhibition |
| 5 | no inhibition |
| 6 | ca. 30% inhibition |
| 7 | no inhibition |
| 8 | no inhibition |
| 9 | no inhibition |
| 10 | no inhibition |
| 11 | no inhibition |
| 12 | no inhibition |
| 13 | no inhibition |
| 14 | no inhibition |

TABLE 2-continued

SERIES B
Balanol Derivatives; Screened as decribed at 30 µM ATP

| # - Former Number | Activity |
|---|---|
| 1 - (NOP0317106) | IC50 = 7-8 nM (from literature: 30 nM PKA) |
| 2 - (NOP0403206) | IC50 = 7 nM (from literature: 4-33 for PKC isoforms; 70 for PKA) |
| 3 - (NOP-0403306) | 2 isomers - pM-µM |
| 4 - (NOP-0413406) | IC50 = 8 µM |
| 5 - (NOP-0413506) | IC50 = >10 µM |
| 6 - (NOP-0414606) | IC50 = 40 nM vrs PKG, 950 nM vrs PKA |
| 7 - (NOP-0414706) | IC50 = 40 nM vrs PKG, 38 nM vrs PKA |
| 8 - (NOP-4/14806) | IC50 = >10 µM |
| 9 - | no inhibition |
| 10 - | ≥5 µM |
| 11 - | no inhibition |
| 12 - | no inhibition |
| 13 - | no inhibition |
| 14 - | ≥10 µM |
| 15 - | |
| 16 - | |
| 17 - | |

The results of the screening tests demonstrate how changing substituents affect the inhibitory action of the compounds. The conclusions are summarized below.

(1) The substitution of the 6-membered ring (B) in balanol for a 5-membered ring (compound 2) reduces inhibition of PKG 5-fold, but that to other kinases by much more.

(2) Changing the 5-membered ring in compound 1 to a ring containing N, in compound 2, further reduces inhibition of PKA relative PKG.

(3) In Table 1, Compound 7 as compared to compound 2, where the F in the D ring is substituted for HOOC at 14" and the addition of H₃CO at 13" and removal of both OH groups from ring C reduces inhibition of PKG and reduces selectivity. However this change is not due to changes in ring D but likely due to removal of the OH moieties.

(4) In Table 1, Compound 6 demonstrates superior inhibition of PKG relative to PKA. This may be attributed to the N group in the ring (as compared with compound 4) and the presence of the —O—O— (as compared with compound 5).

These results showed dramatic modifications of linkage between rings C and D destroyed activity (as evidenced by series A). Altering ring A eliminated (e.g., derivative 13) or markedly reduced (e.g., derivative 14) inhibition. Modifying the linkage between rings A and B generally (derivatives 11 and 12), but not always (derivative 10) eliminated inhibition. Lastly, separate isomers of compound 3 were identified.

Derivative compound 6 selective inhibition showed promising results. Additional modifications would include:

a) adding OH groups at positions 4" and 6" in ring C to lower the IC50 toward PKG back to the 7-8 nM range;

b) altering substituents at the 10" position in ring D; and c) creating an amide linkage between rings B and C for stability.

10. EXAMPLE

Determining Linkages in PKG Inhibitor Compound 6

The design of alternative linkers to the established azepane, cyclopentane, and pyrrolidine rings for connecting the diarylketone of balanol analogues to the hinge-binding motif was studied in Compound 6 (Table 1). Compound 6 was analyzed for alternative linkers by looking at the structures and their relative rankings (1 to >157) at PKG and PKA with both phenol and indazole as the hinge-binding group (See FIGS. 14 and 15A-15L). In FIG. 14, lower numbers indicate better predicted binding at PKG and PKA, or more preference for PKG over PKA (PKG vs. PKA rank). However, neither the range of relative scores nor the receptor structure suggests large differences in selectivity can be obtained by varying the linker.

The data demonstrate that indazole as a hinge-binding motif continues to score better on average than phenol by a couple of kcal/mol (50-fold) for equivalent structures, although there's a range because the position of the linker with respect to charged residues E127 and D184 is sensitive to the size of the aromatic. Lower numbers in the final column indicate preference for indazole and higher numbers a preference for phenol.

It is apparent that the pyrrolidine linker of Compound 6 is already highly optimized for the receptor, and only a minority of the linkers tested score as well or better than this structure. Though the main role of a linker is to put the rest of the pharmacophore elements at the right distance and in the right orientation, optionally making a salt bridge, doing so in an ideal manner has been difficult.

The focus of this study was on amide, rather than ester, containing linkers, due to the known metabolism issue. The amide analogue of Compound 6 (and its indazole analogue) bind and scored similarly to the esters.

2-substituted piperazine derivatives (Z1-26) were also analyzed in this study. Specifically, Z24, Z14 and Z6 with phenol and Z14, Z15 and Z5 with indazole were found to be competitive with Compound 6, which would make them promising candidates.

Some derivatives of aminocyclopropane (C1-C4) scored fairly strongly and are comparable to Compound 6. Prolines did not appear to be worth pursuing at this stage. The indazolyl L-proline Compound 13 is in the set, P10, and its score is mediocre. The other proline isomers reviewed were generally poor at PKG (though one D-proline P12 with indazole received a high score at PKA, as did urea P24 with phenol). The best scoring proline at PKG was the indazolyl P16, a positional isomer/analogue of Compound 11.

Some of the 1,4-diazepane derivatives (D1-62, 7-membered ring with two nitrogens) scored very well with indazoles (D34, D59, D24, D12, D39, D7) or phenols (D59, D22, D46, D27, D6) but they appear harder to make than the piperazines.

Additionally, some aminopyridinium cations (A1-32) scored reasonably well, though the pK is of A1-4 and A7 are likely to be too low for the ring to be protonated. A8 with indazole and A12, A7 and A21 with phenol performed best. A variety of rings containing two nitrogens where both were functionalized as amides (X1-4, D21, D62, Z9, Z26) are predicted to be inactive.

The method used was ensemble docking with XP4.0 using four input conformations, to three PKA structures and three PKG homology models from pdb codes 1bx6, 1sve & 1rek. The final rankings were based on the best strain-corrected glidescore, treating indazoles and phenols, PKG and PKA separately.

11. EXAMPLE

Understanding SARs of Balanol Analogues

The present Example provides a description of the initial understanding the SARs of balanol analogues aimed at determining whether the azepine portion of balanol can be replaced by simpler and more readily accessible cyclic arrays such as pyrrolidine and cyclopentane without significant loss of PKG inhibitory activity. The results of these efforts are shown in Table 2.

Table 3 shows the PKG and PKA inhibition by balanol and its analogs with simple azepine replacement (IC$_{50}$ in μM).

TABLE 3

| Compd | balanol | B-1 | B-2 | B-10 | B-29 | B-31 |
|---|---|---|---|---|---|---|
| PKG | 0.0016 | 0.007 | 0.007 | >5 | >10 | >10 |
| PKA | 0.0039 | 0.03 | 0.07 | | | |

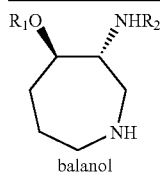

balanol

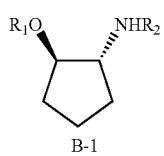

B-1

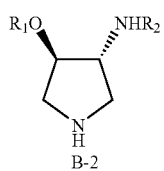

B-2

TABLE 3-continued

| Compd | balanol | B-1 | B-2 | B-10 | B-29 | B-31 |
|---|---|---|---|---|---|---|

$R_1 =$ 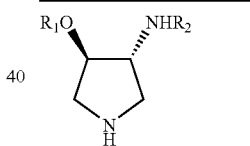

B-10

B-29

B-31

$R_2 =$ 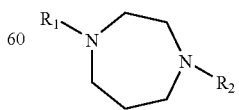

The conformational flexible seven-membered azepine ring appeared to be replaceable, as can be seen from Table 3 in which Compound B-2 with a five-membered pyrrolidine ring was found to be almost as potent as Balanol itself against PKG. In contrast to the azepine nitrogen atom in Balanol, which has been shown to be significant for its activities, the pyrrolidine nitrogen atom seemed dispensable, at least for PKG, since Compound B-1 with a cyclopentane ring that is otherwise identical to Compound B-2 was equally active. Consistent with the report that stereochemistry around azepine or its replacements is critical to bioactivities of Balanoids, all three analogues (Compounds B-10, B-29, B-31) with favorable ring sizes, but without a trans-vicinal amino alcohol substructure, lost activities. This substructure has been shown in computational modeling to guarantee a favorable spatial projection of the aromatic side chains R1 and R2.

In summary, the SARs studies of the perhydroazepine moiety of balanol indicate that the azepine ring can be replaced by five-membered rings as long as the replacement is able to raise the two aromatic side chains in a stereochemically correct manner. The two five-membered ring analogs 1 and 2 are attractive not only for their impressive potency but also for their ease of preparation. For example, by using epoxide-opening reactions (FIG. 17C), it took only three steps to reach the required pyrrolidine ring from commercially available materials. This compared very favorably to a seven-step synthesis of the corresponding azepine amino alcohol. As the five-membered ring system was much more easily accessible, they were generally used in preference to the azepane in later synthetic work.

Although recent work has provided direct evidence that balanol retained activities in cellular assays, it is expected that some attenuation of the polar nature of the benzophenone moiety will be highly desirable to obtain compounds with the overall physical properties suitable for continued pharmaceutical development. More importantly, Koide et al. demonstrated that removing certain benzophenone functionality could lead to a marked differentiation in protein kinase selectivity. Considering its tedious chemical synthesis, simplification of benzophenone portion is also of practical interest. Recently, Breitenlechner et al. reported potent balanol-like PKB inhibitors that bear a simplified benzophenone subunit with two hydroxyl groups removed from its internal benzene ring and the carboxylic acid functionality on the external benzene ring replaced by fluorine.

Table 4 shows PKG and PKA inhibition by balanol analogs with simplified benzophenone subunits ($IC_{50}$ in μM).

TABLE 4

| Comp | PKG | PKA |
|---|---|---|
| B-4 | 8 | |
| B-5 | >10 | |
| B-6 | 0.04 | 0.95 |
| B-7 | 0.04 | 0.04 |
| B-11 | >10 | |
| B-12 | >10 | |
| B-21 | 0.2 | >10 |
| B-24 | >10 | |
| B-25 | >10 | |
| B-28 | >10 | |
| B-32 | >10 | |
| B-33 | >10 | |
| B-40 | 0.8 | |
| B-43 | >10 | |
| B-44 | 0.0025 | 0.0031 |
| B-45 | 0.5 | 3.7 |

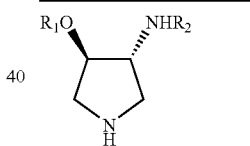

B-6, R' = $CH_3OCH_2$—
B-7, R' = H
B-21, R' = $CH_3(CH_2)_2$—
B-40, R' = $CH3O\,(CH_2)_2$—

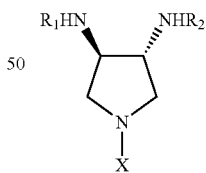

B-43, R' = $CH_3(CH_2)_2$—, X = Boc
B-44, R' = H, X = H
B-45, R' = $CH_3(CH_2)_2$—, X = H

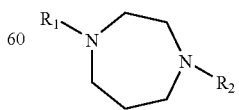

B-32, R' = $CH_3OCH_2$—
B-33, R' = H

TABLE 4-continued

| Comp | PKG | PKA |
|---|---|---|

R₁ = [structure: 4-(fluoro-methoxy-phenyl-carbonyl)benzoyl ester with OR' group]

[Cyclopentane structure with R₁O and NHR₂ substituents]

B-4, R' = CH₃OCH₃—
B-5, R' = H

[Pyrrolidine structure with R₁HN and N-R₂]

B-11, R' = CH₃OCH₂—
B-12, R' = H

[Piperazine structure R₁—N N—R₂]

B-25, R' = CH₃OCH₂—
B-28, R' = H

R₂ = [4-hydroxybenzoyl structure]

[Structure of B-24: fluoro-methoxy-benzisoxazole linked to benzoate ester of pyrrolidine with NHR₂]

B-24

Compared with balanol, this fluorinated benzophenone system is less polar and more synthetically straightforward, and therefore, is a good starting point for modification. Further encouraged by computational studies that it scores as well as balanol itself against PKG, a series of balanol analogues were made based on this benzophenone motif. As can be seen in the activity of Compound B-7, new benzophenone only led to a slight reduction of potency. Intriguingly, Compound B-6, the precursor of Compound B-7 with the MOM-protected hydroxyl group, retained PKG inhibitory activity but lost a substantial portion of its potency on PKA, and then, provided the first selective PKG inhibitor in this investigation.

According to the X-ray crystallography studies from Breitenlechner et al, the free hydroxyl group of the benzophenone formed a COO . . . HO hydrogen bond with the side chain of Glu91 in PKA. In addition, a variety of residues make van der Waals contacts with the benzophenone moiety. It is reasoned that the MOM side chain in Compound B-7 increases van der Waals contact that is enough to offset the loss of a hydrogen bond in its binding to PKG but not enough for PKA. Computational modeling on this particular site indicates that hydrophobic side chains will be favorable for selectivity. Therefore, the present invention sought to replace the MOM side chain with propane, which, as in Compound B-21, resulted in a dramatic increase of specificity for PKG over PKA coupled with an acceptable reduction of potency. As shown by Compound B-40, increasing the size of side chains will further decrease compounds' potency. These results reinforced the notion that despite the high homology in the catalytic domains of AGC-family kinases, there is enough difference to allow for the development of potent and selective inhibitors acting in this region One compound with a planar benzophenone, Compound B-24, was prepared to see if a more rigid conformation could lead to active compounds. This modification was found to be essentially devoid of activity.

Interestingly, with the new benzophenone ring, the pyrrolidine nitrogen now becomes critical, as in Compound B-5 and Compound B-43, deleting N atom or masking with a protecting group resulted in a totally lost of activity. The published structure of a balanol-PKA complex revealed that the benzophenone fragment of balanol could correspond to the triphosphate region of ATP and interacted extensively with the kinase glycine-rich loop, also called the triphosphate subsite. In the complex, the azepane ring occupied the catalytic loop or the ribose subsite in which the azepane N formed hydrogen bonds with the carbonyl oxygen atom of residue Glu170. It is speculated that the polar and nonpolar interactions generated by the new benzophenone moiety couldn't make up for the loss of hydrogen bonds involving the pyrrolidine nitrogen atom. Since the previous SAR results are not completely applicable to the new benzophenone system, the modification of the azepine part was further investigated. All analogues with benzophenone attached to rings other than pyrrilidine showed poor activities and may well be another example of significance of positioning benzophenone properly regardless its modification.

The presence of an ester functionality has prompted concern over the metabolic stability of the compound. There is evidence suggesting that replacing labile esters with amide linkage could increase compounds' plasma stability. Unfortunately, this replacement often resulted in substantial loss of potency in the case of PKC studies. To investigate its effect on PKG inhibitory activity, diamide compounds, Compounds B-44 and B-45 were prepared. Two compounds are even slightly more potent than their ester counterparts. It should be noted in considering these data that diamide compounds were made in optically pure form, with the same (1R,2R) configuration as is found in naturally occurring balanol. The natural balanol has been shown to be more potent than its unnatural enantiomer. Nevertheless, we were able to achieve plasma stability without losing potent inhibition.

A key site on the benzophenone part was identified through which hydrophobic chains regulating compounds' affinity for PKG over other kinases can be introduced. However, substantial loss of activity was observed in most cases as a compensation for achieving sufficient selectivity. Since there was a need to improve potency through other part of balanol molecules, attention was given to the modification of the 4-hydroxybenzamido moiety.

Table 5 shows PKG and PKA inhibition by balanol analogs with the replacements of hydroxybenamido moiety (IC50 in μM).

TABLE 5

| Comp | PKG | PKA |
|---|---|---|
| B-13 | >10 | |
| B-14 | >10 | |
| B-22 | >10 | |
| B-23 | >10 | |
| B-26 | >10 | |
| B-30 | 0.085 | |
| B-35 | >10 | |
| B-46 | 0.007 | 5 |
| B-53 | 0.025 | 1.2 |
| B-54 | >10 | |

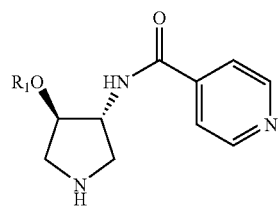

B-22, R' = CH$_3$(CH$_2$)$_2$—
B-23, R' = CH$_3$O CH$_2$—
B-26, R' = H

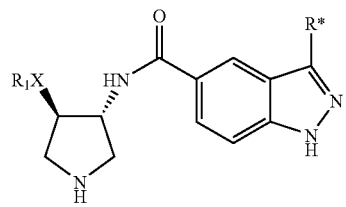

B-30, X = O, R' = CH$_3$OCH$_2$—, R'' = H
B-35, X = NH, R' = CH$_3$OCH$_2$—, R'' = 4-F—Ph
B-46, X = NH, R' = CH$_3$(CH$_2$)$_2$—, R'' = H
B-53, X = NH, R' = CH$_3$(CH$_2$)$_2$—, R'' = Me

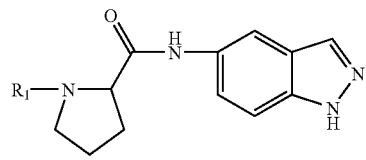

B-13, R' = CH$_3$OCH$_2$—
B-14, R' = OH

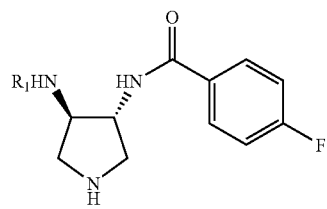

B-54, R' = CH$_3$(CH$_2$)$_2$—

TABLE 5-continued

| Comp | PKG | PKA |
|---|---|---|

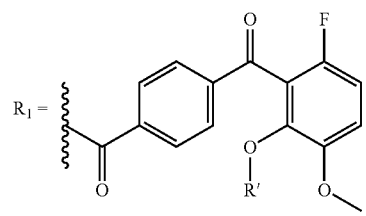

As indicated by available crystal structures of ATP-PKA and balanol-PKA complexes, a planar moiety occupies the adenine subsite and PKA residues whose atoms participate in hydrogen bonds to balanol are the same as those that interact with ATP. Specifically, the carbonyl oxygen atom of Glu121 and the backbone nitrogen atom of Val123 form hydrogen bonds in both balanol-PKA and ATP-PKA complexes. In balanol-PKA complex, the single hydroxyl group of balanol's 4-hydroxybenzamido moiety serves as both H-bond donor and acceptor, donating and accepting electrons to form hydrogen bonds with Glu121 and Val 123, respectively; in the ATP-PKA complex, the purine ring N1 atom donates electrons to the Val123 amide hydrogen atom while the purine ring N6 atom accepts electrons from the Glu121 backbone carboyl oxygen atom. The H-bond to Val123 or homologue is thought to be nearly universal among protein kinase inhibitor complexes and is apparently critical for tight binding inhibitors. Replacing 4-hydroxybenzamido moiety with pyridine has been shown to be successful for potent PKB inhibitors and as revealed by following X-ray studies, pyridine could form a N . . . OCNH hydrogen bond to Val 123 through its N atom. As shown by Compounds B-22, B-23, and B-26, this replacement was totally unsuccessful for PKG.

Comparing with 4-hydroxybenzamido moiety of balanol or adenine moiety of ATP, pyridine lacks a H-bond donor, which may diminish its affinity to PKG. Aromatic heterocycles as adenine mimics, containing both H-bond donor and acceptor, frequently appear in kinase inhibitors and may be a good replacement for 4-hydroxybenzamido moiety. Suggested by computational modeling, 4-hydroxybenzamido moiety was replaced with indazole. As can be seen in the activity of Compound B-30, this modification did not lead to an improvement although retained comparable potency against PKG. Surprisingly, indazole replacement, as in Compound B-45, dramatically improved activities of diamide compounds. Stable diamide compounds are more desirable in terms of stability in vivo. Contradicting to computational prediction, adding hydrophobic groups on 3 position of indazole increased neither activity nor selectivity, as shown by balanol-50 and 55 in Table 4.

F is often used as a substitute for hydroxyl group in medicinal chemistry, however, replacing hydroxyl group with F, as in Compound B-54, resulted in loss of activity. In the screening of unrelated compounds including byproducts and intermediates generated during the synthesis, it was found that symmetrical diamide Compound B-48 showed moderate PKG inhibitory activity. This is surprising in light of previous SARs indicating that the benzophenone scaffold is crucial to bioactivities. Further modification yielded the most potent Compound B-50 in this series with an IC50 of 70 nm. This simple molecule showed no selectivity over PKA. Since high molecular weight is a concern, these simple motifs may provide a new ground for further medicinal chemistry efforts.

Table 6 shows PKG and PKA inhibition by balanol analogs with new scaffolds ($IC_{50}$ in µM).

TABLE 6

| Comp | B-48 | B-49 | B-50 | B-51 | B-52 |
|---|---|---|---|---|---|
| PKG | ~0.2 | ~1 | 0.07 | >10 | >10 |
| PKA |  |  | 0.07 |  |  |

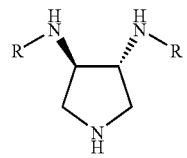

B-48, R = $R_1$
B-49, R = $R_2$(X = H)

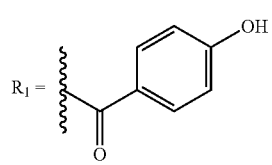 [SMILES: *C(=O)c1ccc(O)cc1]

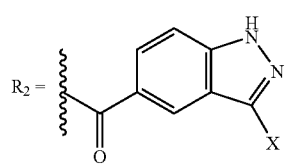

B-51, R = $R_2$(X = 4-F—Ph)
B-52, R = $R_2$(X = Me)

TABLE 6-continued

| Comp | B-48 | B-49 | B-50 | B-51 | B-52 |
|---|---|---|---|---|---|

B-50

J. M. Defauw et al. reported a class of acyclic balanol analogs that are highly potent and selective for PKC. As shown in FIG. 18, a series of compounds with a flexible ethylenediamine bridge was prepared in hope of generating new scaffolds for PKG. These compounds are generally inactive with an exception of Compounds B-41 and B-42, which showed moderate potency (data not shown).

12. EXAMPLE

Testing Compounds 6 and 46

Compounds 6 and 46 exhibited superior inhibitory activity toward PKG and selectivity toward PKA. The structures for compounds 6 and 46 are provided in FIG. 21. The IC50 of compound 6 with PKG and PKA is 40 nM and 950 nM, respectively; and the IC50 of compound 46 with PKG and PKA is 7.5 nM and 2 µM, respectively.

Both compounds were further tested for their efficacy in reducing complete Freund's adjuvant (CFA)-induced thermal hyperalgesia in the hindpaws of rats. The hindpaws of rats were first tested for their response to a thermal probe as a baseline reference. Then the right hindpaw was injected with CFA (100 µl). The injected site developed edema and redness, indicating an inflammatory reaction, within 12 hours. 24 hours later, the latency of both hindpaws withdraw to a thermal stimulus was determined, the injected paw of all of the rats showed a significantly more rapid withdrawal time in response to the thermal stimulus relative to the contralateral uninjected side. The rats were then given either compound 6 or 46 at different times after CFA injection via different routes as shown in the tables below. Each hindpaw was then tested for its response to a thermal stimulus on successive days. Tables 7 and 8 provide a summary of the data.

TABLE 7

| Compound 6 Conc. | Number of animals[a] | Compound administration after CFA injection | Route | Effectiveness* |
|---|---|---|---|---|
| 25 µM** | 1 | 24 hours | Intrathecal pump | >90% 6 days later |
| 0.25 µM** | 1 | 72 hours | Intrathecal pump | >50% recovery 10 days |
| 82.5 µM** | 2 | 24 hours | Intrathecal single injection | No effect |
| 3.3 nmol | 2 | 60 hours | Subcutaneous pump | >90% recovery 5 days later |

TABLE 8

| Compound 46 Conc. | Number of animals[a] | Compound administration after CFA injection | Route | Effectiveness* |
|---|---|---|---|---|
| 0.25 mM** | 2 | 24 hours | Intrathecal single injection | No effect |

TABLE 8-continued

| Compound 46 Conc. | Number of animals[a] | Compound administration after CFA injection | Route | Effectiveness* |
|---|---|---|---|---|
| 0.5 nmol | 2 | 24 hours | Intra-peritoneal single injection | No effect |
| 4 nmol | 2 | 24 hours | Subcutaneous pump | No effect |

[a]Equal number of control animals
*Effectiveness compares the differential latency (CFA injected paw- contralateral paw) between the control animals that received CFA injection and comparable vehicle that the compound was dissolved in.
**Final concentration is calculated based on the assumption that there is 400 µl of cerebral spinal fluid in the rat. (Neurotherapeutics: Emerging Strategies By Linda M. Pullan, Jitendra Patel).

The single dose injection of compound 6 failed to reduce thermal hyperalgesia; this may be due a potential instability in the structure. These preliminary results suggest that compound 6 exhibits analgesic effects comparable to that achieved with the most potent commercially available inhibitor of PKG (RP-G: Rp-8-pCPT-cGMPS). Animals exposed to compound 6 did not exhibit any adverse behavioral effects with regard to eating, sleeping, defecating, micturation, balance, exploring, or socializtion. Modification of compound 6 to increase affinity and selectivity, and perhaps plasma half-life, as described above, will be important. In contrast, compound 46, at the doses tested, did not exhibit any analgesic effects and failed to alleviate CFA induced thermal hyperalgesia within the testing dosages and with different modes of delivery (intrathecally or subcutaneously, e.g., via single dose injection and by osmotic pump for a continues delivery). Two rats that received intrathecal compound 46 exhibited signs of motor dysfunction after injection. For example, the animals had difficulty in changing from the supine to prone positions. They also exhibited ataxia. The effects lasted for at least 24 hours and disappeared after 3 days.

13. REFERENCES

Abdulla F A, Smith P A (2001) Axotomy- and autotomy-induced changes in the excitability of rat dorsal root ganglion neurons. J Neurophysiol 85:630-643.

Alberini C M, Ghirardi M, Metz R, Kandel E R (1994) C/EBP is an immediate-early gene required for the consolidation of long-term facilitation in *Aplysia*. Cell 76:1099-1114.

Ambron R T, Walters E T (1996) Priming events and retrograde injury signals. A new perspective on the cellular and molecular biology of nerve regeneration. Mol Neurobiol 13:61-79.

Ambron R T, Schmied R, Huang C C, Smedman M (1992) A signal sequence mediates the retrograde transport of proteins from the axon periphery to the cell body and then into the nucleus. J Neurosci 12:2813-2818.

Ambron R T, Dulin M F, Zhang X P, Schmied R, Walters E T (1995) Axoplasm enriched in a protein mobilized by nerve injury induces memorylike alterations in *Aplysia* neurons. J Neurosci 15:3440-3446.

Ambron R T, Zhang X P, Gunstream J D, Povelones M, Walters E T (1996) Intrinsic injury signals enhance growth, survival, and excitability of *Aplysia* neurons. J Neurosci 16:7469-7477.

Antonov I, Antonova I, Kandel E R, Hawkins R D (2003) Activity-dependent presynaptic facilitation and hebbian LTP are both required and interact during classical conditioning in *Aplysia*. Neuron 37:135-147.

Bartsch D, Ghirardi M, Skehel P A, Karl K A, Herder S P, Chen M, Bailey C H, Kandel E R (1995) *Aplysia* CREB2 represses long-term facilitation: relief of repression converts transient facilitation into long-term functional and structural change. Cell 83:979-992.

Bedi S S, Salim A, Chen S, Glanzman D L (1998) Long-term effects of axotomy on excitability and growth of isolated *Aplysia* sensory neurons in cell culture: potential role of cAMP. J Neurophysiol 79:1371-1383.

Billy A J, Walters E T (1989) Long-term expansion and sensitization of mechanosensory receptive fields in *Aplysia* support an activity-dependent model of whole-cell sensory plasticity. J Neurosci 9:1254-1262.

Bredt D S, Snyder S H (1990) Isolation of nitric oxide synthetase, a calmodulin-requiring enzyme. Proc Natl Acad Sci USA 87:682-685.

Breitenlechner C B, Wegge, T, Berillon, L, Graul, K, Marzenell, K, Friebe, W, Thomas, U, Schumacher, R, Huber, R, Engh, R A, Masjost, B (2004) Structure-based optimization of novel azepane derivatives as PKB inhibitors 47:1375-1390.

Brunet J F, Shapiro E, Foster S A, Kandel E R, Iino Y (1991) Identification of a peptide specific for *Aplysia* sensory neurons by PCR-based differential screening. Science 252: 856-859.

Bryan J (2004) Transdermal drug delivery may be a common technique in the future. Pharmaceutical J. 273:292-293.

Byrne J H, Kandel E R (1996) Presynaptic facilitation revisited: state and time dependence. J Neurosci 16:425-435.

Carhart, R. E.; Smith, D. H.; Venkataraghavan, R (1985). Atom Pairs as Molecular Features in Structure-Activity Studies: Definitions and Applications. J. Chem. Inf. Comput. Sci. 25: 64-73.

Cha H, Shapiro P (2001) Tyrosine-phosphorylated extracellular signal regulated kinase associates with the Golgi complex during G2/M phase of the cell cycle: evidence for regulation of Golgi structure. J Cell Biol 153:1355-1367.

Chain D G, Casadio A, Schacher S, Hegde A N, Valbrun M, Yamamoto N, Goldberg A L, Bartsch D, Kandel E R, Schwartz J H (1999) Mechanisms for generating the autonomous cAMP-dependent protein kinase required for long-term facilitation in *Aplysia*. Neuron 22:147-156.

Chen Y, Devor M (1998) Ectopic mechanosensitivity in injured sensory axons arises from the site of spontaneous electrogenesis. Eur J Pain 2:165-178.

Clatworthy A L, Grose E (1999) Immune-mediated alterations in nociceptive sensory function in *Aplysia californica*. J Exp Biol 202:623-630.

Clatworthy A L, Illich P A, Castro G A, Walters E T (1995) Role of peri-axonal inflammation in the development of thermal hyperalgesia and guarding behavior in a rat model of neuropathic pain. Neurosci Lett 184:5-8.

Crown E D, Ye Z, Johnson K M, XU G Y, AcAdoo D J, Westlund K N, Hulsebosch C E (2005) Upregulation of the phosphorylated form of CREB in spinothalamic tract cells following spinal cord injury: relation to central neuropathic pain. Neurosci Lett 384:139-144.

Dagan D, Levitan I B (1981) Isolated identified *Aplysia* neurons in cell culture. J Neurosci 1:736-740.

Dale N, Schacher S, Kandel E R (1988) Long-term facilitation in *Aplysia* involves increase in transmitter release. Science 239:282-285.

Dash P K, Tian L M, Moore A N (1998) Sequestration of cAMP response element-binding proteins by transcription factor decoys causes collateral elaboration of regenerating *Aplysia* motor neuron axons. Proc Natl Acad Sci USA 95:8339-8344.

DesGroseillers L, Auclair D, Wickham L, Maalouf M (1994) A novel actin cDNA is expressed in the neurons of *Aplysia californica*. Biochim Biophys Acta 1217:322-324.

Farr M, Mathews J, Zhu D F, Ambron R T (1999) Inflammation causes a long-term hyperexcitability in the nociceptive sensory neurons of *Aplysia*. Learn Mem 6:331-340.

Farr M, Zhu D F, Povelones M, Valcich D, Ambron R T (2001) Direct interactions between immunocytes and neurons after axotomy in *Aplysia*. J Neurobiol 46:89-96.

Fiallos-Estrada C E, Kummer W, Mayer B, Bravo R, Zimmermann M, Herdegen T (1993) Long-lasting increase of nitric oxide synthetase immunoreactivity, NADPH-diaphorase reaction and c-JUN co-expression in rat dorsal root ganglion neurons following sciatic nerve transection. Neurosci Lett 150:169-173.

Francis S H, Corbin J D (1994) Structure and function of cyclic nucleotidedependent protein kinases. Annu Rev Physiol 56:237-272.

Friesner, R. A.; Banks, J. L.; Murphy, R. B.; Halgren, T. A.; Klicic, J. J.; Mainz, D. T.; Repasky, M. P.; Knoll, E. H.; Shelley, M.; Perry, J. K.; Shaw, D. E.; Francis, P.; Shenkin, P. S (2004). Glide: A New Approach for Rapid, Accurate Docking and Scoring. 1. Method and Assessment of Docking Accuracy. J. Med. Chem. 47: 1739-1749.

Ghirardi M, Braha O, Hochner B, Montarolo P G, Kandel E R, Dale N (1992) Roles of PKA and PKC in facilitation of evoked and spontaneous transmitter release at depressed and nondepressed synapses in *Aplysia* sensory neurons. Neuron 9:479-489.

Glanzman D L, Kandel E R, Schacher S (1989) Identified target motor neuron regulates neurite outgrowth and synapse formation of *Aplysia* sensory neurons in vitro. Neuron 3:441-450.

Glass D B, Krebs E G (1982) Phosphorylation by guanosine 3':5'-monophosphate-dependent protein kinase of synthetic peptide analogs of a site phosphorylated in histone H2B. J Biol Chem 257:1196-1200.

Goldsmith B A, Abrams T W (1992) cAMP modulates multiple $K^+$ currents, increasing spike duration and excitability in *Aplysia* sensory neurons. Proc Natl Acad Sci USA 89:11481-11485.

Gracety R H, Lynch S A, Bennett G J (1992) Painful neuropathy: altered central processing maintained dynamically by peripheral input. Pain 51:175-194.

Griffiths C, Wykes V, Bellamy T C, Garthwaite J. (2003) A new and simple method for delivering clamped nitric oxide concentrations in the physiological range: application to activation of guanylyl cyclase-coupled nitric oxide receptors. Mol. Pharmacol. 64(6):1349-56.

Gudi T, Lohmann S M, Pilz R B (1997) Regulation of gene expression by cyclic GMP-dependent protein kinase requires nuclear translocation of the kinase: identification of a nuclear localization signal. Mol Cell Biol 17:5244-5254.

Gunstream J D, Castro G A, Walters E T (1995) Retrograde transport of plasticity signals in *Aplysia* sensory neurons following axonal injury. J Neurosci 15:439-448.

Halgren, T. A.; Murphy, R. B.; Friesner, R. A.; Beard, H. S.; Frye, L. L.; Pollard, W. T.; Banks, J. L (2004). Glide: A New Approach for Rapid, Accurate Docking and Scoring. 2. Enrichment Factors in Database Screening. J. Med. Chem. 47:1750-1759.

Hall K U, Collins S P, Gamm D M, Massa E, DePaoli-Roach A A, Uhler M D (1999) Phosphorylation-dependent inhibition of protein phosphatase-1 by G-substrate. A Purkinje cell substrate of the cyclic GMP-dependent protein kinase. J Biol Chem 274:3485-3495.

Hanz S, Perlson E, Willis D, Zheng J Q, Massarwa R, Huerta J J, Koltzenburg M, Kohler M, van-Minnen J, Twiss J L, Fainzilber M (2003) Axoplasmic importins enable retrograde injury signaling in lesioned nerve. Neuron 40:1095-1104.

Internation Patent Application No. PCT/US92/07124, Publication No. WO93/03730.

Jacobson, M. P.; Pincus, D. L.; Rapp, C. S.; Day, T. J. F.; Honig, B.; Shaw, D. E.; Friesner, R. A (2004). A Hierarchical Approach to All-Atom Protein Loop Prediction. Proteins 55: 351-357.

Ji R R, Woolf C J (2001) Neuronal plasticity and signal transduction in nociceptive neurons: implications for the initiation and maintenance of pathological pain. Neurobiol Dis 8: 1-10.

Johanson S O, Crouch M F, Hendry I A (1995) Retrograde axonal transport of signal transduction proteins in rat sciatic nerve. Brain Res 690:55-63.

Karin M (1994) Signal transduction from the cell surface to the nucleus through the phosphorylation of transcription factors. Curr Opin Cell Biol 6:415-424.

Kim Y I, Na H S, Kim S H, Han H C, Yoon Y W, Sung B, Nam H J, Shin S L, Hong S K (1998) Cell type-specific changes of the membrane properties of peripherally-axotomized dorsal root ganglion neurons in a rat model of neuropathic pain. Neuroscience 86:301-309.

Koide K, Bunnage M, Paloma L, Kanter J, Taylor S, Brunton L, and Nicolaou K (1995) Molecular design and biological activity of potent and selective protein kinase inhibitors related to balanol. Chem and Bio 2(9):601-608.

Lai Y S, Mendoza J S, Jagdmann G E, Menaldino D S, Biggers C K, Heerding J M, Wilson J W, Hall S E, Jiang J B, Janzen W P, Ballas L M (1997) Synthesis and protein kinase C inhibitory activities of balanol analogs with replacement of the perhydroazepine moiety. J. Med. Chem. 40:226-235.

LaMotte R H, Shain C N, Simone D A, Tsai E F P (1991) Neurogenic hyperalgesia: psychophysical studies of underlying mechanisms. J Neurophysiol 66:190-211.

Lee J H, Orice R H, Williams F G, Mayer B, Beitz A J (1993) Nitric oxide synthase is found in some spinothalamic neurons and in neuronal processes that appose spinal neurons that express Fos induced by noxious stimulation. Brain Res 608:324-333.

Lewin M R, Walters E T (1999) Cyclic GMP pathway is critical for inducing long-term sensitization of nociceptive sensory neurons. Nat Neurosci 2:18-23. Liao X, Gunstream J D, Lewin M R, Ambron R T, Walters E T (1999) Activation of protein kinase A contributes to the expression but not the induction of long-term hyperexcitability caused by axotomy of *Aplysia* sensory neurons. J Neurosci 19:1247-1256.

Lin H, Bao J, Sung Y J, Walters E T, Ambron R T (2003) Rapid electrical and delayed molecular signals regulate the serum response element after nerve injury: convergence of injury and learning signals. J Neurobiol 57:204-220.

Mai et al. (2002) Efficiency of protein transduction is cell type-dependent and is enhanced by dextran sulfate. J Biol Chem 277:30208-30218.

Marais R, Wynne J, Treisman R (1993) The SRF accessory protein Elk-1 contains a growth factor-regulated transcriptional activation domain. Cell 73:381-393.

Martin K C, Michael D, Rose J C, Barad M, Casadio A, Zhu H, Kandel E R (1997) MAP kinase translocates into the nucleus of the presynaptic cell and is required for long-term facilitation in *Aplysia*. Neuron 18:899-912.

Michael D, Martin K C, Seger R, Ning M M, Baston R, Kandel E R (1998) Repeated pulses of serotonin required for long-term facilitation activate mitogen-activated protein kinase in sensory neurons of *Aplysia*. Proc Natl Acad Sci USA 95:1864-1869.

Mo E, Amin H, Bianco I H, Garthwaite J. (2004) Kinetics of a cellular nitric oxide/cGMP/phosphodiesterase-5 pathway. J Biol. Chem. 279(25):26149-58.

Millan M J (1999) The induction of pain: an integrative review. Prog Neurobiol 57:1-164.

Monfort P, Munoz M D, Kosenko E, Felipo V (2002) Long-term potentiation in hippocampus involves sequential activation of soluble guanylate cyclase, cGMP-dependent protein kinase, and cGMP-degrading phosphodiesterase. J Neurosci 22:10116-10122.

Moroz L L, Chen D, Gillette M U, Gillette R (1996) Nitric oxide synthase activity in the molluscan CNS. J Neurochem 66:873-876.

Muller U, Carew T J (1998) Serotonin induces temporally and mechanistically distinct phases of persistent PKA activity in *Aplysia* sensory neurons. Neuron 21:1423-1434.

Palecek J, Paleckova V, Willis W D (2003) Fos expression in spinothalamic and postsynaptic dorsal column neurons following noxious visceral and cutaneous stimuli. Pain 104:249-257.

Park S Y, Choi J Y, Kim R U, Lee Y S, Cho H J, Kim D S (2003) Downregulation of voltage-gated potassium channel a gene expression by axotomy and neurotrophins in rat dorsal root ganglia. Mol Cells 16:256-259.

Sarjeant J M, Lawrie A, Kinnear C, Yablonsky S, Leung W, Massaeli H, Prichett W, Veinrot J P, Rossart E, Rabinovitch M (2003) Apolipoprotein D inhibits platelet derived growth factor BB-induced vascular proliferated [sic] by preventing translocation of phosphorylated signal regulated kinase ½ to the nucleus. Arterioscler. Throm. Vasc. Biol. 23:2172-2177.

Pohler D, Butt E, Meissner J, Muller S, Lohse M, Walter U, Lolimann S M, Jarchau T (1995) Expression, purification, and characterization of the cGMP-dependent protein kinases I_and II using the baculovirus system. FEBS Lett 374:419-425.

Schlossmann J, Feil R, Hofmann F (2003) Signaling through NO and cGMP-dependent protein kinases. Ann Med 35:21-27.

Schmied R, Ambron R T (1997) A nuclear localization signal targets proteins to the retrograde transport system, thereby evading uptake into organelles in *Aplysia* axons. J Neurobiol 33: 151-160.

Schmied R, Huang C C, Zhang X P, Ambron D A, Ambron R T (1993) Endogenous axoplasmic proteins and proteins containing nuclear localization signal sequences use the retrograde axonal transport/nuclear import pathway in *Aplysia* neurons. J Neurosci 13:4064-4071.

Scholz K P, Byrne J H (1988) Intracellular injection of cAMP induces a longterm reduction of neuronal $K^+$ currents. Science 240:1664-1666.

Scott J D (1991) Cyclic nucleotide-dependent protein kinases. Pharmacol Ther 50:123-145.

Setyawan J, Koide K, Diller T C, Bunnage M E, Taylor S S, Nicolaou K C, Brunton L L (1999) Inhibition of protein kinases by balanol: specificity within the serine/threonine protein kinase subfamily. Mol. Pharmacol. 56(2):370-6.

Smith A R, Visioli F, Hagen T M (2002) Vitamin C matters: increased oxidative stress in cultured human aortic endothelial cells without supplemental ascorbic acid. FASEB J 10.1096/fj.01-0825fje.

Smolenski A, Bachmann C, Reinhard K, Honig-Liedl P, Jarchau T, Hoschuetzky H, Walter U (1998) Analysis and regulation of vasodilator stimulated phosphoprotein serine 239 phosphorylation in vitro and in intact cells using a phosphospecific monoclonal antibody. J Biol Chem 273: 20029-20035.

Study R E, Kral M G (1996) Spontaneous action potential activity in isolated dorsal root ganglion neurons from rats with a painful neuropathy. Pain 65:235-242.

Sung Y J, Ambron R T (2004) Pathways that elicit long-term changes in gene expression in nociceptive neurons following nerve injury: contributions to neuropathic pain. Neurol Res 26:195-203. Sung Y J, Hwang M C, Hwang Y W (1996) The dominant negative effects of H-Ras harboring a Gly to Ala mutation at position 60. J Biol Chem 271: 30537-30543.

Sung Y J, Conti J, Currie J R, Brown W T, Denman R B (2000) RNAs that interact with the fragile X syndrome RNA binding protein FMRP. Biochem Biophys Res Commun 275: 973-980.

Sung Y J, Povelones M, Ambron R T (2001) RISK-1: a novel MAPK homologue in axoplasm that is activated and retrogradely transported after nerve injury. J Neurobiol 47:67-79.

Sung Y J, Dolzhanskaya N, Nolin S L, Brown T, Currie J R, Denman R B (2003) The fragile X mental retardation protein FMRP binds elongation factor 1A mRNA and negatively regulates its translation in vivo. J Biol Chem 278: 15669-15678.

Sung Y J and Ambron, R T (Mar. 22, 2004) Pathways that elicit long-term changes in gene expression in nociceptive neurons following nerve injury: contributions to neuropathic pain. Neurological Research 26:195-203.

Sung, Y J, Walters, E T and Ambron, R T (Aug. 25, 2004) A neuronal isoform of protein kinase G couples mitogen-activated protein kinase nuclear import to axotomy-induced long-term hyperexcitability in *Aplysia* sensory neurons. J. Neurosci. 24(34):7583-7595.

Sutton M A, Carew T J (2000) Parallel molecular pathways mediate expression of distinct forms of intermediate-term facilitation at tail sensory motor synapses in *Aplysia*. Neuron 26:219-231.

Ungless M A, Gasull X, Walters E T (2002) Long-term alteration of S-type potassium current and passive membrane properties in *Aplysia* sensory neurons following axotomy. J Neurophysiol 87:2408-2420.

U.S. Pat. No. 4,708,716 by Sibalis, D. Transdermal drug applicator. Filed Sep. 16, 1985 and issued Nov. 24, 1987.

U.S. Pat. No. 5,405,614, by D'Angelo; J P and Schur, H. Electronic transdermal drug delivery system. Filed Jan. 11, 1993 and issued Apr. 11, 1995.

U.S. Pat. No. 6,476,007 by Tao, Y and Johns, R A. Isoform-specific inhibition for treatment of pain and reduction of anesthetic threshold. Filed Dec. 8, 2000 and issued Nov. 5, 2002.

U.S. Pat. No. 5,432,198 by Jagdmann, G E. Vicinal-substituted carbocyclic compounds as therapeutic agents. Filed Aug. 18, 1994 and issued Jul. 11, 1995.

U.S. Pat. No. 5,583,221 by Hu, H, Jagdmann, G E, and Mendoza J S. Substituted fused and bridged bicyclic compounds as therapeutic agents. Filed Feb. 23, 1995 and issued Dec. 10, 1996.

U.S. Pat. No. 6,376,467 by Messing, R O and Levine, J D. Use of inhibitors of protein kinase C epsilon to treat pain. Filed Jul. 6, 1999 and issued Apr. 23, 2002.

U.S. Pat. No. 6,686,334 by Messing, R O and Levine J D. Use of inhibitors of protein kinase C epsilon to treat pain. Filed Jan. 4, 2002 and issued Feb. 3, 2004.

Urban M O and Gebhart G F (1999) Supraspinal contributions to hyperalgesia. Proc Natl Acad Sci USA 96:7687-7692.

Urban M O and Gebhart G F (1998) The glutamate synapse: a target in the pharmacological management of hyperalgesic pain states. Prog Brain Res 116:407-420.

Verge V M, Xu Z, Xu X J, Wiesenfeld-Hallin Z, Hokfelt T (1992) Marked increase in nitric oxide synthase mRNA in rat dorsal root ganglia after peripheral axotomy: in situ hybridization and functional studies. Proc Natl Acad Sci USA 89:11617-11621.

Wall P D, Devor M (1983) Sensory afferent impulses originate from dorsal root ganglia as well as from the periphery in normal and nerve injured rats. Pain 17:321-339.

Walters E T (1994) Injury-related behavior and neuronal plasticity: an evolutionary perspective on sensitization, hyperalgesia, and analgesia. Int Rev Neurobiol 36:325-427.

Walters E T, Byrne J H, Carew T J, Kandel E R (1983a) Mechanoafferent neurons innervating tail of *Aplysia*. II. Response properties and synaptic connections. J Neurophysiol 50:1522-1542.

Walters E T, Byrne J H, Carew T J, Kandel E R (1983b) Mechanoafferent neurons innervating tail of *Aplysia*. II. Modulation by sensitizing stimulation. J Neurophysiol 50:1543-1559.

Walters E T, Alizadeh H, Castro G A (1991) Similar neuronal alterations induced by axonal injury and learning in *Aplysia*. Science 253:797-799.

Walters E T, Bodnarova M, Billy A J, Dulin M F, Diaz-Rios M, Miller M W, Moroz L L (2004) Somatotopic organization and functional properties of mechanosensory neurons expressing sensorin-A mRNA in *Aplysia californica*. J Comp Neurol 471:219-240.

Wang H, Sun H, Della Penna K, Benz R J, Xu J, Gerhold D L, Holder D J, Koblan K S (2002) Chronic neuropathic pain is accompanied by global changes in gene expression and shares pathobiology with neurodegenerative diseases. Neuroscience 114:529-546.

Waxman S G, Kocsis J D, Black J A (1994) Type III sodium channel mRNA is expressed in embryonic but not adult spinal sensory neurons, and is reexpressed following axotomy. J Neurophysiol 72:466-470.

Wender et al. (2000) The design, synthesis, and evaluation of molecules that enable or enhance cellular uptake: peptoid molecular transporters. Proc Natl Acad Sci USA 97: 13003-13008.

Whitmarsh A J, Shore P, Sharrocks A D, Davis R J (1995) Integration of MAP kinase signal transduction pathways at the serum response element. Science 269:403-407.

Woolf C J (1983) Evidence for a central component of post-injury pain hypersensitivity. Nature 306:686-688.

Xu S, Robbins D, Frost J, Dang A, Lange-Carter C, Cobb M H (1995) MEKK1 phosphorylates MEK1 and MEK2 but does not cause activation of mitogenactivated protein kinase. Proc Natl Acad Sci USA 92:6808-6812.

Yang Z, Madinova A, Kozai T, Joch H, Aebi U, Luscher T F (2002) Felodipine inhibits nuclear translocation of p42/44 mitogen-activated protein kinase and human smooth muscle growth. Cardiovasc. Res. 53(1):227-231.

Yao Z. Dolginov Y, Hanoch T, Yung Y, Ridner G, Lando Z, Zharhary D, Seger R (2000) Detection of partially phosphorylated forms of ERK by monoclonal antibodies reveals spatial regulation of ERK activity by phosphatases. FEBS Lett 468:37-42.

Zaragoza C, Soria E, Lopez E, Browning D, Balbin M, Lopez-Otin C, Lamas S (2002) Activation of the mitogen activated protein kinase extracellular signal-regulated kinase 1 and 2 by the nitric oxide-cGMP-cGMP dependent protein kinase axis regulates the expression of matrix metalloproteinase 13 in vascular endothelial cells. Mol Pharmacol 62:927-935.

Zhang H, Xie W, Xie Y (2005) Spinal cord injury triggers sensitization of wide dynamic range dorsal horn neurons in segments rostral to injury. Aug. 2, 2005 Brain Res, epub ahead of print. PMID 16083864.

Zhang J M, Donnelly D F, Song X J, Lamotte R H (1997) Axotomy increases the excitability of dorsal root ganglion cells with unmyelinated axons. J Neurophysiol 78:2790-2794.

Zhang X, Verge V, Wiesenfeld-Hallin Z, Ju G, Bredt D, Synder S H, Hokfelt T (1993) Nitric oxide synthase-like immunoreactivity in lumbar dorsal root ganglia and spinal cord of rat and monkey and effect of peripheral axotomy. J Comp Neurol 335:563-575.

Zhou B, Zhang Z Y (2002) The activity of the extracellular signal-regulated kinase 2 is regulated by the differential phosphorylation in the activation loop. J. Biol Chem 277: 13889-13899.

Zimmermann M (2001) Pathobiology of neuropathic pain. Eur J Pharmacol 429:23-37.

Various publications are cited herein, the contents of which are hereby incorporated by reference in their entireties.

What is claimed is:

1. A compound represented by the following structure:

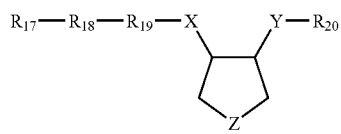

where Z represents —NH—;
X represents

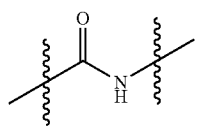 or 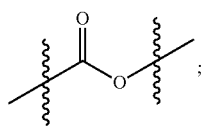;

Y represents

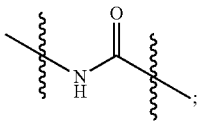 [SMILES: *NC(*)=O]

$R_{17}$ is phenyl, unsubstituted or substituted with one or more of hydroxyl, $(C_1-C_4)$alkoxy, alkoxylalkoxy, or halo;

$R_{18}$ or together with $R_{19}$ is

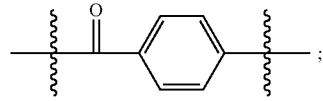

and $R_{20}$ is

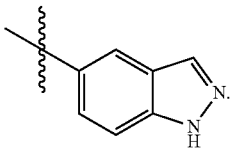 [SMILES: *c1ccc2[nH]ncc2c1]

* * * * *

SEQUENCE LISTING

```
<160> NUMBER OF SEQ ID NOS: 18

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide

<400> SEQUENCE: 1
```

Tyr Gly Arg Lys Lys Arg Arg Gln Arg Arg Pro Pro
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Arg Lys Lys Arg Arg Gln Arg Arg Arg
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Pro Lys Lys Lys Arg Lys
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Cys Thr Pro Pro Lys Lys Lys Arg Lys Val
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Lys Lys Lys Arg Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Pro Pro Lys Lys Lys Arg Lys

```
                     1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Thr Pro Pro Lys Lys Lys Arg Lys
  1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Pro Lys Lys Lys Lys Arg Lys Val
  1               5

<210> SEQ ID NO 10
<211> LENGTH: 13
<212> TYPE: PRT
<213> ORGANISM: Artificial Sequence
<220> FEATURE:
<223> OTHER INFORMATION: Synthetic peptide

<400> SEQUENCE: 10

Arg Lys Ile Ser Ala Ser Glu Phe Asp Arg Pro Leu Arg
  1               5                  10

<210> SEQ ID NO 11
<211> LENGTH: 733
<212> TYPE: PRT
<213> ORGANISM: Aplysia californica

<400> SEQUENCE: 11

Met Gly Asn Gly Ala Ser Ser Asn Thr His Phe Thr Ile Asp Gly Glu
  1               5                  10                  15

Ser Met Asp Val His Lys Val Lys Ala Leu Val Pro Glu Leu Arg His
                 20                  25                  30

Glu Leu Arg Arg Arg Asp Lys Ile Ile Glu Gln Tyr Asp Ser Gln Val
             35                  40                  45

Arg Gln Lys Asp Glu Leu Leu Lys Glu Lys Glu Ala Glu Ile Ala Arg
         50                  55                  60

Leu Lys Glu Glu Val His Lys Leu Lys Ser Val Leu Gln Leu Lys Val
 65                  70                  75                  80

Asp Thr Leu Lys Ala Gln Glu Ser Lys Pro Asp Leu Leu Ser Thr Ile
                 85                  90                  95

Asp Glu Asn Gln Ala Glu Pro Thr Ala Pro Arg Gly Pro Ala Lys Lys
            100                 105                 110

Gln Gly Val Ser Gly Glu Ser Pro Ser Ser Lys Thr Leu Gly Tyr Val
        115                 120                 125

Asp Leu Thr His His Glu Lys Asp Phe Lys Ser Lys Gln Leu Ile Lys
    130                 135                 140

Asp Ala Ile Leu Ser Asn Glu Phe Ile Lys Val Leu Ala Ala Thr Gln
145                 150                 155                 160
```

```
Leu Arg Glu Ile Ile Asp Cys Met Tyr Glu Lys Arg Val Pro Lys Ala
                165                 170                 175

Cys Tyr Ile Ile Lys Gly Gly Glu Arg Gly Glu His Leu Tyr Val Cys
            180                 185                 190

Ala Asp Gly Leu Leu Glu Val His Lys Glu Asp Lys Arg Leu Gly Glu
        195                 200                 205

Ile Lys Ser Gly Gly Leu Phe Gly Glu Leu Ala Ile Leu Tyr Asn Cys
    210                 215                 220

Lys Arg Thr Ala Ser Val Lys Ala Val Thr His Thr Thr Leu Trp Val
225                 230                 235                 240

Leu Asp Arg Arg Val Phe Gln Ala Ile Met Met Lys Thr Gly Leu Gln
                245                 250                 255

Arg Arg Glu Glu Asn Met Ala Phe Leu Lys Ser Val Pro Leu Leu Lys
            260                 265                 270

Asn Leu Pro Ser Asp Lys Leu Ala Lys Met Ser Asp Val Leu Glu Tyr
        275                 280                 285

Asp Phe Phe His Glu Asn Glu Tyr Ile Ile Arg Glu Gly Ala Ala Gly
    290                 295                 300

Asp Thr Phe Phe Ile Leu Asn Lys Gly Glu Val Lys Val Thr Gln Lys
305                 310                 315                 320

Ile Ala Gly His Ala Glu Pro Lys Glu Val Arg Arg Leu Lys Arg Gly
                325                 330                 335

Asp Tyr Phe Gly Glu Lys Ala Leu Leu Ser Glu Asp Arg Arg Thr Ala
            340                 345                 350

Asn Val Ile Ala Leu Pro Pro Gly Val Glu Cys Leu Thr Val Asp Arg
        355                 360                 365

Glu Ser Phe Thr Gln Phe Val Gly Asp Leu Asn Glu Leu Arg Asn Lys
    370                 375                 380

Asp Tyr Gly Asp Glu Ala Arg Gly Ala Glu Arg Arg Ser Gly Ser Asp
385                 390                 395                 400

Ser Thr Val Ser Pro Val Ser Glu Arg Pro Val Ala Lys Glu Phe Glu
                405                 410                 415

Asn Cys Ser Leu Asp Asp Leu Gln Leu Val Thr Thr Leu Gly Met Gly
            420                 425                 430

Gly Phe Gly Arg Val Glu Leu Val Gln Leu Ser Lys Glu Lys Gly Lys
        435                 440                 445

Thr Phe Ala Leu Lys Cys Leu Lys Lys His Ile Val Glu Thr Arg
    450                 455                 460

Gln Gln Glu His Ile Tyr Ser Glu Lys Lys Ile Met Met Glu Ala Asp
465                 470                 475                 480

Ser Pro Phe Ile Thr Lys Leu His Lys Thr Phe Arg Asp Arg Lys Tyr
                485                 490                 495

Val Tyr Met Leu Met Glu Val Cys Leu Gly Gly Glu Leu Trp Thr Ile
            500                 505                 510

Leu Arg Asp Arg Gly Asn Phe Asp Asp Leu Thr Ala Arg Phe Cys Val
        515                 520                 525

Ala Cys Val Leu Glu Ala Phe Ser Tyr Leu His Ala Lys Gly Ile Ile
    530                 535                 540

Tyr Arg Asp Leu Lys Pro Glu Asn Leu Leu Asp Ala Arg Gly Tyr
545                 550                 555                 560

Val Lys Leu Val Asp Phe Gly Phe Ala Lys Lys Ile Gly Val Gly Lys
                565                 570                 575

Lys Thr Trp Thr Phe Cys Gly Thr Pro Glu Tyr Val Ala Pro Glu Ile
```

```
                580                 585                 590
Ile Leu Asn Lys Gly His Asp His Ser Ala Asp Tyr Trp Ser Leu Gly
            595                 600                 605

Ile Leu Met Tyr Glu Leu Leu Asn Gly Thr Pro Pro Phe Ser Gly Ser
            610                 615                 620

Asp Pro Met Arg Thr Tyr Asn Ile Ile Leu Lys Gly Ile Asp His Ile
625                 630                 635                 640

Glu Phe Pro Lys Lys Ile Ser Arg Ser Ala His Val Leu Ile Lys Lys
                645                 650                 655

Leu Cys Arg Asp Asn Pro Met Glu Arg Leu Gly Tyr Gly Lys Asn Gly
            660                 665                 670

Ile Ser Asp Ile Arg Lys Asn Lys Trp Phe Gln Gly Phe Asp Trp Asp
            675                 680                 685

Gly Leu Met Asp Leu Thr Leu Thr Pro Pro Ile Val Pro Lys Val Lys
            690                 695                 700

Asn Pro Thr Asp Thr Ser Asn Phe Asp Ser Tyr Pro Arg Asp Met Asp
705                 710                 715                 720

Ile Ala Ala Asp Glu Leu Ser Gly Trp Asp Ile Asp Phe
                725                 730

<210> SEQ ID NO 12
<211> LENGTH: 768
<212> TYPE: PRT
<213> ORGANISM: Drosophila melanogaster

<400> SEQUENCE: 12

Met Ala Ala Gly Met Leu Thr Asp Arg Glu Arg Glu Ala Ile Val Ser
 1               5                  10                  15

Asn Leu Thr Lys Asp Val Gln Ala Leu Arg Glu Met Val Arg Ser Arg
                20                  25                  30

Glu Ser Glu Leu Val Lys Leu His Arg Glu Ile His Lys Leu Lys Ser
            35                  40                  45

Val Leu Gln Gln Thr Thr Asn Asn Leu Asn Val Thr Arg Asn Glu Lys
 50                  55                  60

Ala Lys Lys Leu Tyr Ser Leu Pro Glu Gln Cys Gly Glu Gln Glu
65                  70                  75                  80

Ser Arg Asn Gln Asn Pro His Leu Cys Ser Ser Cys Gly Met Val Leu
                85                  90                  95

Pro Thr Ser Pro Glu Phe Ala Leu Glu Ala Leu Ser Leu Gly Pro Leu
            100                 105                 110

Ser Pro Leu Ala Ser Thr Ser Ser Ala Ser Pro Ser Gly Arg Thr Ser
            115                 120                 125

Ala Asp Glu Val Arg Pro Lys Ala Met Pro Ala Ala Ile Lys Lys Gln
130                 135                 140

Gly Val Ser Ala Glu Ser Cys Val Gln Ser Met Gln Gln Ser Tyr Ser
145                 150                 155                 160

Ile Pro Ile Pro Lys Tyr Glu Lys Asp Phe Ser Asp Lys Gln Gln Ile
                165                 170                 175

Lys Asp Ala Ile Met Asp Asn Asp Phe Leu Lys Asn Ile Asp Ala Ser
            180                 185                 190

Gln Val Arg Glu Leu Val Asp Ser Met Tyr Ser Lys Ser Ile Ala Ala
            195                 200                 205

Gly Glu Phe Val Ile Arg Glu Gly Glu Val Gly Ala His Leu Tyr Val
            210                 215                 220
```

-continued

Ser Ala Ala Gly Glu Phe Ala Val Met Gln His Gly Lys Val Leu Asp
225                 230                 235                 240

Lys Met Gly Ala Gly Lys Ala Phe Gly Glu Leu Ala Ile Leu Tyr Asn
            245                 250                 255

Cys Thr Arg Thr Ala Ser Ile Arg Val Leu Ser Glu Ala Ala Arg Val
                260                 265                 270

Trp Val Leu Asp Arg Arg Val Phe Gln Gln Ile Met Met Cys Thr Gly
        275                 280                 285

Leu Gln Arg Ile Glu Asn Ser Val Asn Phe Leu Arg Ser Val Pro Leu
290                 295                 300

Leu Met Asn Leu Ser Glu Glu Leu Leu Ala Lys Ile Ala Asp Val Leu
305                 310                 315                 320

Glu Leu Glu Phe Tyr Ala Ala Gly Thr Tyr Ile Ile Arg Gln Gly Thr
                325                 330                 335

Ala Gly Asp Ser Phe Phe Leu Ile Ser Gln Gly Asn Val Arg Val Thr
                340                 345                 350

Gln Lys Leu Thr Pro Thr Ser Pro Glu Glu Thr Glu Leu Arg Thr Leu
            355                 360                 365

Ser Arg Gly Asp Tyr Phe Gly Glu Gln Ala Leu Ile Asn Glu Asp Lys
370                 375                 380

Arg Thr Ala Asn Ile Ile Ala Leu Ser Pro Gly Val Glu Cys Leu Thr
385                 390                 395                 400

Leu Asp Arg Asp Ser Phe Lys Arg Leu Ile Gly Asp Leu Cys Glu Leu
                405                 410                 415

Lys Glu Lys Asp Tyr Gly Asp Glu Ser Arg Lys Leu Ala Met Lys Gln
            420                 425                 430

Ala Arg Glu Ser Cys Gln Asp Glu Pro Lys Glu Gln Leu Gln Gln Glu
            435                 440                 445

Phe Pro Asp Leu Lys Leu Thr Asp Leu Glu Val Val Ser Thr Leu Gly
    450                 455                 460

Ile Gly Gly Phe Gly Arg Val Glu Leu Val Lys Ala His His Gln Asp
465                 470                 475                 480

Arg Val Asp Ile Phe Ala Leu Lys Cys Leu Lys Lys Arg His Ile Val
                485                 490                 495

Asp Thr Lys Gln Glu Glu His Ile Phe Ser Glu Arg His Ile Met Leu
                500                 505                 510

Ser Ser Arg Ser Pro Phe Ile Cys Arg Leu Tyr Arg Thr Phe Arg Asp
            515                 520                 525

Glu Lys Tyr Val Tyr Met Leu Leu Glu Ala Cys Met Gly Gly Glu Ile
    530                 535                 540

Trp Thr Met Leu Arg Asp Arg Gly Ser Phe Glu Asp Asn Ala Ala Gln
545                 550                 555                 560

Phe Ile Ile Gly Cys Val Leu Gln Ala Phe Glu Tyr Leu His Ala Arg
                565                 570                 575

Gly Ile Ile Tyr Arg Asp Leu Lys Pro Glu Asn Leu Met Leu Asp Glu
                580                 585                 590

Arg Gly Tyr Val Lys Ile Val Asp Phe Gly Phe Ala Lys Gln Ile Gly
            595                 600                 605

Thr Ser Ser Lys Thr Trp Thr Phe Cys Gly Thr Pro Glu Tyr Val Ala
    610                 615                 620

Pro Glu Ile Ile Leu Asn Lys Gly His Asp Arg Ala Val Asp Tyr Trp
625                 630                 635                 640

Ala Leu Gly Ile Leu Ile His Glu Leu Leu Asn Gly Thr Pro Pro Phe

```
                        645                 650                 655
Ser Ala Pro Asp Pro Met Gln Thr Tyr Asn Leu Ile Leu Lys Gly Ile
            660                 665                 670

Asp Met Ile Ala Phe Pro Lys His Ile Ser Arg Trp Ala Val Gln Leu
            675                 680                 685

Ile Lys Arg Leu Cys Arg Asp Val Pro Ser Glu Arg Leu Gly Tyr Gln
            690                 695                 700

Thr Gly Ile Gln Asp Ile Lys Lys His Lys Trp Phe Leu Gly Phe
705                 710                 715                 720

Asp Trp Asp Gly Leu Ala Ser Gln Leu Leu Ile Pro Pro Phe Val Arg
                725                 730                 735

Pro Ile Ala His Pro Thr Asp Val Arg Tyr Phe Asp Arg Phe Pro Cys
                740                 745                 750

Asp Leu Asn Glu Pro Pro Asp Glu Leu Ser Gly Trp Asp Ala Asp Phe
                755                 760                 765
```

<210> SEQ ID NO 13
<211> LENGTH: 671
<212> TYPE: PRT
<213> ORGANISM: Homo sapiens

<400> SEQUENCE: 13

```
Met Ser Glu Leu Glu Glu Asp Phe Ala Lys Ile Leu Met Leu Lys Glu
1               5                   10                  15

Glu Arg Ile Lys Glu Leu Glu Lys Arg Leu Ser Glu Lys Glu Glu Glu
            20                  25                  30

Ile Gln Glu Leu Lys Arg Lys Leu His Lys Cys Gln Ser Val Leu Pro
        35                  40                  45

Val Pro Ser Thr His Ile Gly Pro Arg Thr Thr Arg Ala Gln Gly Ile
    50                  55                  60

Ser Ala Glu Pro Gln Thr Tyr Arg Ser Phe His Asp Leu Arg Gln Ala
65                  70                  75                  80

Phe Arg Lys Phe Thr Lys Ser Glu Arg Ser Lys Asp Leu Ile Lys Glu
                85                  90                  95

Ala Ile Leu Asp Asn Asp Phe Met Lys Asn Leu Glu Leu Ser Gln Ile
            100                 105                 110

Gln Glu Ile Val Asp Cys Met Tyr Pro Val Glu Tyr Gly Lys Asp Ser
        115                 120                 125

Cys Ile Ile Lys Glu Gly Asp Val Gly Ser Leu Val Tyr Val Met Glu
    130                 135                 140

Asp Gly Lys Val Glu Val Thr Lys Glu Gly Val Lys Leu Cys Thr Met
145                 150                 155                 160

Gly Pro Gly Lys Val Phe Gly Glu Leu Ala Ile Leu Tyr Asn Cys Thr
                165                 170                 175

Arg Thr Ala Thr Val Lys Thr Leu Val Asn Val Lys Leu Trp Ala Ile
            180                 185                 190

Asp Arg Gln Cys Phe Gln Thr Ile Met Met Arg Thr Gly Leu Ile Lys
        195                 200                 205

His Thr Glu Tyr Met Glu Phe Leu Lys Ser Val Pro Thr Phe Gln Ser
    210                 215                 220

Leu Pro Glu Glu Ile Leu Ser Lys Leu Ala Asp Val Leu Glu Glu Thr
225                 230                 235                 240

His Tyr Glu Asn Gly Glu Tyr Ile Ile Arg Gln Gly Ala Arg Gly Asp
                245                 250                 255
```

```
Thr Phe Phe Ile Ile Ser Lys Gly Thr Val Asn Val Thr Arg Glu Asp
                260                 265                 270

Ser Pro Ser Glu Asp Pro Val Phe Leu Arg Thr Leu Gly Lys Gly Asp
    275                 280                 285

Trp Phe Gly Glu Lys Ala Leu Gln Gly Glu Asp Val Arg Thr Ala Asn
290                 295                 300

Val Ile Ala Ala Glu Ala Val Thr Cys Leu Val Ile Asp Arg Asp Ser
305                 310                 315                 320

Phe Lys His Leu Ile Gly Gly Leu Asp Asp Val Ser Asn Lys Ala Tyr
                325                 330                 335

Glu Asp Ala Glu Ala Lys Ala Lys Tyr Glu Ala Glu Ala Ala Phe Phe
            340                 345                 350

Ala Asn Leu Lys Leu Ser Asp Phe Asn Ile Ile Asp Thr Leu Gly Val
                355                 360                 365

Gly Gly Phe Gly Arg Val Glu Leu Val Gln Leu Lys Ser Glu Glu Ser
370                 375                 380

Lys Thr Phe Ala Met Lys Ile Leu Lys Lys Arg His Ile Val Asp Thr
385                 390                 395                 400

Arg Gln Gln Glu His Ile Arg Ser Glu Lys Gln Ile Met Gln Gly Ala
                405                 410                 415

His Ser Asp Phe Ile Val Arg Leu Tyr Arg Thr Phe Lys Asp Ser Lys
            420                 425                 430

Tyr Leu Tyr Met Leu Met Glu Ala Cys Leu Gly Gly Glu Leu Trp Thr
                435                 440                 445

Ile Leu Arg Asp Arg Gly Ser Phe Glu Asp Ser Thr Thr Arg Phe Tyr
450                 455                 460

Thr Ala Cys Val Val Glu Ala Phe Ala Tyr Leu His Ser Lys Gly Ile
465                 470                 475                 480

Ile Tyr Arg Asp Leu Lys Pro Glu Asn Leu Ile Leu Asp His Arg Gly
                485                 490                 495

Tyr Ala Lys Leu Val Asp Phe Gly Phe Ala Lys Lys Ile Gly Phe Gly
            500                 505                 510

Lys Lys Thr Trp Thr Phe Cys Gly Thr Pro Glu Tyr Val Ala Pro Glu
                515                 520                 525

Ile Ile Leu Asn Lys Gly His Asp Ile Ser Ala Asp Tyr Trp Ser Leu
530                 535                 540

Gly Ile Leu Met Tyr Glu Leu Leu Thr Gly Ser Pro Pro Phe Ser Gly
545                 550                 555                 560

Pro Asp Pro Met Lys Thr Tyr Asn Ile Ile Leu Arg Gly Ile Asp Met
                565                 570                 575

Ile Glu Phe Pro Lys Lys Ile Ala Lys Asn Ala Ala Asn Leu Ile Lys
            580                 585                 590

Lys Leu Cys Arg Asp Asn Pro Ser Glu Arg Leu Gly Asn Leu Lys Asn
                595                 600                 605

Gly Val Lys Asp Ile Gln Lys His Lys Trp Phe Glu Gly Phe Asn Trp
610                 615                 620

Glu Gly Leu Arg Lys Gly Thr Leu Thr Pro Pro Ile Ile Pro Ser Val
625                 630                 635                 640

Ala Ser Pro Thr Asp Thr Ser Asn Phe Asp Ser Phe Pro Glu Asp Asn
                645                 650                 655

Asp Glu Pro Pro Pro Asp Asp Asn Ser Gly Trp Asp Ile Asp Phe
            660                 665                 670
```

<210> SEQ ID NO 14
<211> LENGTH: 686
<212> TYPE: PRT
<213> ORGANISM: Mus musculus

<400> SEQUENCE: 14

Met Gly Thr Leu Arg Asp Leu Gln Tyr Ala Leu Gln Glu Lys Ile Glu
1               5                   10                  15

Glu Leu Arg Gln Arg Asp Ala Leu Ile Asp Glu Leu Glu Leu Glu Leu
            20                  25                  30

Asp Gln Lys Asp Glu Leu Ile Gln Lys Leu Gln Asn Glu Leu Asp Lys
        35                  40                  45

Tyr Arg Ser Val Ile Arg Pro Ala Thr Gln Ala Gln Lys Gln Ser
    50                  55                  60

Ala Ser Thr Leu Gln Gly Glu Pro Arg Thr Lys Arg Gln Ala Ile Ser
65              70                  75                  80

Ala Glu Pro Thr Ala Phe Asp Ile Gln Asp Leu Ser His Val Thr Leu
                85                  90                  95

Pro Phe Tyr Pro Lys Ser Pro Gln Ser Lys Asp Leu Ile Lys Glu Ala
            100                 105                 110

Ile Leu Asp Asn Asp Phe Met Lys Asn Leu Glu Leu Ser Gln Ile Gln
        115                 120                 125

Glu Ile Val Asp Cys Met Tyr Pro Val Glu Tyr Gly Lys Asp Ser Cys
130                 135                 140

Ile Ile Lys Glu Gly Asp Val Gly Ser Leu Val Tyr Val Met Glu Asp
145                 150                 155                 160

Gly Lys Val Glu Val Thr Lys Glu Gly Val Lys Leu Cys Thr Met Gly
                165                 170                 175

Pro Gly Lys Val Phe Gly Glu Leu Ala Ile Leu Tyr Asn Cys Thr Arg
            180                 185                 190

Thr Ala Thr Val Lys Thr Leu Val Asn Val Lys Leu Trp Ala Ile Asp
        195                 200                 205

Arg Gln Cys Phe Gln Thr Ile Met Met Arg Thr Gly Leu Ile Lys His
    210                 215                 220

Thr Glu Tyr Met Glu Phe Leu Lys Ser Val Pro Thr Phe Gln Ser Leu
225                 230                 235                 240

Pro Asp Glu Ile Leu Ser Lys Leu Ala Asp Val Leu Glu Glu Thr His
                245                 250                 255

Tyr Glu Asn Gly Glu Tyr Ile Ile Arg Gln Gly Ala Arg Gly Asp Thr
            260                 265                 270

Phe Phe Ile Ile Ser Lys Gly Gln Val Asn Val Thr Arg Glu Asp Ser
        275                 280                 285

Pro Ser Glu Asp Pro Val Phe Leu Arg Thr Leu Gly Lys Gly Asp Trp
    290                 295                 300

Phe Gly Glu Lys Ala Leu Gln Gly Glu Asp Val Arg Thr Ala Asn Val
305                 310                 315                 320

Ile Ala Ala Glu Ala Val Thr Cys Leu Val Ile Asp Arg Asp Ser Phe
                325                 330                 335

Lys His Leu Ile Gly Gly Leu Asp Asp Val Ser Asn Lys Ala Tyr Glu
            340                 345                 350

Asp Ala Glu Ala Lys Ala Lys Tyr Glu Ala Glu Ala Ala Phe Phe Ala
        355                 360                 365

Asn Leu Lys Leu Ser Asp Phe Asn Ile Ile Asp Thr Leu Gly Val Gly
    370                 375                 380

```
Gly Phe Gly Arg Val Glu Leu Val Gln Leu Lys Ser Glu Glu Ser Lys
385                 390                 395                 400

Thr Phe Ala Met Lys Ile Leu Lys Lys Arg His Ile Val Asp Thr Arg
            405                 410                 415

Gln Gln Glu His Ile Arg Ser Glu Lys Gln Ile Met Gln Gly Ala His
        420                 425                 430

Ser Asp Phe Ile Val Arg Leu Tyr Arg Thr Phe Lys Asp Ser Lys Tyr
    435                 440                 445

Leu Tyr Met Leu Met Glu Ala Cys Leu Gly Gly Glu Leu Trp Thr Ile
450                 455                 460

Leu Arg Asp Arg Gly Ser Phe Glu Asp Ser Thr Thr Arg Phe Tyr Thr
465                 470                 475                 480

Ala Cys Val Val Glu Ala Phe Ala Tyr Leu His Ser Lys Gly Ile Ile
                485                 490                 495

Tyr Arg Asp Leu Lys Pro Glu Asn Leu Ile Leu Asp His Arg Gly Tyr
            500                 505                 510

Ala Lys Leu Val Asp Phe Gly Phe Ala Lys Lys Ile Gly Phe Gly Lys
        515                 520                 525

Lys Thr Trp Thr Phe Cys Gly Thr Pro Glu Tyr Val Ala Pro Glu Ile
530                 535                 540

Ile Leu Asn Lys Gly His Asp Ile Ser Ala Asp Tyr Trp Ser Leu Gly
545                 550                 555                 560

Ile Leu Met Tyr Glu Leu Leu Thr Gly Ser Pro Pro Phe Ser Gly Pro
                565                 570                 575

Asp Pro Met Lys Thr Tyr Asn Ile Ile Leu Arg Gly Ile Asp Met Ile
            580                 585                 590

Glu Phe Pro Lys Lys Ile Ala Lys Asn Ala Ala Asn Leu Ile Lys Lys
        595                 600                 605

Leu Cys Arg Asp Asn Pro Ser Glu Arg Leu Gly Asn Leu Lys Asn Gly
610                 615                 620

Val Lys Asp Ile Gln Lys His Lys Trp Phe Glu Gly Phe Asn Trp Glu
625                 630                 635                 640

Gly Leu Arg Lys Gly Thr Leu Thr Pro Pro Ile Ile Pro Ser Val Ala
                645                 650                 655

Ser Pro Thr Asp Thr Ser Asn Phe Asp Ser Phe Pro Glu Asp Ser Asp
            660                 665                 670

Glu Pro Pro Pro Asp Asp Asn Ser Gly Trp Asp Ile Asp Phe
        675                 680                 685

<210> SEQ ID NO 15
<211> LENGTH: 742
<212> TYPE: PRT
<213> ORGANISM: Drosophila melanogaster

<400> SEQUENCE: 15

Met Gln Ser Leu Arg Ile Ser Gly Cys Thr Pro Ser Gly Thr Gly Gly
1               5                   10                  15

Ser Ala Thr Pro Ser Pro Val Gly Leu Val Asp Pro Asn Phe Ile Val
            20                  25                  30

Ser Asn Tyr Val Ala Ala Ser Pro Gln Glu Glu Arg Phe Ile Gln Ile
        35                  40                  45

Ile Gln Ala Lys Glu Leu Lys Ile Gln Glu Met Gln Arg Ala Leu Gln
    50                  55                  60

Phe Lys Asp Asn Glu Ile Ala Glu Leu Lys Ser His Leu Asp Lys Phe
65                  70                  75                  80
```

```
Gln Ser Val Phe Pro Phe Ser Arg Gly Ser Ala Ala Gly Cys Ala Gly
                    85                  90                  95

Thr Gly Gly Ala Ser Gly Ser Gly Ala Gly Ser Gly Gly Ser Gly
            100                 105                 110

Pro Gly Thr Ala Thr Gly Ala Thr Arg Lys Ser Gly Gln Asn Phe Gln
            115                 120                 125

Arg Gln Arg Ala Leu Gly Ile Ser Ala Glu Pro Gln Ser Glu Ser Ser
130                 135                 140

Leu Leu Leu Glu His Val Ser Phe Pro Lys Tyr Asp Lys Asp Glu Arg
145                 150                 155                 160

Ser Arg Glu Leu Ile Lys Ala Ala Ile Leu Asp Asn Asp Phe Met Lys
                165                 170                 175

Asn Leu Asp Leu Thr Gln Ile Arg Glu Ile Val Asp Cys Met Tyr Pro
            180                 185                 190

Val Lys Tyr Pro Ala Lys Asn Leu Ile Ile Lys Glu Gly Asp Val Gly
            195                 200                 205

Ser Ile Val Tyr Val Met Glu Asp Gly Arg Val Glu Val Ser Arg Glu
210                 215                 220

Gly Lys Tyr Leu Ser Thr Leu Ser Gly Ala Lys Val Leu Gly Glu Leu
225                 230                 235                 240

Ala Ile Leu Tyr Asn Cys Gln Arg Thr Ala Thr Ile Thr Ala Ile Thr
                245                 250                 255

Glu Cys Asn Leu Trp Ala Ile Glu Arg Gln Cys Phe Gln Thr Ile Met
            260                 265                 270

Met Arg Thr Gly Leu Ile Arg Gln Ala Glu Tyr Ser Asp Phe Leu Lys
            275                 280                 285

Ser Val Pro Ile Phe Lys Asp Leu Ala Glu Asp Thr Leu Ile Lys Ile
290                 295                 300

Ser Asp Val Leu Glu Glu Thr His Tyr Gln Arg Gly Asp His Ile Val
305                 310                 315                 320

Arg Gln Gly Ala Arg Gly Asp Thr Phe Phe Ile Ile Ser Lys Gly Lys
                325                 330                 335

Val Arg Val Thr Ile Lys Gln Gln Asp Arg Gln Glu Glu Lys Phe Ile
            340                 345                 350

Arg Met Leu Gly Lys Gly Asp Phe Phe Gly Glu Lys Ala Leu Gln Gly
            355                 360                 365

Asp Asp Leu Arg Thr Ala Asn Ile Ile Cys Glu Ser Ala Asp Gly Val
370                 375                 380

Ser Cys Leu Val Ile Asp Arg Glu Thr Phe Asn Gln Leu Ile Ser Asn
385                 390                 395                 400

Leu Asp Glu Ile Lys His Arg Tyr Asp Asp Glu Gly Ala Met Glu Arg
                405                 410                 415

Arg Lys Ile Asn Glu Glu Phe Arg Asp Ile Asn Leu Thr Asp Leu Arg
            420                 425                 430

Val Ile Ala Thr Leu Gly Val Gly Gly Phe Gly Arg Val Glu Leu Val
            435                 440                 445

Gln Thr Asn Gly Asp Ser Ser Arg Ser Phe Ala Leu Lys Gln Met Lys
450                 455                 460

Lys Ser Gln Ile Val Glu Thr Arg Gln Gln Gln His Ile Met Ser Glu
465                 470                 475                 480

Lys Glu Ile Met Gly Glu Ala Asn Cys Gln Phe Ile Val Lys Leu Phe
                485                 490                 495
```

```
Lys Thr Phe Lys Asp Lys Lys Tyr Leu Tyr Met Leu Met Glu Ser Cys
                500                 505                 510

Leu Gly Gly Glu Leu Trp Thr Ile Leu Arg Asp Lys Gly Asn Phe Asp
            515                 520                 525

Asp Ser Thr Thr Arg Phe Tyr Thr Ala Cys Val Val Glu Ala Phe Asp
        530                 535                 540

Tyr Leu His Ser Arg Asn Ile Ile Tyr Arg Asp Leu Lys Pro Glu Asn
545                 550                 555                 560

Leu Leu Leu Asn Glu Arg Gly Tyr Gly Lys Leu Val Asp Phe Gly Phe
                565                 570                 575

Ala Lys Lys Leu Gln Thr Gly Arg Lys Thr Trp Thr Phe Cys Gly Thr
            580                 585                 590

Pro Glu Tyr Val Ala Pro Glu Val Ile Leu Asn Arg Gly His Asp Ile
        595                 600                 605

Ser Ala Asp Tyr Trp Ser Leu Gly Val Leu Met Phe Glu Leu Leu Thr
    610                 615                 620

Gly Thr Pro Pro Phe Thr Gly Ser Asp Pro Met Arg Thr Tyr Asn Ile
625                 630                 635                 640

Ile Leu Lys Gly Ile Asp Ala Ile Glu Phe Pro Arg Asn Ile Thr Arg
                645                 650                 655

Asn Ala Ser Asn Leu Ile Lys Lys Leu Cys Arg Asp Asn Pro Ala Glu
            660                 665                 670

Arg Leu Gly Tyr Gln Arg Gly Gly Ile Ser Glu Ile Gln Lys His Lys
        675                 680                 685

Trp Phe Asp Gly Phe Tyr Trp Trp Gly Leu Gln Asn Cys Thr Leu Glu
    690                 695                 700

Pro Pro Ile Lys Pro Ala Val Lys Ser Val Val Asp Thr Thr Asn Phe
705                 710                 715                 720

Asp Asp Tyr Pro Pro Asp Pro Glu Gly Pro Pro Asp Asp Val Thr
                725                 730                 735

Gly Trp Asp Lys Asp Phe
            740

<210> SEQ ID NO 16
<211> LENGTH: 762
<212> TYPE: PRT
<213> ORGANISM: Homo sapiens

<400> SEQUENCE: 16

Met Gly Asn Gly Ser Val Lys Pro Lys His Ser Lys His Pro Asp Gly
1               5                   10                  15

His Ser Gly Asn Leu Thr Thr Asp Ala Leu Arg Asn Lys Val Thr Glu
            20                  25                  30

Leu Glu Arg Glu Leu Arg Arg Lys Asp Ala Glu Ile Gln Glu Arg Glu
        35                  40                  45

Tyr His Leu Lys Glu Leu Arg Glu Gln Leu Ser Lys Gln Thr Val Ala
    50                  55                  60

Ile Ala Glu Leu Thr Glu Glu Leu Gln Asn Lys Cys Ile Gln Leu Asn
65                  70                  75                  80

Lys Leu Gln Asp Val Val His Met Gln Gly Gly Ser Pro Leu Gln Ala
                85                  90                  95

Ser Pro Asp Lys Val Pro Leu Glu Val His Arg Lys Thr Ser Gly Leu
            100                 105                 110

Val Ser Leu His Ser Arg Arg Gly Ala Lys Ala Gly Val Ser Ala Glu
        115                 120                 125
```

```
Pro Thr Thr Arg Thr Tyr Asp Leu Asn Lys Pro Pro Glu Phe Ser Phe
    130                 135                 140

Glu Lys Ala Arg Val Arg Lys Asp Ser Ser Glu Lys Lys Leu Ile Thr
145                 150                 155                 160

Asp Ala Leu Asn Lys Asn Gln Phe Leu Lys Arg Leu Asp Pro Gln Gln
                165                 170                 175

Ile Lys Asp Met Val Glu Cys Met Tyr Gly Arg Asn Tyr Gln Gln Gly
            180                 185                 190

Ser Tyr Ile Ile Lys Gln Gly Glu Pro Gly Asn His Ile Phe Val Leu
        195                 200                 205

Ala Glu Gly Arg Leu Glu Val Phe Gln Gly Gly Lys Leu Leu Ser Ser
210                 215                 220

Ile Pro Met Trp Thr Thr Phe Gly Glu Leu Ala Ile Leu Tyr Asn Cys
225                 230                 235                 240

Thr Arg Thr Ala Ser Val Lys Ala Ile Thr Asn Val Lys Thr Trp Ala
                245                 250                 255

Leu Asp Arg Glu Val Phe Gln Asn Ile Met Arg Arg Thr Ala Gln Ala
            260                 265                 270

Arg Asp Glu Gln Tyr Arg Asn Phe Leu Arg Ser Val Ser Leu Leu Lys
        275                 280                 285

Asn Leu Pro Glu Asp Lys Leu Thr Lys Ile Ile Asp Cys Leu Glu Val
290                 295                 300

Glu Tyr Tyr Asp Lys Gly Asp Tyr Ile Ile Arg Glu Gly Glu Glu Gly
305                 310                 315                 320

Ser Thr Phe Phe Ile Leu Ala Lys Gly Lys Val Lys Val Thr Gln Ser
                325                 330                 335

Thr Glu Gly His Asp Gln Pro Gln Leu Ile Lys Thr Leu Gln Lys Gly
            340                 345                 350

Glu Tyr Phe Gly Glu Lys Ala Leu Ile Ser Asp Asp Val Arg Ser Ala
        355                 360                 365

Asn Ile Ile Ala Glu Glu Asn Asp Val Ala Cys Leu Val Ile Asp Arg
370                 375                 380

Glu Thr Phe Asn Gln Thr Val Gly Thr Phe Glu Glu Leu Gln Lys Tyr
385                 390                 395                 400

Leu Glu Gly Tyr Val Ala Asn Leu Asn Arg Asp Asp Glu Lys Arg His
                405                 410                 415

Ala Lys Arg Ser Met Ser Asn Trp Lys Leu Ser Lys Ala Leu Ser Leu
            420                 425                 430

Glu Met Ile Gln Leu Lys Glu Lys Val Ala Arg Phe Ser Ser Ser Ser
        435                 440                 445

Pro Phe Gln Asn Leu Glu Ile Ile Ala Thr Leu Gly Val Gly Gly Phe
450                 455                 460

Gly Arg Val Glu Leu Val Lys Val Lys Asn Glu Asn Val Ala Phe Ala
465                 470                 475                 480

Met Lys Cys Ile Arg Lys Lys His Ile Val Asp Thr Lys Gln Gln Glu
                485                 490                 495

His Val Tyr Ser Glu Lys Arg Ile Leu Glu Glu Leu Cys Ser Pro Phe
            500                 505                 510

Ile Val Lys Leu Tyr Arg Thr Phe Lys Asp Asn Lys Tyr Val Tyr Met
        515                 520                 525

Leu Leu Glu Ala Cys Leu Gly Gly Glu Leu Trp Ser Ile Leu Arg Asp
530                 535                 540
```

```
Arg Gly Ser Phe Asp Glu Pro Thr Ser Lys Phe Cys Val Ala Cys Val
545                 550                 555                 560

Thr Glu Ala Phe Asp Tyr Leu His Arg Leu Gly Ile Ile Tyr Arg Asp
                565                 570                 575

Leu Lys Pro Glu Asn Leu Ile Leu Asp Ala Glu Gly Tyr Leu Lys Leu
            580                 585                 590

Val Asp Phe Gly Phe Ala Lys Lys Ile Gly Ser Gly Gln Lys Thr Trp
        595                 600                 605

Thr Phe Cys Gly Thr Pro Glu Tyr Val Ala Pro Glu Val Ile Leu Asn
    610                 615                 620

Lys Gly His Asp Phe Ser Val Asp Phe Trp Ser Leu Gly Ile Leu Val
625                 630                 635                 640

Tyr Glu Leu Leu Thr Gly Asn Pro Pro Phe Ser Gly Val Asp Gln Met
                645                 650                 655

Met Thr Tyr Asn Leu Ile Leu Lys Gly Ile Glu Lys Met Asp Phe Pro
                660                 665                 670

Arg Lys Ile Thr Arg Arg Pro Glu Asp Leu Ile Arg Arg Leu Cys Arg
            675                 680                 685

Gln Asn Pro Thr Glu Arg Leu Gly Asn Leu Lys Asn Gly Ile Asn Asp
        690                 695                 700

Ile Lys Lys His Arg Trp Leu Asn Gly Phe Asn Trp Glu Gly Leu Lys
705                 710                 715                 720

Ala Arg Ser Leu Pro Ser Pro Leu Gln Arg Glu Leu Lys Gly Pro Ile
                725                 730                 735

Asp His Ser Tyr Phe Asp Lys Tyr Pro Pro Glu Lys Gly Met Pro Pro
            740                 745                 750

Asp Glu Leu Ser Gly Trp Asp Lys Asp Phe
        755                 760

<210> SEQ ID NO 17
<211> LENGTH: 762
<212> TYPE: PRT
<213> ORGANISM: Mus musculus

<400> SEQUENCE: 17

Met Gly Asn Gly Ser Val Lys Pro Lys His Ala Lys His Pro Asp Gly
1               5                   10                  15

His Ser Gly Asn Leu Ser Asn Glu Ala Leu Arg Ser Lys Val Leu Glu
            20                  25                  30

Leu Glu Arg Glu Leu Arg Arg Lys Asp Ala Glu Leu Gln Glu Arg Glu
        35                  40                  45

Tyr His Leu Lys Glu Leu Arg Glu Gln Leu Ala Lys Gln Thr Val Ala
    50                  55                  60

Ile Ala Glu Leu Thr Glu Leu Gln Ser Lys Cys Ile Gln Leu Asn
65                  70                  75                  80

Lys Leu Gln Asp Val Ile His Val Gln Gly Gly Ser Pro Leu Gln Ala
                85                  90                  95

Ser Pro Asp Lys Val Pro Leu Asp Val His Arg Lys Thr Ser Gly Leu
            100                 105                 110

Val Ser Leu His Ser Arg Arg Gly Ala Lys Ala Gly Val Ser Ala Glu
        115                 120                 125

Pro Thr Thr Arg Thr Tyr Asp Leu Asn Lys Pro Pro Glu Phe Ser Phe
    130                 135                 140

Glu Lys Ala Arg Val Arg Lys Asp Ser Ser Glu Lys Lys Leu Ile Thr
145                 150                 155                 160
```

```
Asp Ala Leu Asn Lys Asn Gln Phe Leu Lys Arg Leu Asp Pro Gln Gln
                165                 170                 175

Ile Lys Asp Met Val Glu Cys Met Tyr Gly Lys Leu Ser Thr Gly
        180                 185                 190

Ser Tyr Val Ile Lys Gln Gly Glu Pro Gly Asn His Ile Phe Val Leu
            195                 200                 205

Ala Glu Gly Arg Leu Glu Val Phe Gln Gly Lys Leu Leu Ser Ser
    210                 215                 220

Ile Pro Met Trp Thr Thr Phe Gly Glu Leu Ala Ile Leu Tyr Asn Cys
225                 230                 235                 240

Thr Arg Thr Ala Ser Val Lys Ala Ile Thr Asn Val Lys Thr Trp Ala
                245                 250                 255

Leu Asp Arg Glu Val Phe Gln Asn Ile Met Arg Arg Thr Ala Gln Ala
                260                 265                 270

Arg Asp Glu Glu Tyr Arg Asn Phe Leu Arg Ser Val Ser Leu Leu Lys
                275                 280                 285

Asn Leu Pro Glu Asp Lys Leu Thr Lys Ile Ile Asp Cys Leu Glu Val
        290                 295                 300

Glu Tyr Tyr Asp Lys Gly Asp Tyr Ile Ile Arg Glu Gly Glu Glu Gly
305                 310                 315                 320

Ser Thr Phe Phe Ile Leu Ala Lys Gly Lys Val Lys Val Thr Gln Ser
                325                 330                 335

Thr Glu Gly His Asp Gln Pro Gln Leu Ile Lys Thr Leu Gln Lys Gly
            340                 345                 350

Glu Tyr Phe Gly Glu Lys Ala Leu Ile Ser Asp Asp Val Arg Ser Ala
                355                 360                 365

Asn Ile Ile Ala Glu Glu Asn Asp Val Ala Cys Leu Val Ile Asp Arg
        370                 375                 380

Glu Thr Phe Asn Gln Thr Val Gly Thr Phe Asp Glu Leu Gln Lys Tyr
385                 390                 395                 400

Leu Glu Gly Tyr Val Ala Thr Leu Asn Arg Asp Asp Glu Lys Arg His
                405                 410                 415

Ala Lys Arg Ser Met Ser Ser Trp Lys Leu Ser Lys Ala Leu Ser Leu
            420                 425                 430

Glu Met Ile Gln Leu Lys Glu Lys Val Ala Arg Phe Ser Ser Thr Ser
        435                 440                 445

Pro Phe Gln Asn Leu Glu Ile Ile Ala Thr Leu Gly Val Gly Gly Phe
    450                 455                 460

Gly Arg Val Glu Leu Val Lys Val Lys Asn Glu Asn Val Ala Phe Ala
465                 470                 475                 480

Met Lys Cys Ile Arg Lys Lys His Ile Val Asp Thr Lys Gln Gln Glu
                485                 490                 495

His Val Tyr Ser Glu Lys Arg Ile Leu Glu Glu Leu Cys Ser Pro Phe
            500                 505                 510

Ile Val Lys Leu Tyr Arg Thr Phe Lys Asp Asn Lys Tyr Val Tyr Met
        515                 520                 525

Leu Leu Glu Ala Cys Leu Gly Gly Glu Leu Trp Ser Ile Leu Arg Asp
530                 535                 540

Arg Gly Ser Phe Asp Glu Pro Thr Ser Lys Phe Cys Val Ala Cys Val
545                 550                 555                 560

Thr Glu Ala Phe Asp Tyr Leu His Leu Leu Gly Ile Ile Tyr Arg Asp
                565                 570                 575
```

-continued

```
Leu Lys Pro Glu Asn Leu Ile Leu Asp Ala Asp Gly Tyr Leu Lys Leu
            580                 585                 590

Val Asp Phe Gly Phe Ala Lys Lys Ile Gly Ser Gly Gln Lys Thr Trp
            595                 600                 605

Thr Phe Cys Gly Thr Pro Glu Tyr Val Ala Pro Glu Val Ile Leu Asn
        610                 615                 620

Lys Gly His Asp Phe Ser Val Asp Phe Trp Ser Leu Gly Ile Leu Val
625                 630                 635                 640

Tyr Glu Leu Leu Thr Gly Asn Pro Pro Phe Ser Gly Ile Asp Gln Met
                645                 650                 655

Met Thr Tyr Asn Leu Ile Leu Lys Gly Ile Glu Lys Met Asp Phe Pro
            660                 665                 670

Arg Lys Ile Thr Arg Arg Pro Glu Asp Leu Ile Arg Arg Leu Cys Arg
            675                 680                 685

Gln Asn Pro Thr Glu Arg Leu Gly Asn Leu Lys Asn Gly Ile Asn Asp
        690                 695                 700

Ile Lys Lys His Arg Trp Leu Asn Gly Phe Asn Trp Glu Gly Leu Lys
705                 710                 715                 720

Ala Arg Ser Leu Pro Ser Pro Leu Arg Arg Glu Leu Ser Gly Pro Ile
                725                 730                 735

Asp His Ser Tyr Phe Asp Lys Tyr Pro Pro Glu Lys Gly Val Pro Pro
            740                 745                 750

Asp Glu Met Ser Gly Trp Asp Lys Asp Phe
            755                 760
```

<210> SEQ ID NO 18
<211> LENGTH: 762
<212> TYPE: PRT
<213> ORGANISM: Rattus norvegicus

<400> SEQUENCE: 18

```
Met Gly Asn Gly Ser Val Lys Pro Lys His Ser Lys His Pro Asp Gly
  1               5                  10                  15

Gln Ser Gly Asn Leu Ser Asn Glu Ala Leu Arg Ser Lys Val Ala Glu
            20                  25                  30

Leu Glu Arg Glu Val Lys Arg Lys Asp Ala Glu Leu Gln Glu Arg Glu
        35                  40                  45

Tyr His Leu Lys Glu Leu Arg Glu Gln Leu Ala Lys Gln Thr Val Ala
    50                  55                  60

Ile Ala Glu Leu Thr Glu Glu Leu Gln Ser Lys Cys Ile Gln Leu Asn
65                  70                  75                  80

Lys Leu Gln Asp Val Ile His Val Gln Gly Gly Ser Pro Leu Gln Ala
                85                  90                  95

Ser Pro Asp Lys Val Pro Leu Asp Val His Arg Lys Thr Ser Gly Leu
            100                 105                 110

Val Ser Leu His Ser Arg Arg Gly Ala Lys Ala Gly Val Ser Ala Glu
        115                 120                 125

Pro Thr Ser Arg Thr Tyr Asp Leu Asn Lys Pro Pro Glu Phe Ser Phe
    130                 135                 140

Glu Lys Ala Arg Val Arg Lys Asp Ser Ser Glu Lys Lys Leu Ile Thr
145                 150                 155                 160

Asp Ala Leu Asn Lys Asn Gln Phe Leu Lys Arg Leu Asp Pro Gln Gln
                165                 170                 175

Ile Lys Asp Met Val Glu Cys Met Tyr Gly Arg Asn Tyr Gln Gln Gly
            180                 185                 190
```

```
Ser Tyr Ile Val Lys Gln Gly Glu Pro Gly Asn His Ile Phe Val Leu
        195                 200                 205

Ala Glu Gly Arg Leu Glu Val Phe Gln Gly Glu Lys Leu Leu Ser Ser
    210                 215                 220

Ile Pro Met Trp Thr Thr Phe Gly Glu Leu Ala Ile Leu Tyr Asn Cys
225                 230                 235                 240

Thr Arg Thr Ala Ser Val Lys Ala Ile Thr Asn Val Lys Thr Trp Ala
                245                 250                 255

Leu Asp Arg Glu Val Phe Gln Asn Ile Met Arg Arg Thr Ala Gln Ala
            260                 265                 270

Arg Asp Glu Glu Tyr Arg Asn Phe Leu Arg Ser Val Ser Leu Leu Lys
        275                 280                 285

Asn Leu Pro Glu Asp Lys Leu Thr Lys Ile Ile Asp Cys Leu Glu Val
    290                 295                 300

Glu Tyr Tyr Asp Lys Gly Asp Tyr Ile Ile Arg Glu Gly Glu Glu Gly
305                 310                 315                 320

Ser Thr Phe Phe Ile Leu Ala Lys Gly Lys Val Lys Val Thr Gln Ser
                325                 330                 335

Thr Glu Gly His Asp Gln Pro Gln Leu Ile Lys Thr Leu Gln Lys Gly
            340                 345                 350

Glu Tyr Phe Gly Glu Lys Ala Leu Ile Ser Asp Asp Val Arg Ser Ala
        355                 360                 365

Asn Ile Ile Ala Glu Glu Asn Asp Val Ala Cys Leu Val Ile Asp Arg
    370                 375                 380

Glu Thr Phe Asn Gln Thr Val Gly Thr Phe Asp Glu Leu Gln Lys Tyr
385                 390                 395                 400

Leu Glu Gly Tyr Val Ala Thr Leu Asn Arg Asp Asp Glu Lys Arg His
                405                 410                 415

Ala Lys Arg Ser Met Ser Ser Trp Lys Leu Ser Lys Ala Leu Ser Leu
            420                 425                 430

Glu Met Ile Gln Leu Lys Glu Lys Val Ala Arg Phe Ser Ser Thr Ser
        435                 440                 445

Pro Phe Gln Asn Leu Glu Ile Ile Ala Thr Leu Gly Val Gly Gly Phe
    450                 455                 460

Gly Arg Val Glu Leu Val Lys Val Lys Asn Glu Asn Ile Ala Phe Ala
465                 470                 475                 480

Met Lys Cys Ile Arg Lys Lys His Ile Val Asp Thr Lys Gln Gln Glu
                485                 490                 495

His Val Tyr Ser Glu Lys Arg Ile Leu Glu Glu Leu Cys Ser Pro Phe
            500                 505                 510

Ile Val Lys Leu Tyr Arg Thr Phe Lys Asp Asn Lys Tyr Val Tyr Met
        515                 520                 525

Leu Leu Glu Ala Cys Leu Gly Gly Glu Leu Trp Ser Ile Leu Arg Asp
    530                 535                 540

Arg Gly Ser Phe Asp Glu Pro Thr Ser Lys Phe Cys Val Ala Cys Val
545                 550                 555                 560

Thr Glu Ala Phe Asp Tyr Leu His Arg Leu Gly Ile Ile Tyr Arg Asp
                565                 570                 575

Leu Lys Pro Glu Asn Leu Ile Leu Asp Ala Asp Gly Tyr Leu Lys Leu
            580                 585                 590

Val Asp Phe Gly Phe Ala Lys Lys Ile Gly Ser Gly Gln Lys Thr Trp
        595                 600                 605
```

```
Thr Phe Cys Gly Thr Pro Glu Tyr Val Ala Pro Glu Val Ile Leu Asn
    610             615             620
Lys Gly His Asp Phe Ser Val Asp Phe Trp Ser Leu Gly Ile Leu Val
625             630             635             640
Tyr Glu Leu Leu Thr Gly Asn Pro Pro Phe Ser Gly Ile Asp Gln Met
            645             650             655
Met Thr Tyr Asn Leu Ile Leu Lys Gly Ile Glu Lys Met Asp Phe Pro
            660             665             670
Arg Lys Ile Thr Arg Arg Pro Glu Asp Leu Ile Arg Arg Leu Cys Arg
            675             680             685
Gln Asn Pro Thr Glu Arg Leu Gly Asn Leu Lys Asn Gly Ile Asn Asp
690             695             700
Ile Lys Lys His Arg Trp Leu Asn Gly Phe Asn Trp Glu Gly Leu Lys
705             710             715             720
Ala Arg Ser Leu Pro Ser Pro Leu Arg Arg Glu Leu Ser Gly Pro Ile
            725             730             735
Asp His Ser Tyr Phe Asp Lys Tyr Pro Pro Glu Lys Gly Val Pro Pro
            740             745             750
Asp Glu Met Ser Gly Trp Asp Lys Asp Phe
            755             760
```